United States Patent
De Angelis et al.

(10) Patent No.: US 11,845,804 B2
(45) Date of Patent: Dec. 19, 2023

(54) CAR-CD30 T CELLS FOR TREATMENT OF CD30+ TUMORS

(71) Applicant: OSPEDALE PEDIATRICO BAMBINO GESU', Rome (IT)

(72) Inventors: Biagio De Angelis, Rome (IT); Concetta Quintarelli, Rome (IT); Ignazio Caruana, Rome (IT); Franco Locatelli, Rome (IT)

(73) Assignee: OSPEDALE PEDIATRICO BAMBINO GESU', Rome (IT)

( * ) Notice: Subject to any disclaimer, the term of this patent is extended or adjusted under 35 U.S.C. 154(b) by 304 days.

(21) Appl. No.: 16/979,839

(22) PCT Filed: Mar. 12, 2019

(86) PCT No.: PCT/IT2019/050053
§ 371 (c)(1),
(2) Date: Sep. 10, 2020

(87) PCT Pub. No.: WO2019/175910
PCT Pub. Date: Sep. 19, 2019

(65) Prior Publication Data
US 2021/0206863 A1 Jul. 8, 2021

(30) Foreign Application Priority Data
Mar. 13, 2018 (IT) .......................... 102018000003464

(51) Int. Cl.
*C07K 16/28* (2006.01)
*A61P 35/00* (2006.01)
(Continued)

(52) U.S. Cl.
CPC .......... *C07K 16/2878* (2013.01); *A61P 35/00* (2018.01); *C07K 14/7051* (2013.01);
(Continued)

(58) Field of Classification Search
CPC combination set(s) only.
See application file for complete search history.

(56) References Cited

U.S. PATENT DOCUMENTS

2017/0334967 A1 11/2017 Siegel et al.

FOREIGN PATENT DOCUMENTS

| CN | 107759699 | * | 3/2018 | ............. A61K 35/17 |
| CN | 107759699 A | | 3/2018 | |

(Continued)

OTHER PUBLICATIONS

Machine Translation of CN 107759699 obtained from Espacenet, 2022 (Year: 2022).*

(Continued)

*Primary Examiner* — Adam Weidner
*Assistant Examiner* — Laura Ann Essex
(74) *Attorney, Agent, or Firm* — Knobbe, Martens, Olson & Bear, LLP

(57) ABSTRACT

A third generation of CAR-CD30 T cells is for treatment of CD30+ Tumors such as lymphoid malignancies, leukemia, and solid tumors. A CD30 chimeric antigen receptor includes, from the N-terminus to the C– terminus, a signal peptide, which is linked by a first linker to an anti CD30 single chain antibody domain from AC10 hybridoma including the AC10 VL sequence and the AC10 VH sequence. The AC10 VL and VH sequences are linked by a second linker.

23 Claims, 23 Drawing Sheets

Specification includes a Sequence Listing.

(51) Int. Cl.
C07K 14/725 (2006.01)
C07K 14/705 (2006.01)
C12N 5/0783 (2010.01)
A61K 38/00 (2006.01)

(52) U.S. Cl.
CPC .. *C07K 14/70517* (2013.01); *C07K 14/70521* (2013.01); *C07K 14/70578* (2013.01); *C12N 5/0636* (2013.01); *A61K 38/00* (2013.01); *C07K 2317/622* (2013.01); *C07K 2319/02* (2013.01); *C07K 2319/03* (2013.01); *C07K 2319/33* (2013.01); *C12N 2501/2307* (2013.01); *C12N 2501/2315* (2013.01)

(56) References Cited

FOREIGN PATENT DOCUMENTS

| WO | WO 2013/153391 A1 | 10/2013 | |
|---|---|---|---|
| WO | WO-2015132604 A1 * | 9/2015 | ............ A61K 35/17 |
| WO | WO 2016/134284 A1 | 8/2016 | |
| WO | WO 2016/166630 A1 | 10/2016 | |
| WO | WO-2016196344 A1 * | 12/2016 | ............ A61P 1/04 |
| WO | WO 2017/066122 A1 | 4/2017 | |
| WO | WO-2018102795 A2 * | 6/2018 | ............ A61K 35/17 |
| WO | WO-2018213337 A1 * | 11/2018 | ............ A61K 35/17 |
| WO | WO-2019217327 A1 * | 11/2019 | ............ A61K 35/17 |

OTHER PUBLICATIONS

Quintarelli C, Orlando D, Boffa I, Guercio M, Polito VA, Petretto A, Lavarello C, Sinibaldi M, Weber G, Del Bufalo F, Giorda E, Scarsella M, Petrini S, Pagliara D, Locatelli F, De Angelis B, Caruana I. Oncoimmunology. Mar. 15, 2018;7(6):e1433518. doi: 10.1080/2162402X.2018.1433518. PMID: 29872565 (Year: 2018).*
Weinkove R, George P, Dasyam N, McLellan AD. Clin Transl Immunology. May 11, 2019;8(5):e1049. doi: 10.1002/cti2.1049. PMID: 31110702; PMCID: PMC6511336. (Year: 2019).*
Berger, et al. "Potential Application and Prevalence of the CD30 (Ki-1) Antigen Among Solid Tumors: A Focus Review of the Literature", Elsevier, *Critical Reviews in Oncology/Hematology*, 113 (2017), pp. 8-17.
Brudno, et al. "Chimeric Antigen Receptor T-Cell Therapies for Lymphoma", *Nature Reviews, Clinical Oncology*. vol. 15, Jan. 2018. pp. 31-46.
Cieri, et al. "IL-7 and IL-15 Instruct the Generation of Human Memory Stem T Cells from Naïve Precursors", *Blood*, Jan. 24, 2013, vol. 121, No. 4, pp. 573-584.
Condomines, et al. "Tumor-Targeted Human T Cells Expressing CD28-Based Chimeric Antigen Receptors Circumvent CTLA-4 Inhibition" *Plos One*, Jun. 25, 2015, pp. 1-15.
Evens, et al. "Treatment of Hodgkin Lymphoma: the Past, Present, and Future", *Nature Clinical Practice, Oncology*, Sep. 2008, vol. 5, No. 9. pp. 543-556.
Haverkos, et al. "PD-1 blockade for relapsed lymphoma post-allogeneic hematopoietic cell transplant: high response rate but frequent GCHD." Blood, Jul. 13, 2017. vol. 130, No. 2. pp. 221-227.
Heczey, et al. "CAR T Cells Administered in Combination with Lymphodepletion and pD-1 Inhibition to Patients with Neuroblastoma", *Molecular Therapy*, vol. 25, No. 9, Sep. 2017, pp. 2214-2224.
Hombach, et al. "An Anti-CD30 Chimeric Receptor That Mediates CD3-Independent T-Cell Activation against Hodgkins Lymphoma Cells in the Presence of Soluble CD30" *American Association for Cancer Research*, 1998. pp. 1116-1119.
Hombach, et al. "Arming Cytokine-Induced Killer Cells With Chimeric Antigen Receptors: CD28 Outperforms Combined CD28-OX40 Super-Stimulation", www.moleculartheraoy.com, vol. 21, No. 12, Dec. 2013, pp. 2268-2277.

Hombach, et al. "Characterization of a Chimeric T-Cell Receptor with Specificity for the Hodgkins Lymphoma-Associated CD30 Antigen" *Journal of Immunotherapy*, 22(6), pp. 473-480.
Hombach, et al. "OX40 Costimulation by a Chimeric Antigen Receptor Abrogates CD28 and IL-2 Induced IL-10 Secretion by Redirected CD4 T Cells", *OncoImmunologu* 1:4, Jul. 2012, pp. 458-466.
Hombach, et al. "Superior Therapeutic Index in Lymphoma Therapy: CD30 CD34 Hematopoietic Stem Cells Resist a Chimeric Antigen Receptor T-cell Attack", *The American Society of Gene and Cell Therapy*, vol. 24, No. 8, pp. 1423-1434.
Hudecek, et al. "The Nonsignaling Extracellular Spacer Domain of Chimeric Antigen Receptors is Decisive for In Vivo Antitumor Activity", *American Association for Cancer Research*, Sep. 11, 2014, pp. 125-135.
Karlsson, et al. "Evaluation of Intracellular Signaling Downstream Chimeric Antigen Receptors", *Plos One*, Dec. 23, 2015, pp. 1-20.
Klement, et al. "Effect of Linker Flexibility and Length on the Functionality of a Cytotoxic Engineered Antibody Fragment", *Journal of Biotechnology*, 2015, pp. 90-97.
Long, et al. "4-1 BB Costimulation Ameliorates T Cell Exhaustion Induced by Tonic Signaling of Chimeric Antigen Receptors", *Nat Med*, Jun. 2015, 21(6), pp. 581-590.
Louis, et al. "Antitumor activity and long-term fate of chimeric antigen receptor-positive T Cells in patients with neroblastoma" *Blood*, Dec. 1, 2011, Vo. 118, No. 23, pp. 6050-6056.
Maher, et al. "Human T-Lymphocyte Cytotoxicity and Proliferation Directed by a Signle Chimeric TXT/CD28 Receptor", *Nature Biotechnology*, vol. 20, Jan. 2002, pp. 70-75.
Perna, et al. "Interleukin-7 Mediates Selective Expansion of Tumor-Redirected Cytotoxic T Lymphocytes (CTLs) without Enhancement of Regulatory T-Cell Inhibition", *American Association for Cancer Research*, 2013, pp. 131-139.
Perna, et al. "Interleukin 15 Provides Relief to CTLs from Regulatory T Cell-Mediated Inhibition: Implications for Adoptive T Cell-Based Therapies for Lymphoma", *Clin Cancer Res*, 19(1), Jan. 1, 2013, pp. 106-117.
Pule, et al. "A Chimeric T Cell Antigen Receptor That Augments Cytokine Release and Supports Clonal Expansion of Primary Human T Cells", *Molecular Therapy*, vol. 12, No. 5, Nov. 2005, pp. 933-941.
Ramos, et al. "Clinical and Immuological Responses after CD30-specific Chimeric Antigen receptor-redirected Lymphocytes", *J Clin Invest*. 2017, 127(9) pp. 3462-3471.
Rezvani, et al. "Nonmyeloablative Allogenic Hematopoietic Cell Transplantation in Relapsed, Refractory, and Transformed Indolent Non-Hodgkin's Lymphoma", *Journal of Clinical Oncology*, Jan. 10, 2008. pp. 211-217.
Savoldo, et al. "Epstein Barr virus-specific cytotoxic T Lymphocytes Expressing the anti-CD30 Artificial Chimeric T-cell Receptor For Immunotherapy of Hodgkin Disease". *Blood*, Oct. 1, 2007, vol. 110, No. 7, pp. 2620-2630.
Singh, et al. "Manufacture of Clinical-Grade CD19-Specific T Cells Stably Expressing Chimeric Antigen Receptor Using Sleeping Beauty System and Artificial Antigen Presenting Cells", *Plos One*, May 2013, vol. 8, Issue 5, pp. e64138-e64138.
Stasi, et al. "T lymphocytes coexpressing CCR4 and a chimeric antigen receptor targeting CD30 have improved homing and anti-tumor activity in a Hodgkin tumor model", *Blood*, Jun. 18, 2009, vol. 113. No. 25. pp. 6392-6402.
Wang, et al. "Autologous T Cells expressing CD30 Chimeric Antigen Receptors for Relapsed or Refractory Hodgkin Lymphoma: An Open-Label Phase I Trail" *Clin Cancer Res*; 23(5) Mar. 1, 2017. pp. 1156-1166.
Wein, et al. "The Role of T Cells in the Microenvironment of Hodgkin Lymphoma" *Institute of Cell Biology (Cancer Research)*, vol. 99, Jan. 2016, pp. 45-50.
Wong, et al., "Enhancer Profiling Identifies Critical Cancer Genes and Characterizes Cell Identity in Adult T-cell Leukemia", *Blood*, Nov. 23, 2017, vol. 130, No. 21. pp. 2326-2338.
Zheng, et al. "CD30 Expression in Acute Lymphoblastic Leukemia as Assessed by Flow Cytometry Analysis", Leuk Lymphoma. Mar. 2014 ; 55(3): 624-627. doi:10.3109/10428194.2013.820293.

(56) References Cited

OTHER PUBLICATIONS

Zheng, et al. "Protein L: A Novel Reagent for the Detection of Chimeric Antigen Receptor (CAR) expression by flow cytometry", *Hournal of Translation Medicine*, 2012, pp. 1-6.

Zhong, et al. "Chimeric Antigen Receptors Combining 4-1BB and CD28 Signaling Domains Augment PI3Kinase/AKT/Bcl-XI Actication and CD8+ T Cell-mediated Tumor Eradication", Molecular Therapy, vol. 18, No. 2, Feb. 2010, pp. 413-420.

Quintarelli et al., "Choice of costimulatory domains and of cytokines determines CART-cell activity in neuroblastoma", Oncoimmunology, vol. 7, No. 6, Feb. 8, 2018.

International Search Report issued in application No. PCT/IT2019/050053, dated Jun. 7, 2019.

Abate-Daga et al., "CAR models: next-generation CAR modifications for enhanced T-cell function", Molecular Therapy—Oncolytics, vol. 3, pp. 1-7 (2016).

Tang et al., "Third-generation CD28/4-166 chimeric antigen receptor T cells for chemotherapy relapsed or refractory acute lymphoblastic leukaemia: a non-randomised, open-label phase I trial protocol", BMJ Open, vol. 6, pp. 1-7 (2016).

Notice of Reasons for Rejection issued in Japanese Application No. 2020-571929, dated Nov. 15, 2022.

\* cited by examiner

CAR-CD30 T CELLS FOR TREATMENT OF CD30+ TUMORS

REFERENCE TO SEQUENCE LISTING

A Substitute Sequence Listing submitted as an ASCII text file via EFS-Web is hereby incorporated by reference in accordance with 35 U.S.C. § 1.52(e). The name of the ASCII text file for the Substitute Sequence Listing is 2020 Dec. 22 Substitute Sequence Listing—BARZ038.001APC, the date of creation of the ASCII text file is Dec. 22, 2020, and the size of the ASCII text file is 34.9 KB.

BACKGROUND OF THE INVENTION

Field of the Invention

The present invention concerns CAR-CD30 T cells for treatment of CD30+ Tumors. In particular, the present invention concerns a third generation of CAR-CD30 T cells for treatment of CD30+ Tumors such as lymphoid malignancies, leukemia, solid tumors.

Description of the Related Art

It is known that the prognoses of most patients with chemotherapy-refractory or multiply-relapsed Non-Hodgkin's Lymphoma (NHL) or Hodgkin lymphoma (HL) remain poor(1). Although allogeneic HSCT (allo-HSCT) offers the potential to cure patients with various subtypes of lymphoma, transplant-related mortality remains high, and long-term sequelae, including chronic graft versus-host disease (GVHD), can have a substantial negative effect on quality of life(2).

The PD-1 blockade for relapsed lymphoma post allo-HSCT appears to be highly efficacious but frequently complicated by rapid onset of severe and treatment-refractory GVHD(3). CAR-T cells are emerging as a novel treatment modality for these patients.

CD30 (Ki-1) is a cell membrane protein derived from the tumor necrosis factor receptor superfamily 8 (TNFRSF8), and its normal expression is restricted to activated T and B cells. In tumor cells, CD30 expression is most commonly associated with lymphoid malignancies (Hodgkin and non-Hodgkin lymphomas, CD30+ acute lymphoblastic leukemia (ALL), of either T-cell(4) or B-cell lineage(5)). CD30 expression has been reported also in mostly adult non-lymphoid malignancies. Based on the published data, 24.5% of all solid tumors are also CD30+, most notably among germ cell tumors (myofibroblasticsarcoma (93%), embryonal carcinoma (77%), mesothelioma (77%), mixed Germ Cell Tumor (GCT) (65%), head and neck carcinoma (24%), yolk sac tumor (18%), angiosarcoma (14%), pituitary adenoma (11%) and seminomas (6%)), raising the possibility of CD30-targeted therapy for additional tumors(6).

While 90% of early-stage HL patients can be cured with conventional treatment, only 70% of advanced-stage patients are cured with standard therapeutic approaches. For HL patients with relapsed disease, only half are cured with standard salvage therapies (7).

Targeting CD30 with monoclonal antibodies in Hodgkin lymphoma (HL) and anaplastic large cell lymphoma (ALCL) has had profound clinical success. However, adverse events, mainly mediated by the toxin component of the conjugated antibodies, cause treatment discontinuation in many patients. Targeting CD30 with T cells expressing a CD30-specific chimeric antigen receptor (CAR) may reduce the side effects and augment antitumor activity.

Immunotherapeutic approaches targeting CD30 by CAR has been demonstrated of value in preclinical models(8, 9) and confirmed in two different independent clinical trials(10, 11), although clinical benefit was not optimal.

First-generation anti-CD30 CAR T cells were developed in the 1990s, and preclinical studies demonstrated the ability of these cells to lyse CD30-expressing HL cell lines in vitro(12, 13). Indeed, Epstein-Barr-virus-specific cytotoxic T cells transduced with an anti-CD30 CAR have been shown to have activity against CD30+ cancer cell lines in vitro, as well as in vivo, in a mouse xenograft model, improving the persistence of T cells in vivo(8).

Notably, the presence of soluble CD30 did not attenuate cytolysis while eliminating CD30+ lymphoma cells, suggesting that CD30 shed from HL cells into the blood would not inhibit the efficacy of anti CD30 CAR T cells in vivo(14).

In a first trial, an inconsistent response of lymphoma was observed, with the majority of patients presenting stable disease after CAR T cell multiple infusion, or no response at all. Overall, lymph nodes presented a better response than extranodal lesions, the response of lung lesions seemed to be relatively poor, and infused CAR T did not persisted more than 60 days after infusion. Notably, several clinical data(15, 16) clearly showed that the in vivo persistence of CAR-T cells is associate to better outcome of the treated patients. As summarized in table 1, in the first clinical trial described the authors considered a lentiviral platform carrying a second generation CAR characterized by the single-chain fragment variable (scFv) sequence specific for the CD30 antigen derived from AJ878606.1 hybridoma, the costimulatory domain derived from human CD137 in frame with CD3ζ signaling domains(10).

The first one open-label phase I clinical trial of anti-CD30 CAR T cells that were gene-modified with a lentiviral vector to express CD137 co-stimulatory domain involved eighteen patients suffering from relapsed or refractory Hodgkin lymphoma. The 18 patients included one with primary cutaneous anaplastic large cell lymphoma (ALCL) and 17 with Hodgkin lymphoma of 3 different subtypes, most of which were nodular sclerosis. Thirteen patients received 1 cycle of CAR T-cell infusion and five received 2 cycles.

Preliminary results of this study demonstrated seven achieved partial remission and six achieved stable disease. The objective response was 39%(10).

In a second trial, the majority of patients were treated with multiple infusions of CD30.CAR T cells achieving a transient response, and CD30.CAR-T cells were not more detectable after 6 weeks from infusion. As summarized in table 1, in this clinical trial the authors considered a retroviral platform carrying a second generation CAR characterized by the single-chain fragment variable (scFv) sequence specific for the CD30 antigen derived from HRS3 hybridoma, the costimulatory domain derived from human CD28 in frame with CD3ζ signaling domains.

TABLE 1

| Platform | CAR Generation | Single chain | trackable marker | Hinge | Trans-membrane | Costimulatory domains | Reference PMID |
|---|---|---|---|---|---|---|---|
| Lentiviral | 2 | AJ878606.1 | is not reported | CD8 | CD8 | CD137 | 7582488 |
| Retroviral | 2 | HRS3 | CH2-CH3 | CH2-CH3 | CD28 | CD28 | 28805662 |

Particularly, in the second clinical trial, 9 patients with relapsed/refractory HL or ALCL were infused with autologous T cells that were gene-modified with a retroviral vector to express the CD30-specific CAR (CD30.CAR-T) encoding the CD28 costimulatory endodomain. Of note, seven of these patients had brentuximab-refractory disease. Preliminary results of this study demonstrated complete response in 3 of 9 patients, and 3 had transient stable disease. CAR-T-cell persistence was <8 weeks in this study, but tumour biopsies showed efficient trafficking of T cells to lymphoma sites(11).

Both clinical trials teach that multiple CD30.CAR-T cells infusion was well tolerated. Host lymphodepletion before CAR-T infusion would be beneficial in further improving of CAR T cells expansion and their antitumor activity. More important the CAR-T-cell persistence correlate with clinical response.

All these data show that CD30.CAR-T cells are safe and can lead to clinical responses in patients with HL, although further optimization of this therapy is warranted to achieve longer in vivo persistence, and higher anti-tumor control especially at lymphoma recurrence.

In particular, the optimization of the approach should consider that the classical Hodgkin lymphoma (cHL) and the anaplastic large T-cell lymphoma are characterized by only a few malignant Reed-Sternberg and Hodgkin cells (HRS) and by an abundance of inflammatory cells. These non-malignant cells produce soluble or membrane-bound molecules involved in tumor immune-evasion. Moreover, HL tumor generates a chemokine milieu that significantly influences which T-cell subtypes traffic to and accumulate in the tumor(17). Indeed, HRS cells produce the chemokines TARC and MDC that attract T helper (Th2) cells and regulatory T cells (Tregs), which express CCR4, the receptor for these chemokines. The abundance of Tregs (and Th2 cells) in tumors including HL create a hostile immune microenvironment by impairing the antitumor activity of the few cytotoxic-effector T lymphocytes able to reach the tumor site. Forced expression of CCR4 on CD30-specific chimeric antigen receptor (CAR-CD30) improve the migration of CAR-CD30 T-redirected, effector T lymphocytes toward an HL-generated TARC gradient (9). HRS cells often express high level of PDL1 and produce the immunosuppressive IL-10, TGF-beta, Galectin1 and Prostaglandin E2, which inhibit T cell effector functions and induce apoptosis of activated Th1 and CD8+ T cells, through induction of CD95 ligand. It has been also recently showed that IL-15 selectively favors the survival, proliferation, and effector function of Epstein-Barr virus (EBV)-CTLs in the presence of T-regs(18). Moreover recently it has been shown that CAR-CD30 T cells grow in IL-7/IL-15 expressing higher levels of CXCR4 and CXCR3, which are chemokine receptors known to promote T cell migration to peripheral tissues (11).

Moreover, preclinical study showed that third generation of CAR-T cells combining CD28 and 4-1BB co-receptors may have superior in vitro activation and proliferation capacity compared with second generation CAR-T cells carrying CD28 signal domains, and both kinds of cells displayed in vivo comparable efficacy in eliminating CD19+B cells (19), although it was never demonstrated for CAR.CD30. Other CAR-CD30 T cells are known, such as those which are described in WO2017066122, WO2016134284 and CN107759699. For example, WO2017066122 compares 5F11-28Z, AC10-28Z and XmAb-28Z cells produced in IL2 condition.

High level of transduction efficiency of all CAR used is reported, however higher transduction efficiency is obtained with 5F11 in comparison to AC10 and XmAb (table A), namely higher percentage of transduction of CD8+CAR (80.7%) is obtained respect to AC10 (61.90%) or XmAb (64.70%) when the cells are growth in IL2 for 7 days. In addition, functional experiments are described concerning IFNγ production by co-culturing CAR-T cells with CD30+ tumors: SUDHL-1, HH and BV173. 5F11-28Z (growth in IL2) showed higher IFNγ production in comparison to AC10-28Z, when co-cultured with BV173, namely, TABLE D-1 shows that 5F11-28Z produced 3781 pg/ml of IFNγ, whereas AC10-28Z produced 538 pg/ml of IFNγ. Moreover 5F11-28Z produced 3534 pg/ml of IFNγ when co-cultured with HDML-2 cell line.

In the light of the above, it is therefore apparent the need to provide for further CAR CD30 T cells, which are able to overcome the disadvantages of the known CAR CD30 T cells.

SUMMARY OF THE INVENTION

According to the present invention, two novel CD30-specific chimeric antigen receptors (CAR-CD30) of third generation are now provided. Particularly, the following two clinical grade third generation of CAR CD30 SFG retroviral vectors are provided:

SFG.CAR.CD30(AC10)ΔCD34.CD8aTM.CD28cyto.4-1BB.ζ (28.4-1BB.ζ)

SFG.CAR.CD30(AC10) ΔCD34.CD8aTM.CD28cyto.OX40.ζ (28.OX40.ζ)

which comprise:

- a single chain variable fragment (scFv) from AC10 hybridoma, which was never applied for CAR therapy before;
- a trackable marker CD34 derived epitope (ΔCD34) of only 16 amino acid (aa) (as trackable marker) for a rapid identification by FACS (Fluorescence-activated cell sorting) System and/or selection by Cell Sorter System of gene modified T cells;
- an hinge represented by CD8 regions to avoid the immunogenic CH2-CH3 murine sequence applied in the vast majority of the similar CAR(20);
- a transmembrane domain from the transmembrane domain of CD8 to improve molecule stabilization;
- two costimulatory domains were added to the CAR-CD30 vector: CD28(21, 22) and OX40(23, 24) or CD28 and 4-1BB(25), both fused respectively to CD3-ζ chain. Therefore, the two SFG vectors can be distinguished by a single costimulatory domain (4-1BB for the first one and OX40 for the second vector).

In both CAR-CD30 the region, the trackable marker, the costimulatory domains and the CD3-ζ chain were codon optimized to improve the efficient protein expression.

Table 2 shows the differences of the CAR-CD30 according to the present invention in comparison with known CAR-CD30.

TABLE 2

| Platform | CAR Generation | Single chain | trackable marker | Hinge | Transmembrane (TM) | Costimulatory domains | Reference PMID |
|---|---|---|---|---|---|---|---|
| Lentiviral | 2 | AJ878606.1 | is not reported | CD8 | CD8 | CD 137 | 7582488 |
| Retroviral | 2 | HRS3 | CH2-CH3 | CH2-CH3 | CD28 | CD28 | 28805662 |
| Retroviral | 3 | AC10 | ΔCD34 (Codon optimized) | CD8 (Codon optimized) | CD8 (Codon optimized) | CD28 + CD137 (Codon optimized) CD28 + OX40 (Codon optimized) | non-applicable |

The above mentioned sequence of the CAR-CD30 according to the present invention as a whole provides unexpected advantages in comparison with the known CARs-CD30 such as a more efficient stable CAR-CD30 expression in T cells which is obtained by the use of a retroviral platform and CD8 TM domain, a longer in vivo persistence in comparison with that of the known CAR-CD30 T cells which depends on the costimulatory domain, high anti-tumor activities even in the presence of immuno-modulation and one single CAR-CD30 T cell administration thanks to the affinity of the scFv with the antigen and the choice of the production methods, such as the use of IL7/IL15 instead of IL2.

The in vitro and in vivo results herewith described show that modified polyclonal CD30CAR T cells according to the present invention were able to eliminate very efficiently, in long-term co-culture, CD30+ tumours. The biological products according to the present invention in xenograft in vivo model show to eliminate the Hodgkin and Non Hodgkin lymphomas and to establish a long immunological memory.

More in detail, the supernatants obtained by both SFG retroviral vector were able to transduce efficiently activated T cells, with very high level of transduction. The introduction in both construct of CD34 derived epitope as trackable marker let easily to track the genetically modified T cells (CD3+CD34+) in vitro and in vivo xenograft mouse model. The switching from IL2 to combination of IL7/IL15 improve the stability of expression of CAR-CD30 T cells, as showed by long-term in vitro culture, in particular for 28.OX40.ζ CAR T cells. In the setting of experiment the combination of IL7/IL15 improve the kinetics of proliferating T cells, in particular significantly evident after day +20 of in vitro expansion.

The in vitro culture for 15 days of CAR-CD30 T cells in IL7/IL15 induce a preferentially expansion of Effector Memory (EfM) T cells compartment respect T cell growth in IL2. Evaluating a day +15, CAR-CD30 T cells (IL2) for them exhaustion profile, a significative basal expression of PD1 and TIM3 was found, in particular in 28.OX40.ζ T cells. In vivo xenograft experiment model a long-term immunological memory which is able to eradicate for the second time the re-challenged tumour has been demonstrated for the first time.

The switching from IL2 to IL7/IL15 reduces significantly the PD1 expression, but increases only moderately TIM3 in both CAR T cells.

As reported by different authors, the presence of 4.1BB, by itself, reduces the exhaustion profile in CAR T cells (26). The culture condition (IL7/IL15) improves further the reduction of PD1 expression, in particular in 28.OX40.ζ T cells. To assess the role of basal PD1 expression on potency of CAR-modified T cells against PDL1+ tumor, CAR modified T cells were co-cultured with L428-PDL1 lymphoma cell line permanently transduced with PDL1, showing that no significant difference is found respect to Wild Type (WT) L428 cell line, even a lower effector/target ratios. Notable, in stressed long-term co-culture, unexpectedly the 28.OX40.ζ T cells show a significative superior lytic activity respect to 28.4-1BB.ζ T cells, against Karpas 299, a lower effector/target ratios (at ratio E:T 1:8 and 1:16) and HDML-2.

The results according to the present invention clearly show that (AC10) 28.4-1BB.ζ T cells or 28.OX40.ζ, growth in IL2, when cultured with HDML-2 (ratio effector:target 1:1), produce about 10303±3321.63 pg/ml and 29872.17±8572.18 pg/ml of IFNγ respectively (FIG. 9B), i.e. more than three time the IFNγ produced by 5F11-28Z described in WO2017066122, which produced 3534 pg/ml of IFNγ when co-cultured with HDML-2 cell line. Moreover, 28.4-1BB.ζ T cells growth in IL7/IL15 show even a higher IFNγ production: 21270.17±11621.21 pg/ml (FIG. 9E). In addition, 28.OX40.ζ T cells according to the present invention, when cultured with HDML-2, show even higher IFNγ production: 29872.17±8572.18 pg/ml (when they growth with IL2 (FIG. 9B)) and 34444.67±18872.62 pg/ml (when they growth with IL7/IL15)(FIG. 9E).

It was also observed that, when CAR-T cells according to the present invention are prepared in conditions comprising IL7 and IL15, higher long-term stability of expression of the CAR on T cells is obtained (FIG. 1D) in comparison to the CAR T cells prepared in conditions comprising IL2, especially with 28.OX40ζ. The stability of the detectable CAR of the present invention provides a stable expression of the CAR into the membrane of T cells (FIG. 1D). In particular, the ratio of transduction of CD8/CD4 at day +5, +15 and +30 was evaluated. Although the level of CD8 is lower respect to CD4 at DAY +5, the level of CD8 CAR+ increased over times from day +5 to day +15 in favor to CD8 (FIG. 1E-F). In addition, the presence of IL7/IL15 in the culture conditions improved significantly the fold expansion of CAR-T cells in comparison to conditions comprising IL2 as shown in FIGS. 1L and 1M.

FIG. 2 shows also that the presence of IL7/IL15 in the culture conditions are important in connection to the reduction of exhaustion profile of CAR-T Cells.

A long term persistence of 28.OX40.ζ T cells infused up to 240 days (FIG. 11) was also observed.

In addition, according to the present invention it was found that CAR.CD30 T cells with CD28.OX40 costimulatory domain were able to control Karpass 299 more efficiently with respect to CAR.CD30 T cells with 4.1BB costimulatory domain, during the sequential additions of CD30+ lymphoma up to 4 time ("stressed" co-culture) (FIG. 13A-B).

Interestingly, the percentage of CAR+ positive cells increased after the first tumor challenging, raising from 61.7%±18.4% and 74.0%±11.3% (day 0) to 93.4%±3.4% and 93.5%±3.1% (day +5) in 28.4-1BB.ζ T and 28.OX40.ζ T cells, respectively (p=0.049 and p=0.026)(FIG. 13C). Furthermore, with the subsequent tumor re-challenging the percentage and the Median Fluorescence Intensity (MFI) of genetically modified T cells remained stable over-time only for 28.OX40.ζ T cells (FIG. 13C-D).

Moreover, CAR.CD30 T cells with CD28.OX40 costimulatory domain produced significantly higher amount of IFN-gamma (FIG. 13E), IL-2 (FIG. 13F) and TNF-alpha (FIG. 13G) respect to 28.4-1BB.ζ when co-cultured with Karpa299 tumor cell line.

Moreover, both CAR-CD30 T cells show a cytotoxic effect also against solid CD30+ tumours, as the Desmoplastic cerebellar medulloblastoma DAOY (FIG. 5D and FIG. 7G), the Rhabdomyosarcoma RD tumour cell line (FIG. 7I-J) and the Embryonal Carcinoma. Overall, all this results make it highly plausible that the constructs according to the present invention can be used to treat efficiently CD30+ tumour patients.

Therefore, it is an object of the present invention a CD30 chimeric antigen receptor molecule comprising or consisting of, from the N-terminus to the C– terminus:

a) a signal peptide, such as a signal peptide comprising or consisting of MEFGLSWLFLVAILKGVQC (SEQ ID NO:1) (nucleotide ID NO:AB776838.1 and Protein ID NO: BAN63131.1), which is linked by a first linker to;

b) an anti CD30 single chain antibody domain from AC10 hybridoma comprising or consisting of the AC10 VL sequence: DIVLTQSPASLAVSLGQRATISCK-ASQSVDFDGDSYMNWYQQ KPGQPPKVLIYAASN-LESGIPARFSGSGSGTDFTLNIHPVEEEDAATYYC QQSNEDPWTFGGGTKLEIK (SEQ ID NO:2) and AC10 VH sequence: QIQLQQSGPEVVKPGASVKISCK-ASGYTFTDYYITWVKQKPG QGLEWIGWIYPGSGNT-KYNEKFKGKATLTVDTSSSTAFMQLSSLTSEDT AVYFCANYGNYWFAYWGQGTQVTVSA (SEQ ID NO: 3), said AC10 VL and VH sequences being linked by a second linker;

c) a trackable marker chosen from the group consisting of ΔCD34:ELPTQGTFSNVSTNVS (SEQ ID NO:4) (nucleotide ID NO AB238231.1 and Protein ID NO: BAE46748.1; ΔCD19:PEEPLVVKVEEGD-NAVLQCLKGTSDGPTQQLTWS RESPLKP-FLKLSLGLPGLGIHMRPLAIWLFIFNVSQQMGGFYL-CQPGPPS EKAWQPGWTVNVEGSGELFRWNVSDLG-GLGCGLKNRSSEGPSSPSG KLMSPKLYVWAKDRPEI-WEGEPPCLPPRDSLNQSLSQDLTMAPGSTLW LSCGVPPDSVSRG-PLSWTHVHPKGPKSLLSLELKDDRPARDMWVMET GLLLPRATAQDAGKYYCHRGNLTMSFHLEIT-ARPVLWHWLLRTGGWK(SEQ ID.NO:5)(nucleotide ID NO: M21097.1 and Protein ID NO: AAA35533.1); NGFR: KEACPTGLYTHSGECCKACNLGEGVAQPCGANQTV-CEPCLDSV TFSDVVSATEPCKPCTECVGLQSM-SAPCVEADDAVCRCAYGYYQDETT GRCEACRVCEAGSGLVFSCQDKQNTVCEECPDG-TYSDEANHVDPCLP CTVCEDTERQLRECTRWADAE-CEEIPGRWITRSTPPEGSDSTAPSTQEP EAPPEQDLI-ASTVAGVVTTVMGSSQPVVTRGTTDN (SEQ ID NO:6) (nucleotide ID NO: AK313654.1 and Protein ID NO: BAG36408.1); preferably ΔCD34:ELPTQGTFSNVSTNVS (SEQ ID NO:4) (nucleotide ID NO: AB238231.1 and Protein ID NO: BAE46748.1);

d) an hinge chosen from the group consisting of hingeCD8α: PAPRPPTPAPTIASQPLSLRPEACR-PAAGGAVHTRGLDFA (SEQ ID NO: 7) (nucleotide ID NO: M12828.1 and Protein ID NO: AAB04637.1); hinge CD28: IEVMYPPPYLD-NEKSNGTIIHVKGKHLCPSPLFPGPSKP (SEQ ID NO:8) (nucleotide ID NO: AJ517504.1 and Protein ID NO: CAD57003.1); hinge CH2-CH3 (UNIPROTKB:P01861): ESKYGPPCPSCPAPEFLGGPSVFLFPPKPKDTLMISRT-PEVTCVVVDVS QEDPE-VQFNWYVDGVEVHNAKTKPREEQFN-STYRVVSVLTVLHQDWL NGKEYKCKVSNKGLPSSIEKTISKAKGQPREPQVYTL PPSQEEMTKNQV SLTCLVKGFYPSDIA-VEWESNGQPEN NYKTTPPVLDSDGSFFLYSRLTV DKSRWQEGNVFSCSVMHEALHNHYTQKSLSLSLGK (SEQ ID NO:9); hinge CH3 (UNIPROTKB:P01861):ES-KYGPPCSPCPGQPREPQVYTLPPSQEEMTK NQVSLT-CLVKGFYPSDIAVEWESNGQPEN-NYKTTPPVLDSDGSFFLYSR LTVDKSRWQEGNVFSCSVMHEALHN-HYTQKSLSLSLGK (SEQ ID NO:10), preferably hinge CD8α: PAPRPPTPAPTIASQPLSLRPEACR-PAAGGAVHTRGLDFA (SEQ ID NO:7) (nucleotide ID NO: M12828.1 and Protein ID NO: AAB04637.1);

e) a trans membrane domain chosen from the group consisting of CD28TM: FWVLVVVGGVLACYSLL-VTVAFIIFWV (SEQ ID NO:13)(nucleotide ID NO: BC112085.1 and Protein ID NO: AA112086.1); CD8aTM (SEQ ID NO:14), preferably CD8aTM CDIYI-WAPLAGTCGVLLLSLVIT (SEQ ID NO:14) (nucleotide ID NO NM_001768.6 and Protein ID NO: NP_001759.3); and f) a co-stimulatory signalling domain chosen from the group consisting of the sequence obtained by linking CD28 cytoplasmic sequence: RSKRSRLLHSDYMNMT-PRRPGPTRKHYQPYAPPRDFAAYRS (SEQ ID NO:21) (nucleotide ID NO: AF222341.1 and Protein ID NO: AAF33792.1), CD137 (4-1BB) sequence: KRGRKKLLY-IFKQPFMRPVQTTQEEDGCSCRFPEEEEGGCEL (SEQ ID NO:22) (nucleotide ID NO: U03397.1 and Protein NO: AAA53133.1), and CD3-Zeta chain: RVKFSRSADAPA-YQQGQNQLYNELNLGRREEYDVLDKRR-GRDPEMGG KPRRKNPQEGLYNELQKDKMAEAYSEI-GMKGERRRGKGHDGLYQGLS TATKDTYDALHMQALPPR* (SEQ ID NO: 23) (nucleotide ID NO: J04132.1 And Protein ID: AAA60394.1) or the sequence obtained by linking CD28 cytoplasmic sequence RSKRSRLLHSDYMNMTPRRPGPTRKHYQPYAPPRD-FAAYRS (SEQ ID NO:21) (nucleotide ID NO: AF222341.1 and Protein ID NO: AAF33792.1), OX40 sequence RDQRLPPDAHKPPGGGSFRTPIQEEQADAHSTLAKI (SEQ ID NO:24) (nucleotide ID NO: NM_003327.3 and Protein NO: NP_003318.1) and CD3Zeta chain: RVKFSR-SADAPAYQQGQNQLYNELNLGRREEYDVLDKRR-GRDPEMGG KPRRKNPQEGLYNELQKDKMAEAYSEI-GMKGERRRGKGHDGLYQGLS TATKDTYDALHMQALPPR* (SEQ ID NO:23) (nucleotide ID NO: J04132.1 and Protein ID NO:AAA60394.1).

Hinge CD8α which is mentioned above comprises the sequence PAPRPPTPAPT (SEQ ID NO: 11) (spacer) and IASQPLSLRPEACRPAAGGAVHTRGLDFA(SEQ ID NO:12) (nucleotide ID NO NM_001768.6 and Protein ID NO: NP_001759.3).

The first linker can be a linker of two or three amino acids, such as SR.

The second linker which links AC10 VL and VH sequences can be chosen from the group consisting of a rigid linker prolines-rich, such as mouse igG3 upper hinge (mIgG3UH): PKPSTPPGSS (SEQ ID NO:15), (mIgG3UH)$_2$: PKPSTPPGSSPKPSTPPGSS (SEQ ID NO:16), or a flexible linker glycines-rich, such as (G4S)2 linker: GGGGSGGGG (SEQ ID NO:17), (G4S)4 linker: GGGGSGGGGSGGGGSGGGGS (SEQ ID NO:18), G4SG2 linker GGGGSGG (SEQ ID NO:19) or G3SG4 linker: GGGSGGGG (SEQ ID NO:20), preferably GGGSGGGG (SEQ ID NO:20).

In addition, a third linker can be used between AC10 VH sequence and the trackable marker, such as the short sequence GS.

One or more linkers (forth linker) can be present between the trans membrane domain and the co-stimulatory signalling domain such as CD8α cytoplasmic (cyto): LYCNHRN (SEQ ID NO:25) (nucleotide ID NO: NM_001768.6 and Protein ID NO: NP_001759.3) and EF.

According to an embodiment of the present invention, CD30 chimeric antigen receptor molecule comprises or consists of:

a) the signal peptide which comprises or consists of MEFGLSWLFLVAILKGVQC (SEQ ID NO:1), which is linked by a first linker to;

b) an anti CD30 single chain antibody domain from AC10 hybridoma comprising or consisting of the AC10 VL sequence: DIVLTQSPASLAVSLGQRATISCK-ASQSVDFDGDSYMNWYQQ KPGQPPKVLIYAASN-LESGIPARFSGSGSGTDFTLNIHPVEEEDAATYYC QQSNEDPWTFGGGTKLEIK (SEQ ID NO:2) and AC10 VH sequence: QIQLQQSGPEVVKPGASVKISCK-ASGYTFTDYYITWVKQKPG QGLEWIGWIYPGSGNT-KYNEKFKGKATLTVDTSSSTAFMQLSSLTSEDT AVYFCANYGNYWFAYWGQGTQVTVSA (SEQ ID NO: 3), said AC10 VL and VH sequences being linked by the second linker (G4S)2 linker: GGGGSGGGG (SEQ ID NO:17);

c) a trackable marker comprising or consisting of ΔCD34: ELPTQGTFSNVSTNVS (SEQ ID NO:4);

d) the hinge CD8α PAPRPPTPAPTIASQPLSLRPEACR-PAAGGAVHTRGLDFA (SEQ ID NO:7);

e) the trans membrane domain CD8aTM CDIYI-WAPLAGTCGVLLLSLVIT (SEQ ID NO:14), which is linked by one or more linkers, which comprise or consist of the linker CD8α cytoplasmic (cyto): LYCNHRN (SEQ ID NO:25), to f) the co-stimulatory signalling domain consisting of the sequence obtained by linking CD28 cytoplasmic sequence RSKRSRLLHSDYMNMTPRRPGPTRKHYQPYAPPRD-FAAYRS (SEQ ID NO:21), OX40 sequence RDQRLPP-DAHKPPGGSFRTPIQEEQADAHSTLAKI (SEQ ID NO:24) and CD3Zeta chain: RVKFSRSADAPA-YQQGQNQLYNELNLGRREEYDVLDKRR-GRDPEMGG KPRRKNPQEGLYNELQKDKMAEAYSEI-GMKGERRRGKGHDGLYQGLS TATKDTYDALHMQALPPR* (SEQ ID NO:23).

Alternatively, the CD30 chimeric antigen receptor molecule according to the present invention comprises or consists of:

a) the signal peptide which comprises or consists of MEFGLSWLFLVAILKGVQC (SEQ ID NO:1), which is linked by a first linker to;

b) an anti CD30 single chain antibody domain from AC10 hybridoma comprising or consisting of the AC10 VL sequence: DIVLTQSPASLAVSLGQRATISCK-ASQSVDFDGDSYMNWYQQ KPGQPPKVLIYAASN-LESGIPARFSGSGSGTDFTLNIHPVEEEDAATYYC QQSNEDPWTFGGGTKLEIK (SEQ ID NO:2) and AC10 VH sequence: QIQLQQSGPEVVKPGASVKISCK-ASGYTFTDYYITWVKQKPG QGLEWIGWIYPGSGNT-KYNEKFKGKATLTVDTSSSTAFMQLSSLTSEDT AVYFCANYGNYWFAYWGQGTQVTVSA (SEQ ID NO: 3), said AC10 VL and VH sequences being linked by the second linker (G4S)2 linker: GGGGSGGGG (SEQ ID NO:17);

c) a trackable marker comprising or consisting of ΔCD34: ELPTQGTFSNVSTNVS (SEQ ID NO:4);

d) the hinge CD8α PAPRPPTPAPTIASQPLSLRPEACR-PAAGGAVHTRGLDFA (SEQ ID NO:7);

e) the trans membrane domain CD8aTM CDIYI-WAPLAGTCGVLLLSLVIT (SEQ ID NO:14), which is linked by one or more linkers, which comprise or consist of CD8α cytoplasmic (cyto): LYCNHRN(SEQ ID NO:25), to f) the co-stimulatory signalling domain consisting of the sequence obtained by linking CD28 cytoplasmic sequence: RSKRSRLLHSDYMNMTPRRPGPTRKHYQPYAPPRD-FAAYRS (SEQ ID NO:21), CD137 (4-1BB) sequence: KRGRKKLLY-IFKQPFMRPVQTTQEEDGCSCRFPEEEEGGCEL (SEQ ID NO:22), and CD3-Zeta chain:

```
                                    (SEQ ID NO: 23)
RVKFSRSADAPAYQQGQNQLYNELNLGRREEYDVLDKRRGRDPEMGG

KPRRKNPQEGLYNELQKDKMAEAYSEIGMKGERRRGKGHDGLYQGLS

TATKDTYDALHMQALPPR*.
```

According to a preferred embodiment of the present invention CD30 chimeric antigen receptor molecule is:

```
                                    (SEQ ID NO: 26)
MEFGLSWLFLVAILKGVQCSRDIVLTQSPASLAVSLGQRATISCKASQSV

DFDGDSYMNWYQQKPGQPPKVLIYAASNLESGIPARFSGSGSGTDFTL

NIHPVEEEDAATYYCQQSNEDPWTFGGGTKLEIKGGGSGGGGQIQLQQ

SGPEVVKPGASVKISCKASGYTFTDYYITWVKQKPGQGLEWIGWIYPGS

GNTKYNEKFKGKATLTVDTSSSTAFMQLSSLTSEDTAVYFCANYGNYWF

AYWGQGTQVTVSAGSELPTQGTFSNVSTNVSPAPRPPTPAPTIASQPLS

LRPEACRPAAGGAVHTRGLDFACDIYIWAPLAGTCGVLLLSLVITLYCNH

RNEFRSKRSRLLHSDYMNMTPRRPGPTRKHYQPYAPPRDFAAYRSKR

GRKKLLYIFKQPFMRPVQTTQEEDGCSCRFPEEEEGGCELRVKFSRSA

DAPAYQQGQNQLYNELNLGRREEYDVLDKRRGRDPEMGGKPRRKNPQ

EGLYNELQKDKMAEAYSEIGMKGERRRGKGHDGLYQGLSTATKDTYDA

LHMQALPPR*.
```

Namely, this sequence, herewith named also as SFG.CAR.CD30(AC10)ΔCD34.CD8aTM.CD28cyto.4-1BB.ζ, comprises the following sequences:

Signal Peptide
MEFGLSWLFLVAILKGVQC (SEQ ID NO:1) (nucleotide ID NO: AB776838.1 and Protein ID NO: BAN63131.1)
Link
SR (connection sequence)
VL (AC10)

(SEQ ID NO: 2)
DIVLTQSPASLAVSLGQRATISCKASQSVDFDGDSYMNWYQQKPGQPP

KVLIYAASNLESGIPARFSGSGSGTDFTLNIHPVEEEDAATYYCQQSNED

PWTFGGGTKLEIK

Flex
GGGSGGGG (G3SG4 Linker) (SEQ ID NO:20)
VH (AC10)

(SEQ ID NO: 3)
QIQLQQSGPEVVKPGASVKISCKASGYTFTDYYITWVKQKPGQGLEWIG

WIYPGSGNTKYNEKFKGKATLTVDTSSSTAFMQLSSLTSEDTAVYFCAN

YGNYWFAYWGQGTQVTVSA

Link
GS (connection sequence)
ΔCD34
ELPTQGTFSNVSTNVS (SEQ ID NO:4) (nucleotide ID NO: AB238231.1 and Protein ID NO:BAE46748.1)
Hinge (Spacer) Extracellular
PAPRPPTPAPT (spacer) (SEQ ID NO:11)
Hinge (CD8a) Extracellular
IASQPLSLRPEACRPAAGGAVHTRGLDFA (SEQ ID NO:12) (nucleotide ID NO:NM_001768.6 and Protein ID NO: NP_001759.3)
CD8a (TM) Transmembrane
CDIYIWAPLAGTCGVLLLSLVIT (SEQ ID NO:14) (nucleotide ID NO: NM_001768.6 and Protein ID NO: NP_001759.3)
CD8a cytoplasmic (cyto) link of connection
LYCNHRN(SEQ ID NO:25) (nucleotide ID NO: NM_001768.6 and Protein ID NO: NP_001759.3)
Link of CONNECTION
EF(connection sequence)
CD28 cyto
RSKRSRLLHSDYMNMTPRRPGPTRKHYQPYAPPRDFAAYRS(SEQ ID NO:21) (nucleotide ID NO: AF222341.1 and Protein ID NO: AAF33792.1)
4.1BB
KRGRKKLLY-IFKQPFMRPVQTTQEEDGCSCRFPEEEEGGCEL(SEQ ID NO:22) (nucleotide ID NO: U03397.1 and Protein NO: AAA53133.1)
CD3 Zeta Chain
RVKFSRSADAPAYQQGQNQLYNELNLGRREEY-DVLDKRRGRDPEMGG KPRRKNPQEGLYNELQKDK-MAEAYSEIGMKGERRRGKGHDGLYQGLS TATKDTY-DALHMQALPPR*(SEQ ID NO: 23) (nucleotide ID NO: J04132.1 and Protein ID NO:AAA60394.1)

According to a further preferred embodiment of the present invention, CD30 chimeric antigen receptor is (SEQ ID NO: 27)
MEFGLSWLFLVAILKGVQCSRDIVLTQSPASLAVSLGQRATISCKASQSV

DFDGDSYMNWYQQKPGQPPKVLIYAASNLESGIPARFSGSGSGTDFTL

NIHPVEEEDAATYYCQQSNEDPWTFGGGTKLEIKGGGSGGGGQIQLQQ

SGPEVVKPGASVKISCKASGYTFTDYYITWVKQKPGQGLEWIGWIYPGS

GNTKYNEKFKGKATLTVDTSSSTAFMQLSSLTSEDTAVYFCANYGNYWF

AYWGQGTQVTVSAGSELPTQGTFSNVSTNVSPAPRPPTPAPTIASQPLS

LRPEACRPAAGGAVHTRGLDFACDIYIWAPLAGTCGVLLLSLVITLYCNH

RNEFRSKRSRLLHSDYMNMTPRRPGPTRKHYQPYAPPRDFAAYRSRD

QRLPPDAHKPPGGGSFRTPIQEEQADAHSTLAKIRVKFSRSADAPAYQQ

GQNQLYNELNLGRREEYDVLDKRRGRDPEMGGKPRRKNPQEGLYNEL

QKDKMAEAYSEIGMKGERRRGKGHDGLYQGLSTATKDTYDALHMQALP

PR*.

Namely, this sequence, herewith named also as SFG.CAR.CD30(AC10) ΔCD34.CD8aTM.CD28cyto.OX40.ζ, comprises the following sequences:
Signal Peptide
MEFGLSWLFLVAILKGVQC (SEQ ID NO:1) (nucleotide ID NO:AB776838.1 and Protein ID NO: BAN63131.1)
Link
SR (connection sequence)
VL (AC10)

(SEQ ID NO: 2)
DIVLTQSPASLAVSLGQRATISCKASQSVDFDGDSYMNWYQQKPGQPP

KVLIYAASNLESGIPARFSGSGSGTDFTLNIHPVEEEDAATYYCQQSNED

PWTFGGGTKLEIK

Flex
GGGSGGGG(G3SG4 Linker)(SEQ ID NO:20)
VH (AC10)

(SEQ ID NO: 3)
QIQLQQSGPEVVKPGASVKISCKASGYTFTDYYITWVKQKPGQGLEWIG

WIYPGSGNTKYNEKFKGKATLTVDTSSSTAFMQLSSLTSEDTAVYFCAN

YGNYWFAYWGQGTQVTVSA

Link
GS (connection sequence)
ΔCD34
ELPTQGTFSNVSTNVS(SEQ ID NO:4) (nucleotide ID NO:AB238231.1 and Protein ID NO:BAE46748.1)
Hinge (Spacer) Extracellular
PAPRPPTPAPT (spacer) (SEQ ID NO:11)
Hinge (CD8a) Extracellular
IASQPLSLRPEACRPAAGGAVHTRGLDFA(SEQ ID NO:12) (nucleotide ID NO:NM_001768.6 and Protein ID NO: NP_001759.3)
CD8a (TM) Transmembrane
CDIYIWAPLAGTCGVLLLSLVIT(SEQ ID NO:14) (nucleotide ID NO: NM_001768.6 and Protein ID NO: NP_001759.3)

CD8a cytoplasmic (cyto) link of connection
LYCNHRN(SEQ ID NO:25) (nucleotide ID NO: NM_001768.6 and Protein ID NO: NP_001759.3)
Link of Connection
EF(connection sequence)
CD28 Cyto
RSKRSRLLHSDYMNMTPRRPGPTRKHYQPYAPPRD-FAAYRS(SEQ ID NO:21) (nucleotide ID NO: AF222341.1 and Protein ID NO: AAF33792.1) OX40 RDQRLPP-DAHKPPGGGSFRTPIQEEQADAHSTLAKI(SEQ ID NO:24) (nucleotide ID No:NM_003327.3 and Protein NO: NP_003318.1)
CD3 Zeta Chain
RVKFSRSADAPAYQQGQNQLYNELNLGRREEY-DVLDKRRGRDPEMGG KPRRKNPQEGLYNELQKDK-MAEAYSEIGMKGERRRGKGHDGLYQGLS TATKDTY-DALHMQALPPR*(SEQ ID NO:23) (nucleotide ID NO:J04132.1 and Protein ID NO:AAA60394.1)

The present invention concerns also a nucleotide sequence which encodes CD30 chimeric antigen receptor described above.

According to an embodiment of the present invention, the nucleotide sequence is (SEQ ID NO: 28)
ATGGAGTTTGGGCTCTCCTGGCTCTTCCTGGTCGCGATTCTGAAGGG

GGTCCAGTGTTCACGAGATATCGTCCTGACTCAGAGTCCTGCCAGCC

TGGCAGTCTCCCTGGGACAGAGAGCTACCATAAGTTGTAAAGCATCA

CAGTCTGTTGATTTCGATGGCGACAGCTATATGAATTGGTACCAGCAA

AAACCCGGCCAGCCCCCGAAAGTTTTGATCTATGCAGCCTCTAACTT

GGAAAGCGGCATTCCTGCGCGATTCAGTGGCAGCGGGAGTGGTACA

GATTTCACCCTGAACATACACCCAGTCGAAGAGGAGGACGCAGCCAC

ATATTACTGCCAACAATCTAACGAGGATCCATGGACTTTTGGGGGCG

GCACTAAACTCGAAATCAAGGGCGGAGGTTCAGGCGGAGGAGGGCA

GATTCAACTGCAGCAATCAGGACCCGAGGTGGTCAAACCAGGTGCC

AGTGTCAAGATATCTTGCAAGGCATCCGGATATACATTTACCGACTAT

TACATTACCTGGGTCAAGCAGAAACCCGGCAAGGACTTGAATGGAT

TGGATGGATCTACCCTGGTAGCGGCAACACCAAATACAACGAAAAGT

TTAAAGGGAAGGCAACCCTGACTGTAGACACCTCCAGCTCCACAGCA

TTCATGCAGCTCTCCTCACTGACCTCCGAGGACACAGCAGTGTATTT

CTGTGCTAATTACGGTAATTACTGGTTCGCCTATTGGGGCCAGGGAA

CCCAAGTGACCGTTTCAGCTGGATCCGAACTTCCTACTCAGGGGACT

TTCTCAAACGTTAGCACAAACGTAAGTCCCGCCCAAGACCCCCCAC

ACCTGCGCCGACCATTGCTTCTCAACCCCTGAGTTTGAGACCCGAGG

CCTGCCGGCCAGCTGCCGGCGGGCCGTGCATACAAGAGGACTCG

ATTTCGCTTGCGACATCTACATCTGGGCTCCCCTCGCTGGCACCTGT

GGGGTGCTGCTGCTGTCACTCGTGATCACCCTTTATTGCAACCATCG

AAACGAATTCAGAAGTAAACGGTCAAGGCTTCTGCACAGCGATTATAT

GAATATGACACCAAGAAGACCTGGTCCAACCCGGAAACACTATCAGC

CCTACGCGCCCCCTAGAGACTTCGCAGCATACCGCTCTAAGAGAGG

-continued
GAGAAAAAAATTGCTCTATATTTTTAAACAACCATTTATGAGGCCCGTA

CAGACAACTCAGGAAGAGGATGGCTGTAGTTGCCGCTTCCCAGAGG

AGGAGGAAGGAGGCTGCGAGTTGAGAGTTAAATTCAGTAGAAGTGC

GGATGCGCCTGCTTACCAGCAGGGCCAGAACCAACTGTACAATGAAC

TGAATCTCGGGCGCCGAGAAGAGTATGACGTCCTCGATAAGCGGAG

GGGTAGGGATCCTGAAATGGGTGGGAAGCCAAGAAGAAAAAACCCC

CAGGAAGGACTGTATAACGAACTTCAGAAGGACAAGATGGCAGAGG

CCTACTCTGAGATTGGCATGAAAGGCGAACGACGGCGCGGTAAAGG

TCATGACGGGCTGTACCAGGGCCTGTCCACAGCGACGAAGGACACT

TACGACGCCCTGCACATGCAGGCACTCCCCCCCAGGTGA.

Namely, this nucleotide sequence, which encodes the sequence named also as SFG.CAR.CD30(AC10) ΔCD34.CD8aTM.CD28cyto.4-1BB.ζ, comprises the following sequences:
Signal Peptide (SEQ ID NO: 29)
ATGGAGTTTGGGCTCTCCTGGCTCTTCCTGGTCGCGATTCTGAAGGG GGTCCAGTGTTCACGA (nucleotide ID NO: AB776838.1)

VL (AC10)

(SEQ ID NO: 30)
GATATCGTCCTGACTCAGAGTCCTGCCAGCCTGGCAGTCTCCCTGGG

ACAGAGAGCTACCATAAGTTGTAAAGCATCACAGTCTGTTGATTTCGA

TGGCGACAGCTATATGAATTGGTACCAGCAAAAACCCGGCCAGCCCC

CGAAAGTTTTGATCTATGCAGCCTCTAACTTGGAAAGCGGCATTCCTG

CGCGATTCAGTGGCAGCGGGAGTGGTACAGATTTCACCCTGAACATA

CACCCAGTCGAAGAGGAGGACGCAGCCACATATTACTGCCAACAATC

TAACGAGGATCCATGGACTTTTGGGGCGGCACTAAACTCGAAATCA

AG

Flex
GGCGGAGGTTCAGGCGGAGGAGGG(G3SG4 Linker) (SEQ ID NO:31)
VH (AC10)

(SEQ ID NO: 32)
GATATCGTCCTGACTCAGAGTCCTGCCAGCCTGGCAGTCTCCCTGGG

ACAGAGAGCTACCATAAGTTGTAAAGCATCACAGTCTGTTGATTTCGA

TGGCGACAGCTATATGAATTGGTACCAGCAAAAACCCGGCCAGCCCC

CGAAAGTTTTGATCTATGCAGCCTCTAACTTGGAAAGCGGCATTCCTG

CGCGATTCAGTGGCAGCGGGAGTGGTACAGATTTCACCCTGAACATA

CACCCAGTCGAAGAGGAGGACGCAGCCACATATTACTGCCAACAATC

TAACGAGGATCCATGGACTTTTGGGGCGGCACTAAACTCGAAATCA

AG

Link (BamH1 Restriction Site)
GGATCC (BamH1 restriction site and connection sequence) (SEQ ID NO:33)
ΔCD34
GAACTTCCTACTCAGGGGACTTTCTCAAACGT-TAGCACAAACGTAAGT (SEQ ID NO: 34) (nucleotide ID NO:AB238231.1)
Hinge (CD8a) Extracellular (SEQ ID NO: 35)
CCCGCCCCAAGACCCCCCACACCTGCGCCGACCATTGCTTCTCAAC

CCCTGAGTTTGAGACCCGAGGCCTGCCGGCCAGCTGCCGGCGGGG

CCGTGCATACAAGAGGACTCGATTTCGCT (NM_001768.6)
CD8a (TM) Transmembrane (SEQ ID NO: 36)
TGCGACATCTACATCTGGGCTCCCCTCGCTGGCACCTGTGGGGTGC

TGCTGCTGTCACTCGTGATCACC (NM_001768.6)

CD8a Cytoplasmic (Cyto) Link of Connection
CTTTATTGCAACCATCGAAAC(SEQ ID NO:37) (NM_001768.6)
Link (EcoR1 Restriction Site and Connection Sequence) GAATTC (SEQ ID NO:38)
CD28 Cyto (SEQ ID NO: 39)
AGAAGTAAACGGTCAAGGCTTCTGCACAGCGATTATATGAATATGACA

CCAAGAAGACCTGGTCCAACCCGGAAACACTATCAGCCCTACGCGC

CCCCTAGAGACTTCGCAGCATACCGCTCT (AF222341.1)

4.1BB (SEQ ID NO: 40)
AAGAGAGGGAGAAAAAAATTGCTCTATATTTTTAAACAACCATTTATGA

GGCCCGTACAGACAACTCAGGAAGAGGATGGCTGTAGTTGCCGCTT

CCCAGAGGAGGAGGAAGGAGGCTGCGAGTTG (U03397.1)
CD3 Zeta Chain (SEQ ID NO: 41)
AGAGTTAAATTCAGTAGAAGTGCGGATGCGCCTGCTTACCAGCAGGG

CCAGAACCAACTGTACAATGAACTGAATCTCGGGCGCCGAGAAGAGT

ATGACGTCCTCGATAAGCGGAGGGGTAGGGATCCTGAAATGGGTGG

GAAGCCAAGAAGAAAAACCCCCAGGAAGGACTGTATAACGAACTTC

AGAAGGACAAGATGGCAGAGGCCTACTCTGAGATTGGCATGAAAGG

CGAACGACGGCGCGGTAAAGGTCATGACGGGCTGTACCAGGGCCTG

TCCACAGCGACGAAGGACACTTACGACGCCCTGCACATGCAGGCAC

TCCCCCCCAGGTGA (J04132.1)

According to a further embodiment of the present invention, the nucleotide sequence is (SEQ ID NO: 42)
ATGGAGTTTGGGCTCTCCTGGCTCTTCCTGGTCGCGATTCTGAAGGG

GGTCCAGTGTTCACGAGATATCGTCCTGACTCAGAGTCCTGCCAGCC

TGGCAGTCTCCCTGGGACAGAGAGCTACCATAAGTTGTAAAGCATCA

CAGTCTGTTGATTTCGATGGCGACAGCTATATGAATTGGTACCAGCAA

AAACCCGGCCAGCCCCCGAAAGTTTTGATCTATGCAGCCTCTAACTT

GGAAAGCGGCATTCCTGCGCGATTCAGTGGCAGCGGGAGTGGTACA

GATTTCACCCTGAACATACACCCAGTCGAAGAGGAGGACGCAGCCAC

ATATTACTGCCAACAATCTAACGAGGATCCATGGACTTTTGGGGGCG

GCACTAAACTCGAAATCAAGGGCGGAGGTTCAGGCGGAGGAGGGCA

GATTCAACTGCAGCAATCAGGACCCGAGGTGGTCAAACCAGGTGCC

AGTGTCAAGATATCTTGCAAGGCATCCGGATATACATTTACCGACTAT

TACATTACCTGGGTCAAGCAGAAACCCGGGCAAGGACTTGAATGGAT

TGGATGGATCTACCCTGGTAGCGGCAACACCAAATACAACGAAAAGT

TTAAAGGGAAGGCAACCCTGACTGTAGACACCTCCAGCTCCACAGCA

TTCATGCAGCTCTCCTCACTGACCTCCGAGGACACAGCAGTGTATTT

CTGTGCTAATTACGGTAATTACTGGTTCGCCTATTGGGGCCAGGGAA

CCCAAGTGACCGTTTCAGCTGGATCCGAACTTCCTACTCAGGGGACT

TTCTCAAACGTTAGCACAAACGTAAGTCCCGCCCCAAGACCCCCCAC

ACCTGCGCCGACCATTGCTTCTCAACCCCTGAGTTTGAGACCCGAGG

CCTGCCGGCCAGCTGCCGGCGGGGCCGTGCATACAAGAGGACTCG

ATTTCGCTTGCGACATCTACATCTGGGCTCCCCTCGCTGGCACCTGT

GGGGTGCTGCTGCTGTCACTCGTGATCACCCTTTATTGCAACCATCG

AAACGAATTCAGAAGTAAACGGTCAAGGCTTCTGCACAGCGATTATAT

GAATATGACACCAAGAAGACCTGGTCCAACCCGGAAACACTATCAGC

CCTACGCGCCCCCTAGAGACTTCGCAGCATACCGCTCTCGCGATCAA

AGACTCCCGCCCGATGCCCACAAACCCCTGGCGGGGCAGCTTTA

GGACACCCATTCAAGAAGAGCAGGCAGACGCCCACAGCACCTTGGC

CAAAATTAGAGTTAAATTCAGTAGAAGTGCGGATGCGCCTGCTTACCA

GCAGGGCCAGAACCAACTGTACAATGAACTGAATCTCGGGCGCCGA

GAAGAGTATGACGTCCTCGATAAGCGGAGGGGTAGGGATCCTGAAA

TGGGTGGGAAGCCAAGAAGAAAAACCCCCAGGAAGGACTGTATAA

CGAACTTCAGAAGGACAAGATGGCAGAGGCCTACTCTGAGATTGGCA

TGAAAGGCGAACGACGGCGCGGTAAAGGTCATGACGGGCTGTACCA

GGGCCTGTCCACAGCGACGAAGGACACTTACGACGCCCTGCACATG

CAGGCACTCCCCCCCAGGTGA

Namely, this nucleotide sequence, which encodes the sequence named also as SFG.CAR.CD30(AC10)ΔCD34.CD8aTM.CD28cyto.OX40.ζ, comprises the following sequences:

Signal Peptide (SEQ ID NO: 29)
ATGGAGTTTGGGCTCTCCTGGCTCTTCCTGGTCGCGATTCTGAAGGG

GGTCCAGTGTTCACGA (AB776838.1)

VL (AC10)

(SEQ ID NO: 30)
GATATCGTCCTGACTCAGAGTCCTGCCAGCCTGGCAGTCTCCCTGGG

ACAGAGAGCTACCATAAGTTGTAAAGCATCACAGTCTGTTGATTTCGA

TGGCGACAGCTATATGAATTGGTACCAGCAAAAACCCGGCCAGCCCC

CGAAAGTTTGATCTATGCAGCCTCTAACTTGGAAAGCGGCATTCCTG

CGCGATTCAGTGGCAGCGGGAGTGGTACAGATTTCACCCTGAACATA

CACCCAGTCGAAGAGGAGGACGCAGCCACATATTACTGCCAACAATC

TAACGAGGATCCATGGACTTTTGGGGCGGCACTAAACTCGAAATCA

AG

Flex
GGCGGAGGTTCAGGCGGAGGAGGG(G3SG4 Linker)
(SEQ ID NO:31)
VH (AC10)

(SEQ ID NO: 32)
GATATCGTCCTGACTCAGAGTCCTGCCAGCCTGGCAGTCTCCCTGGG

ACAGAGAGCTACCATAAGTTGTAAAGCATCACAGTCTGTTGATTTCGA

TGGCGACAGCTATATGAATTGGTACCAGCAAAAACCCGGCCAGCCCC

CGAAAGTTTTGATCTATGCAGCCTCTAACTTGGAAAGCGGCATTCCTG

CGCGATTCAGTGGCAGCGGGAGTGGTACAGATTTCACCCTGAACATA

CACCCAGTCGAAGAGGAGGACGCAGCCACATATTACTGCCAACAATC

TAACGAGGATCCATGGACTTTTGGGGCGGCACTAAACTCGAAATCA

AG

Link (BamH1 Restriction Site and Connection Sequence)
GGATCC (SEQ ID NO:33)
ΔCD34

(SEQ ID NO: SEQ ID NO: 34)
GAACTTCCTACTCAGGGGACTTTCTCAAACGTTAGCACAAACGTAAGT
(AB238231.1)

Hinge (CD8a) Extracellular (SEQ ID NO: 35)
CCCGCCCCAAGACCCCCCACACCTGCGCCGACCATTGCTTCTCAAC

CCCTGAGTTTGAGACCCGAGGCCTGCCGGCCAGCTGCCGGCGGGG

CCGTGCATACAAGAGGACTCGATTTCGCT (NM_001768.6)

(NM_001768.6)
CD8a (TM) Transmembrane (SEQ ID NO: 36)
TGCGACATCTACATCTGGGCTCCCCTCGCTGGCACCTGTGGGGTGC

TGCTGCTGTCACTCGTGATCACC (NM_001768.6)

CD8a Cytoplasmic (Cyto) Link of connection
CTTTATTGCAACCATCGAAAC(SEQ ID NO:37)
(NM_001768.6) Link (EcoR1 restriction site and connection sequence)
GAATTC (SEQ ID NO:38)
CD28 Cyto (SEQ ID NO: 39)
AGAAGTAAACGGTCAAGGCTTCTGCACAGCGATTATATGAATATGACA

CCAAGAAGACCTGGTCCAACCCGGAAACACTATCAGCCCTACGCGC

CCCCTAGAGACTTCGCAGCATACCGCTCT (AF222341.1)

(AF222341.1)
OX40

(SEQ ID NO: 43)
CGCGATCAAAGACTCCCGCCCGATGCCCACAAACCCCCTGGCGGGG

GCAGCTTTAGGACACCCATTCAAGAAGAGCAGGCAGACGCCCACAG

CACCTTGGCCAAAATT (NM_003327.3)

CD3 Zeta Chain (SEQ ID NO: 41)
AGAGTTAAATTCAGTAGAAGTGCGGATGCGCCTGCTTACCAGCAGGG

CCAGAACCAACTGTACAATGAACTGAATCTCGGGCGCCGAGAAGAGT

ATGACGTCCTCGATAAGCGGAGGGGTAGGGATCCTGAAATGGGTGG

GAAGCCAAGAAGAAAAAACCCCCAGGAAGGACTGTATAACGAACTTC

AGAAGGACAAGATGGCAGAGGCCTACTCTGAGATTGGCATGAAAGG

CGAACGACGGCGCGGTAAAGGTCATGACGGGCTGTACCAGGGCCTG

TCCACAGCGACGAAGGACACTTACGACGCCCTGCACATGCAGGCAC

TCCCCCCCAGGTGA (J04132.1)

The present invention concerns also a vector comprising the nucleotide sequence as described above, wherein said vector is a DNA vector, a RNA vector, a plasmid, a lentivirus vector, adenoviral vector, retrovirus vector or non viral vector.

In addition, the present invention concerns a cell, such as T cell, such as alfa/beta and gamma/delta T cell, NK cells, NK-T cells, comprising the vector or plasmid mentioned above.

According to an embodiment of the present invention, the above mentioned cell is obtained in the presence of recombinant human IL-2, or with a combination of recombinant IL-7 and IL15. For example, said interleukins can be present in at least one or all of the steps of the process of preparation of the cell such as activation, transduction and expansion.

The present invention concerns also a pharmaceutical composition comprising the nucleotide sequence, or the vector, or the cell, all of them mentioned above, together with one or more pharmaceutically acceptable excipients and/or adjuvants.

It is a further object of the present invention, the CD30 chimeric antigen receptor molecule, the nucleotide sequence, the vector, the cell, the pharmaceutical composition, all of them mentioned above, for medical use.

It is a further object of the present invention the CD30 chimeric antigen receptor molecule, the nucleotide sequence, the vector, the cell, the pharmaceutical composition, all of them mentioned above, for use in the treatment of CD30+ cancers, for example at diagnosis or refractory/relapsed disease, such as lymphoma, such as Hodgkin and non-Hodgkin lymphomas, solid tumors such as myofibroblastic sarcoma, rhabdoid, histiocytic sarcoma, embryonal carcinoma, adenocarcinoma, mesothelioma, mixed germ cell tumors (GCT), non-seminomas GCT, head and neck carcinoma, yolk sac tumor, angiosarcoma, pituitary adenoma, dysgerminoma, teratoma or seminomas. Moreover the present invention can be used also to treat CD30+ PDL1+ tumor (L428-PDL1) as shown by potency assay in FIG. 7D.

In addition, the present invention concerns also a process for the preparation of a cell as defined above, wherein at least one or all the steps of activation (such as with immobilized OKT3 and anti-CD28 antibodies), transduction and expansion of said cell, such as T lymphocyte, are carried out in the presence of recombinant human IL-2, or with a combination of recombinant IL-7 and IL15.

BRIEF DESCRIPTION OF THE DRAWINGS

The present invention is described by an illustrative, but not limitative way, according to preferred embodiments thereof, with particular reference to the enclosed drawings, wherein.

Basal exhaustion profile of CD3 T cells representative of 4 HDs, either NT (white bar), 28.4-1BB.ζ (white bar with horizontal lines) or 28.OX40ζ (black bar) expanded for 15 days in the presence of either IL2 (left side); or in IL7/IL15, (white bar with vertical lines for NT; squared white bar for CARGD2.28-41BBζ T cells and chequered bar for CARCD30.28-OX40ζ T cells respectively). The circle around the asterisk(s) indicates the p-value for comparison between the same population of T cells cultured in presence of either IL7/IL15 or IL2. Data from four HDs are expressed as average±SD. *p-value=<0.05; **p-value=<0.01.

Figure 3:
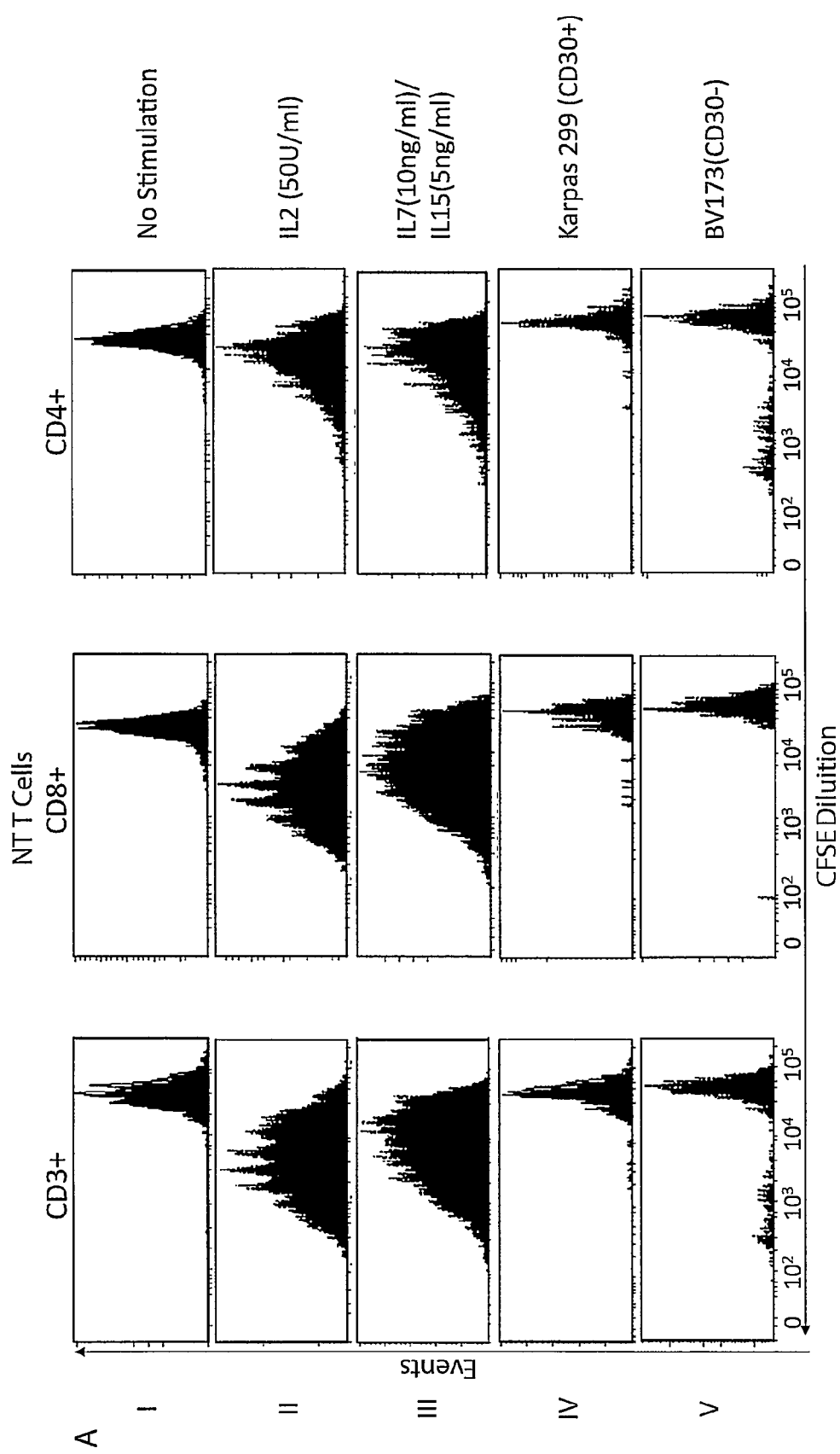
Figure 3:
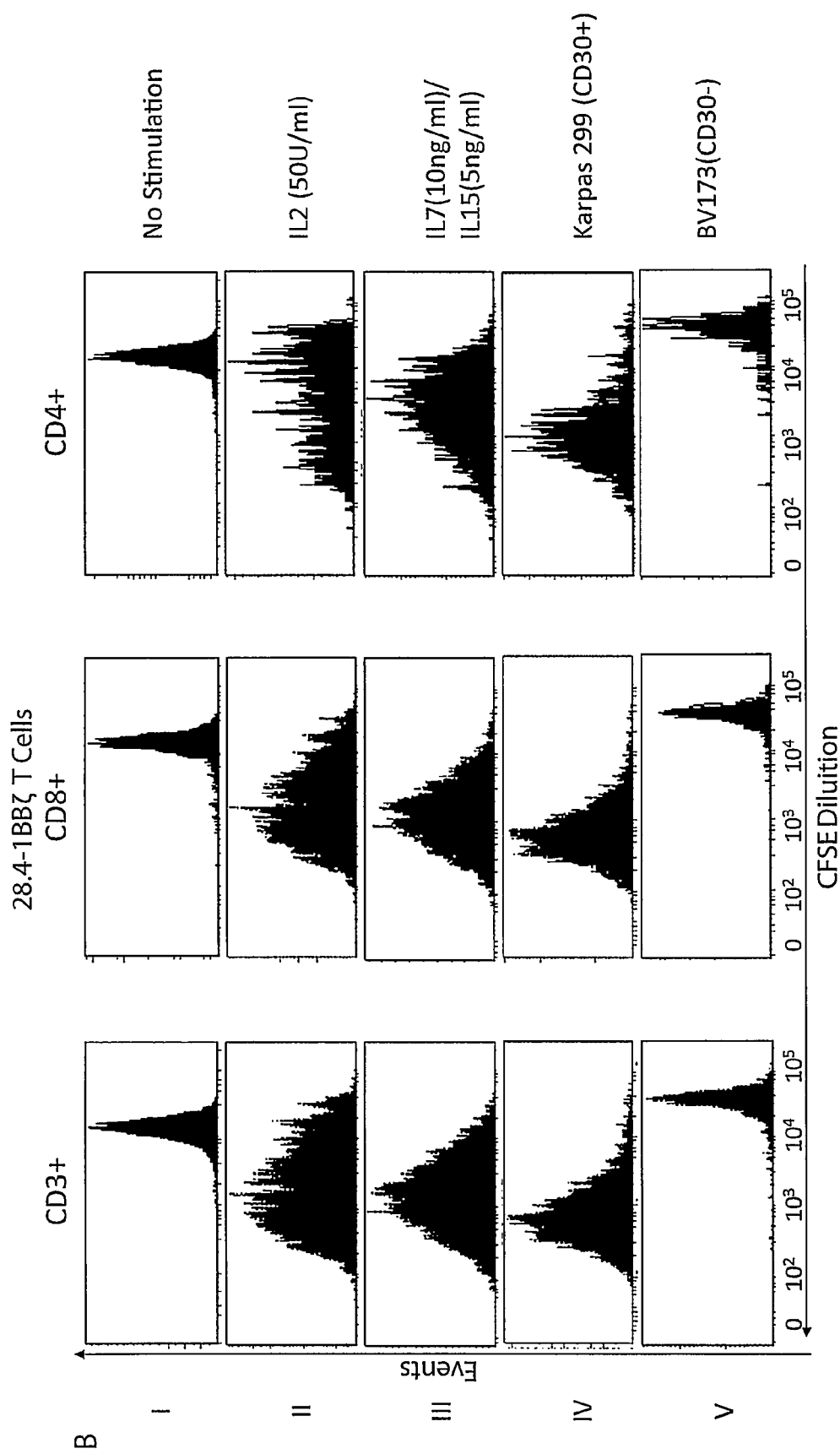
Figure 3:
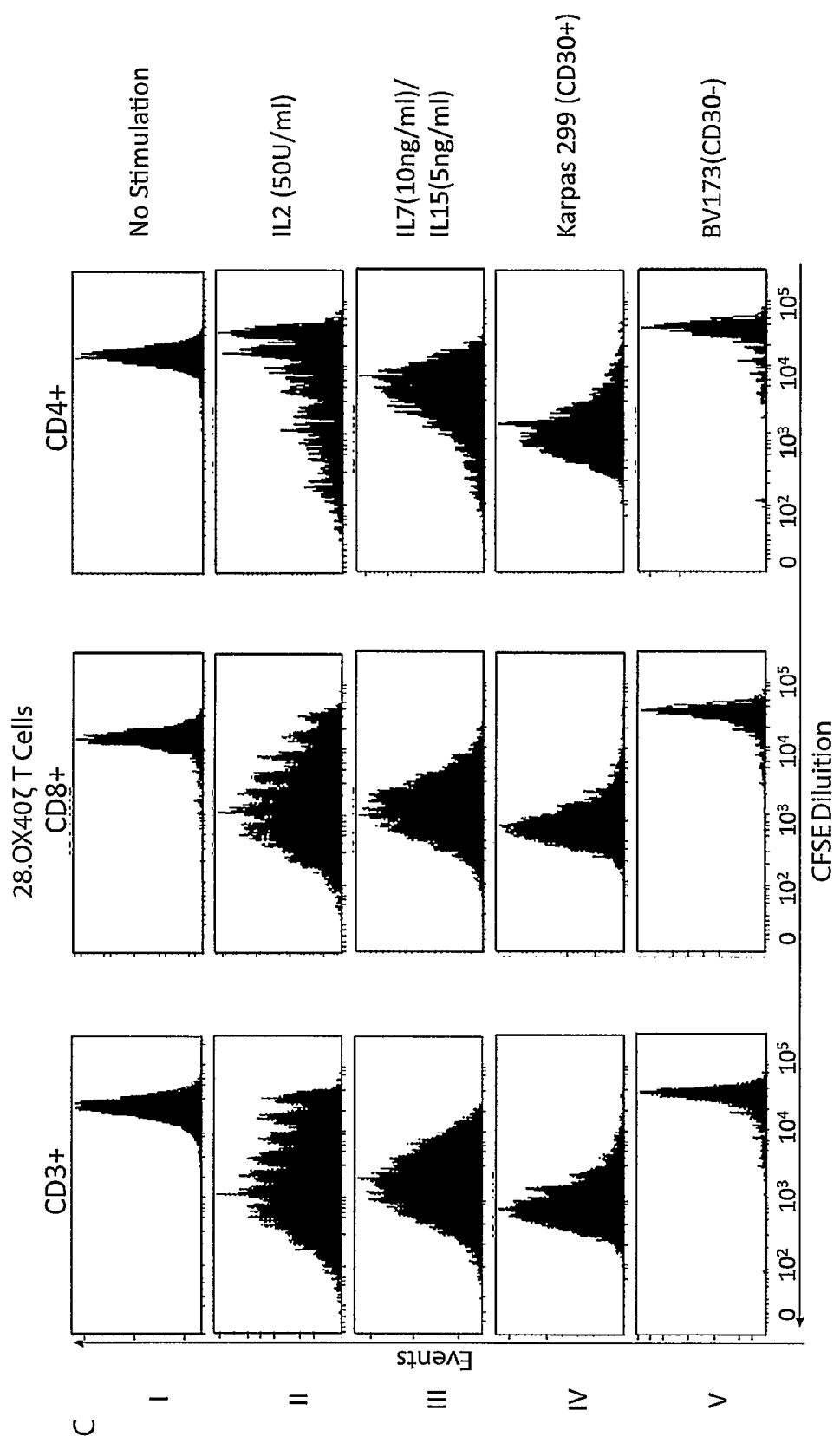

FIG. 3. Basal and/or induced proliferation of NT or CAR-CD30 T cells.

To evaluate the influence of retroviral modification or culture condition on safety profile of modified T cells, for NT (A) or CAR-CD30 T cells (B-C) the basal proliferation or cytokine or/and antigen specific proliferation were evaluated. T cells were labeled at day zero with the fluorescent cell staining CFSE and plated for five days with/out cytokines, or co-cultured in the presence of tumor cell line CD30 positive (Karpas299) or tumor cell line CD30 negative (BV173). The basal or induced proliferation (measured by CFSE dye dilution) of CD3+ (left side), CD8+ (right side) and CD4+ T cells (left side) has been evaluated by FACS analysis.

Figure 4:
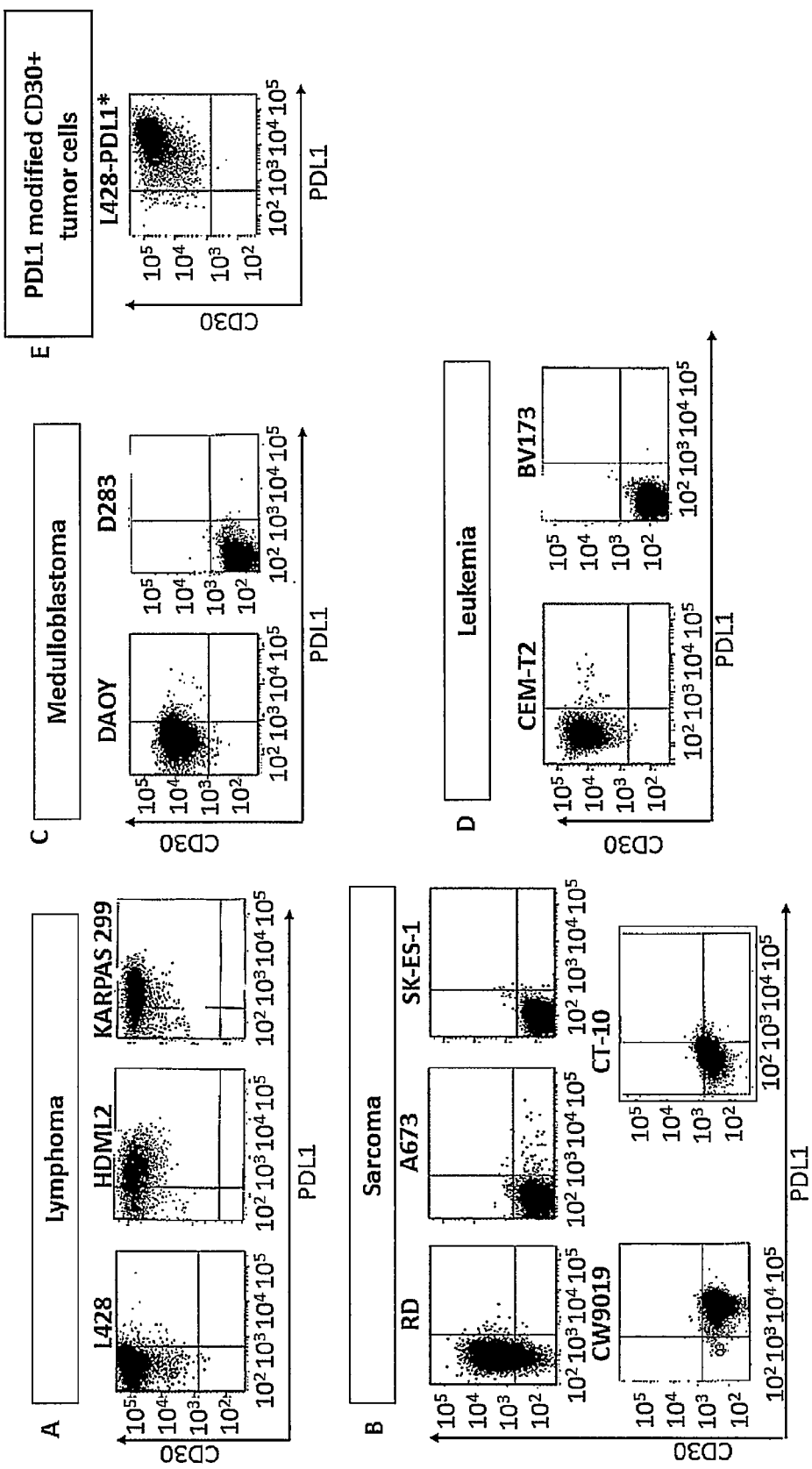

FIG. 4. CD30 and/or PDL1 Expression in solid and hematological tumors cell lines. (A-D) Representative FACS analysis of the constitutive expression of CD30+ and/or PDL1 in three Lymphoma cell lines: L428, HDML2 and Karpas 299 (A), in five-sarcoma cell lines: RD, A673, SK-ES-1, CW9019 and CT-10 (B), in two medulloblastoma cell lines: DAOY and D283 (C), and in two leukemia cell lines: CEM-T2 and BV-173 (D). Last picture show the FACS analysis of lymphoma cell line L428 genetically modified with retroviral vector SFG containing the cassette PDL1, to obtain L428-PDL1 lymphoma cell line (E).

Figure 5:
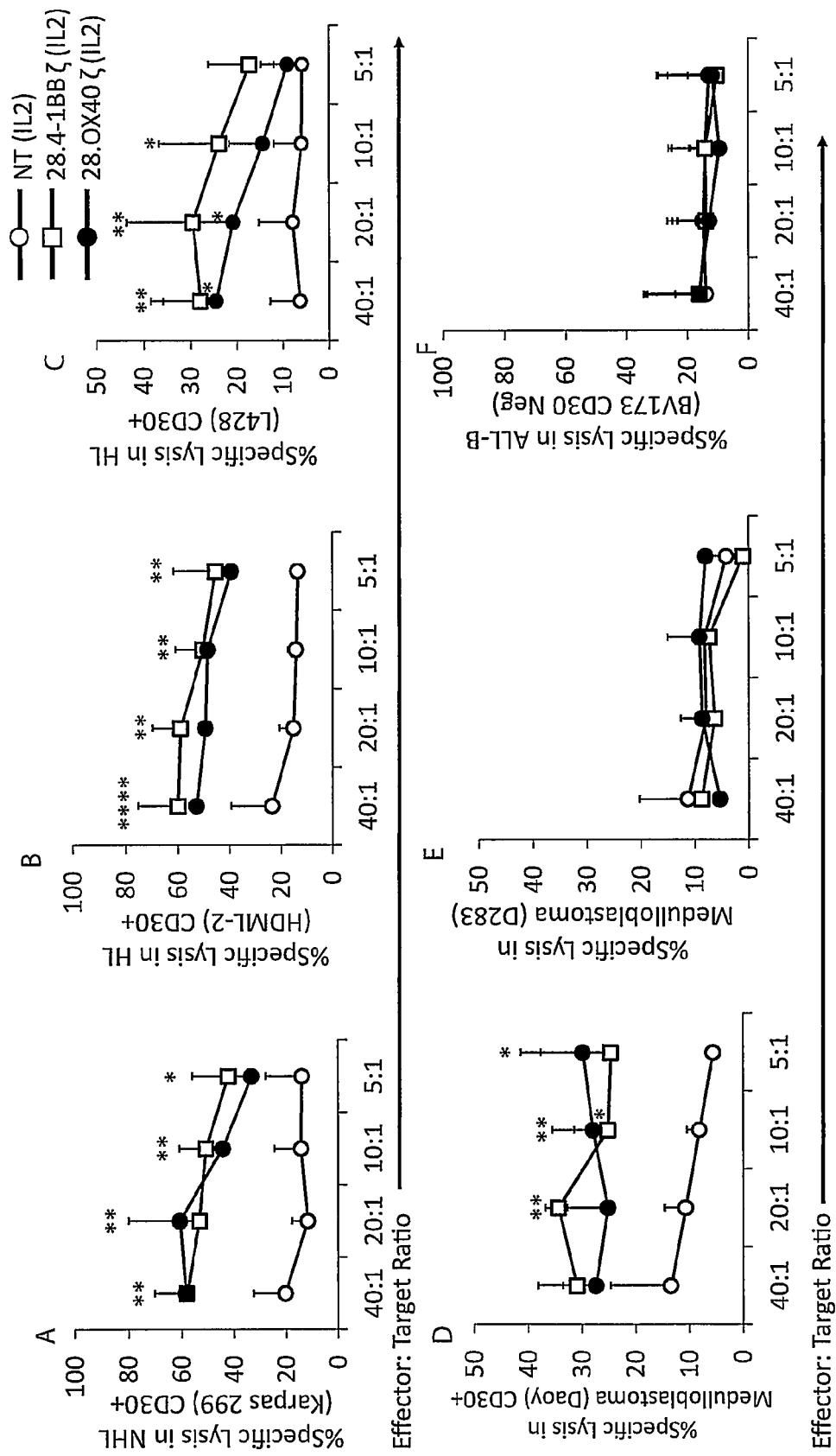

FIG. 5. CAR-CD30 T cells growth in complete CTL media with IL2, and transduced with 28.4-1BB or 28.OX40 costimulation domains, show comparable short-term cytotoxic effect in vitro experiment. In vitro $^{51}$Cr release assay evaluating cytolytic activity of NT T cells (line with white circle), 28.4-1BB.ζ T cells (line with white square) or 28.OX40.ζ T cells (line with black circle), on CD30+ lymphoma (Karpas 299 cell line (A), HDML-2 cell line (B) and L428 cell line (C)) on CD30+ medulloblastoma DAOY (D), and in CD30 negatives as the medulloblastoma D283 (E) and the lymphoma BV173 (F). Assays were performed 15 days after initial activation and expansion in the presence of IL2. Data from six healthy donors (HDs) are expressed as average±SD. *p-value≤0.05; p-value≤0.01; *p-value≤0.001 and ****0.0001.

Figure 6:
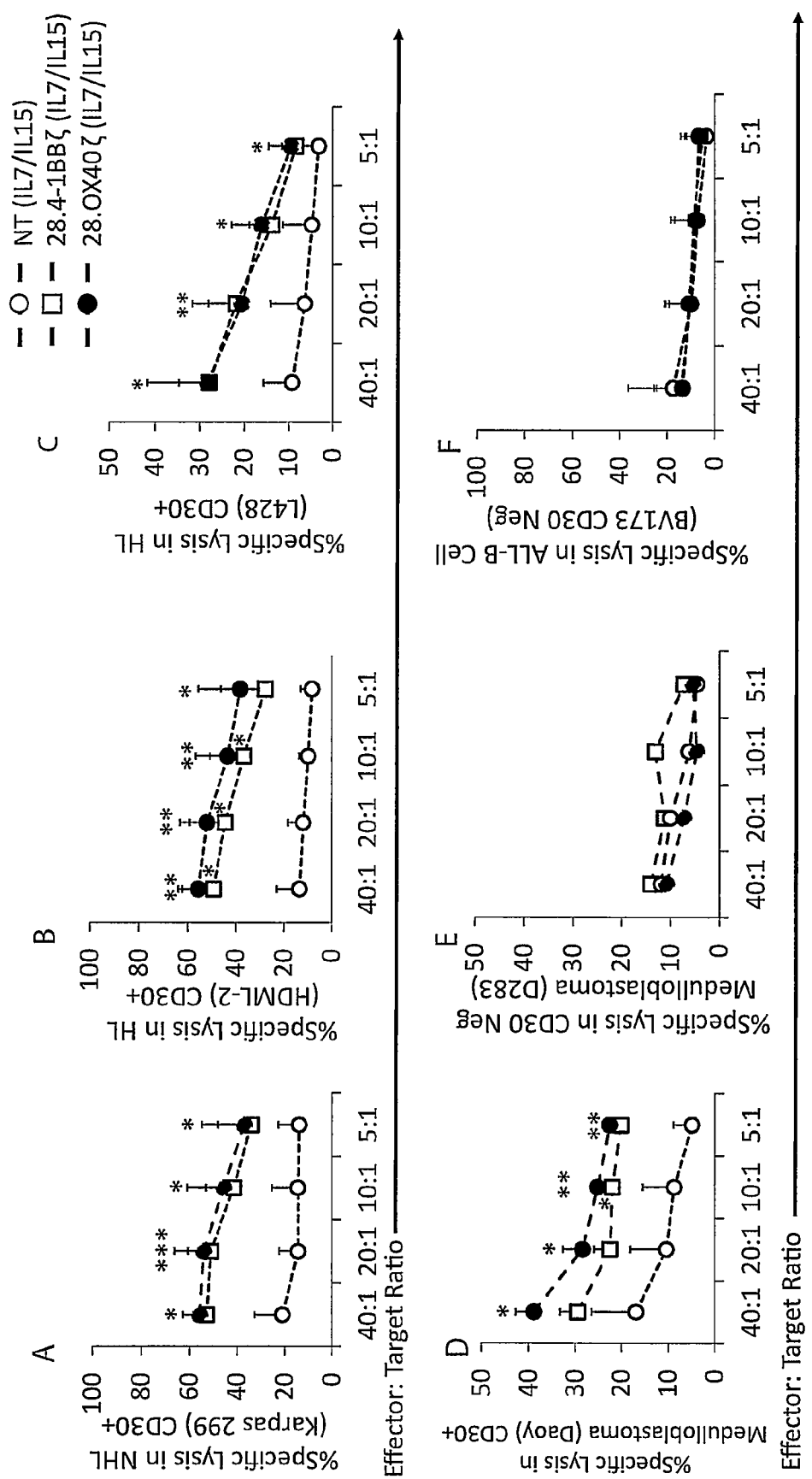

FIG. 6. CAR-CD30 T cells growth in complete CTL media with IL7/IL15, and transduced with 28.4-1BB or 28.OX40 costimulation domains, show comparable short-term cytotoxic effect in vitro experiment. In vitro $^{51}$Cr release assay evaluating cytolytic activity of NT T cells (dotted line with white circle), 28.4-1BB.ζ T cells (dotted line with white square) and 28.OX40.ζ T cells (dotted line with black circle), on CD30+ lymphoma (Karpas 299 cell line (A), HDML-2 cell line (B) and L428 cell line (C)) on CD30+ medulloblastoma DAOY (D), and in CD30 negatives as the medulloblastoma D283 (E) and the lymphoma BV173 (F). Assays were performed 15 days after initial activation and expansion in the presence of IL7/IL15. Data from six healthy donors (HDs) are expressed as average±SD. *p-value≤0.05; p-value≤0.01; *p-value≤0.001 and ****0.0001.

Figure 7:
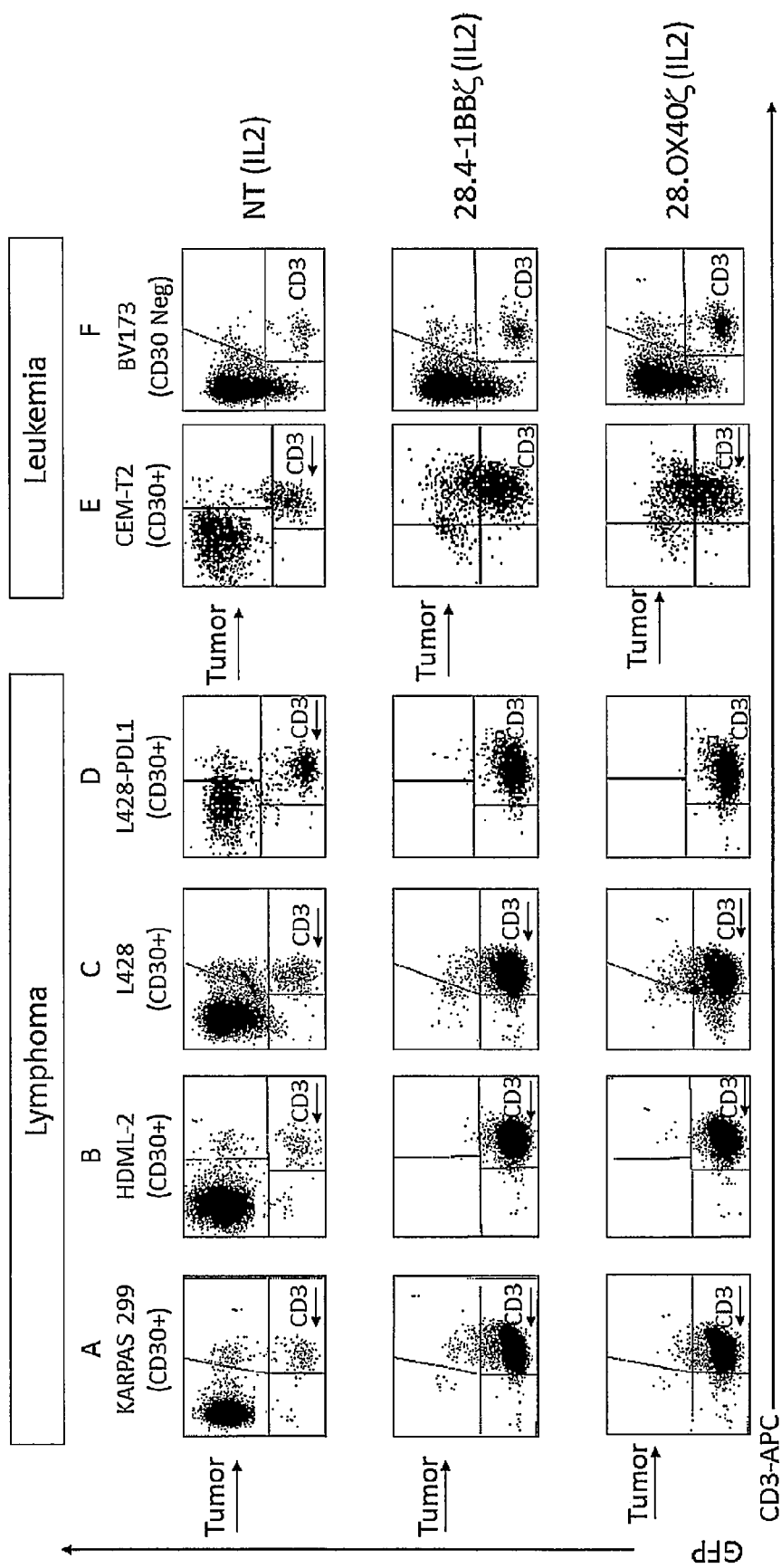
Figure 7:
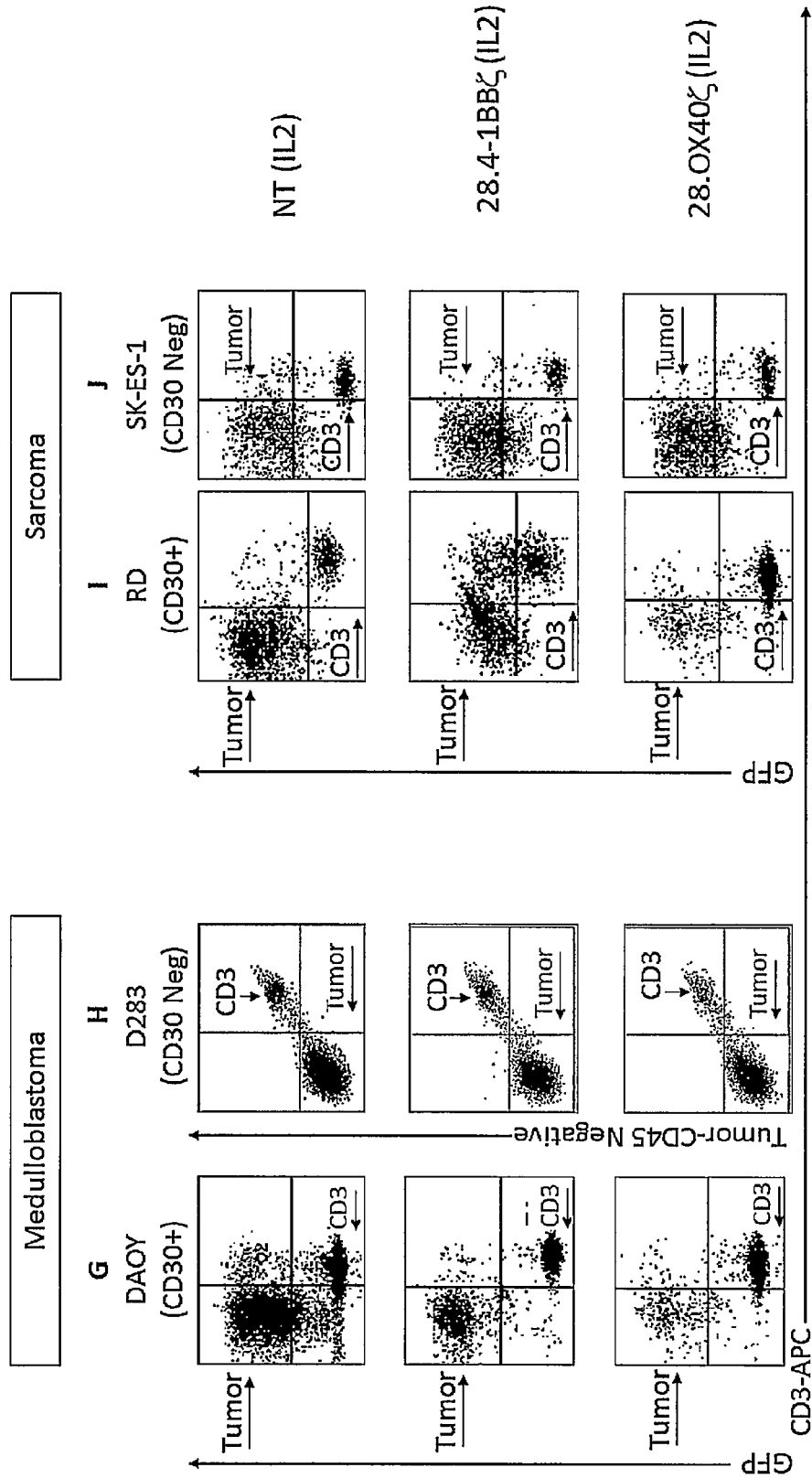
Figure 7:
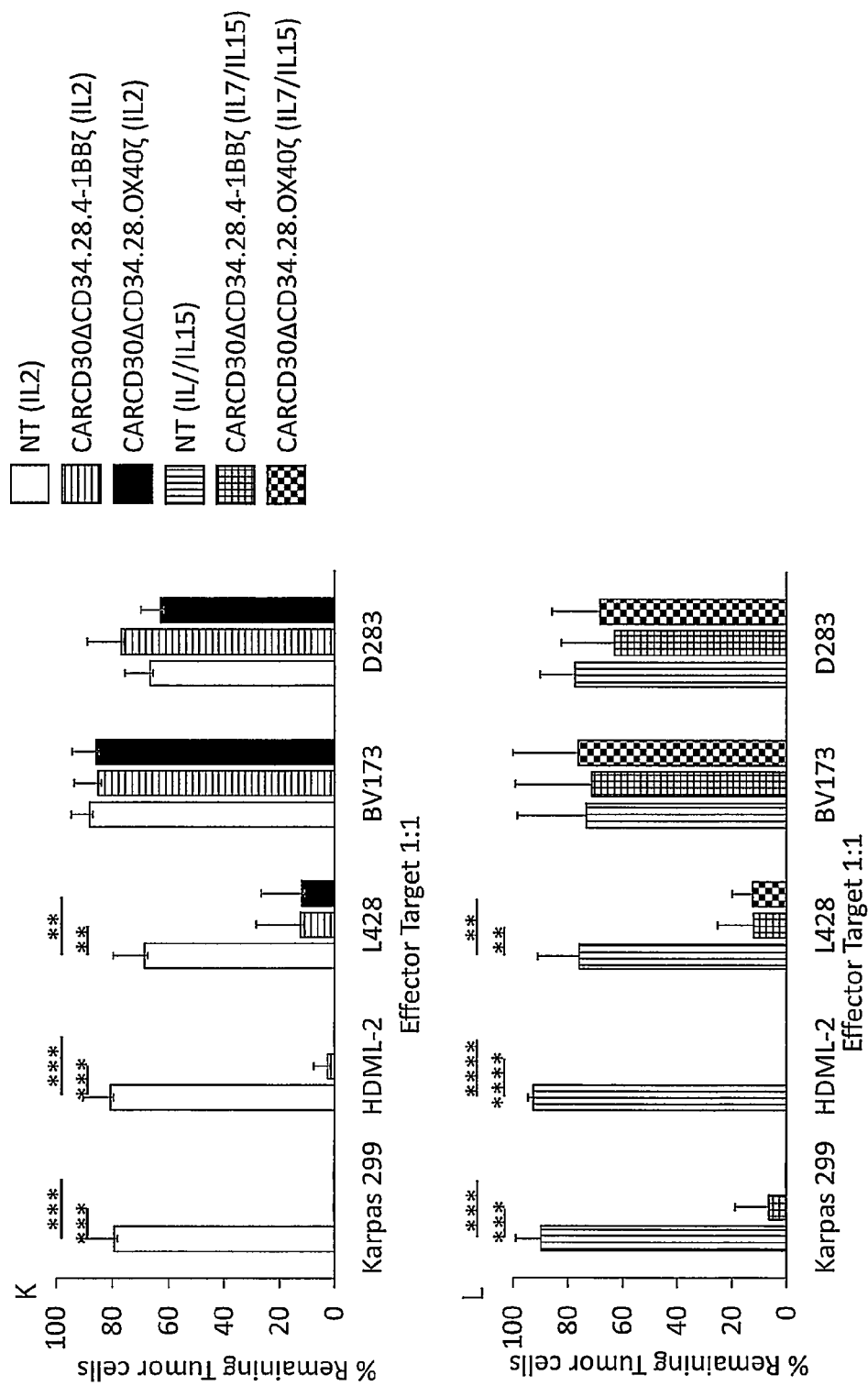

FIG. 7. Long-term co-culture of both CAR-CD30 T cells against CD30+ tumor cell lines confirm their equal specific cytotoxic potency, independently of cytokines used. (A-J) Representative FACS analysis of residual tumor cells (identified as GFP+ cells) (or CD45-CD3- for D283 cells) after 7 days-coculture at the ratio E/T 1:1 with effector NT cells (top panels), CD30-CAR T cells: 28.4-1BBζ T cells (middle panel) and 28-OX40ζ T cells (lower panels).

(K-L) Average representation of remaining tumor cells, after 7 days-coculture at the ratio E/T 1:1 with NT (white bar), CARGD2.28-41Bζ T cells (white bar with horizontal lines), and CARCD30.28-OX40ζ T cells (black bar) growth in IL2 (K) or in IL7/IL15, (white bar with vertical lines for NT; squared white bar for CARGD2.28-41Bζ T cells and chequered bar for CARCD30.28-OX40ζ T cells respectively) (L). Data from six healthy donors (HDs) are expressed as average±SD. *p-value≤0.05; p-value≤0.01; *p-value≤0.001 and ****≤0.0001.

Figure 8:
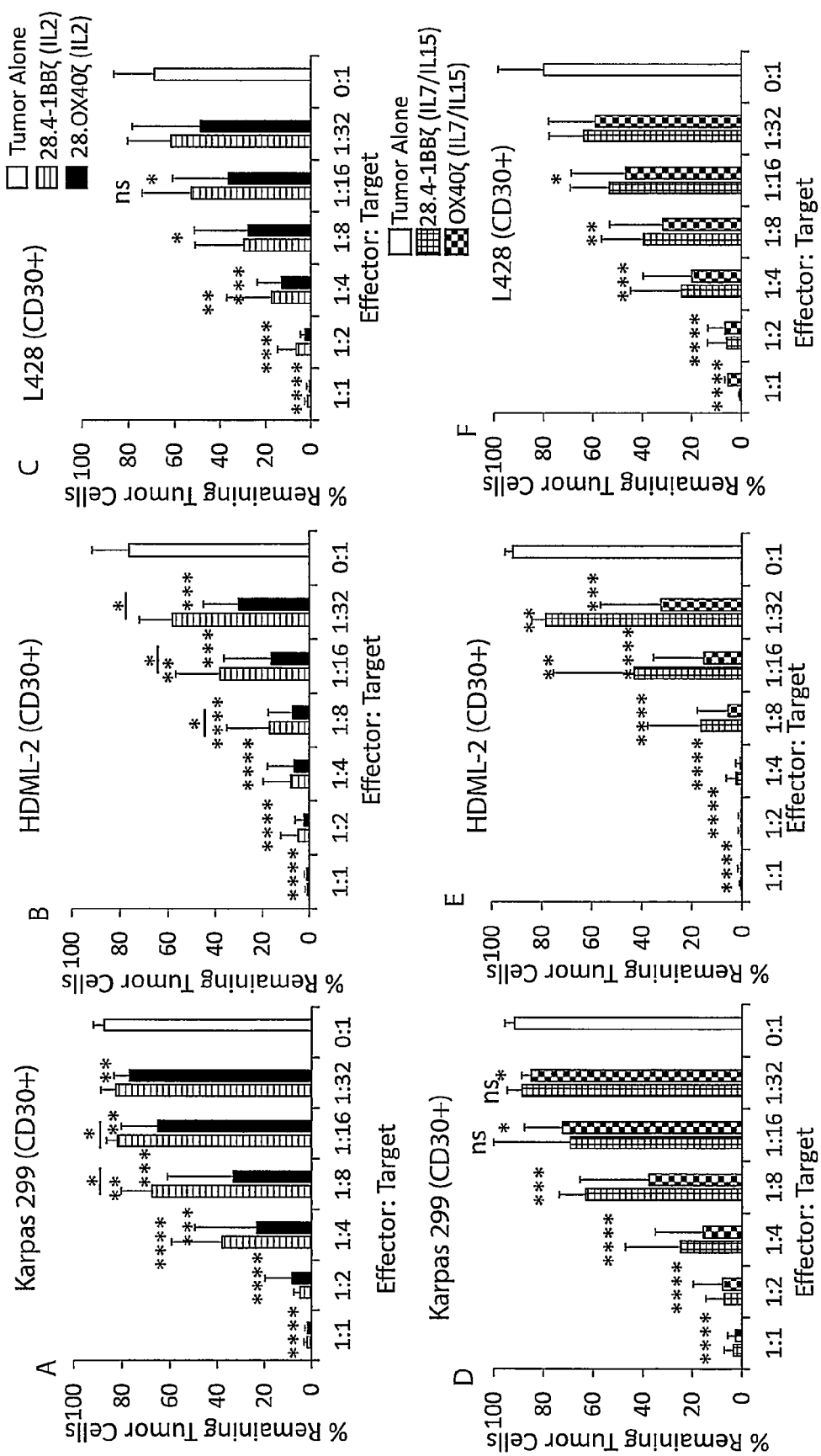

FIG. 8. Stressed long-term co-culture to evaluate and to quantify the functional activities of CAR-CD30 T cells. (A-F) Evaluation of efficiency tumor control of lymphoma tumor cell, after 7 days-coculture at low E/T ratio with CARGD2.28-41Bζ T cells (bar graph with horizontal lines), or CARCD30.28-OX40ζ T cells (black bar) growth in IL2 (A-C); or in IL7/IL15, (squared bar for CARGD2.28-41Bζ T cells or chequered-bar for CARCD30.28-OX40ζ T cells respectively) (D-F). Tumor alone is indicated by white bar Data from six healthy donors (HDs) are expressed as average±SD. *p-value≤0.05; p-value≤0.01; *p-value≤0.001 and ****0.0001.

Figure 9:
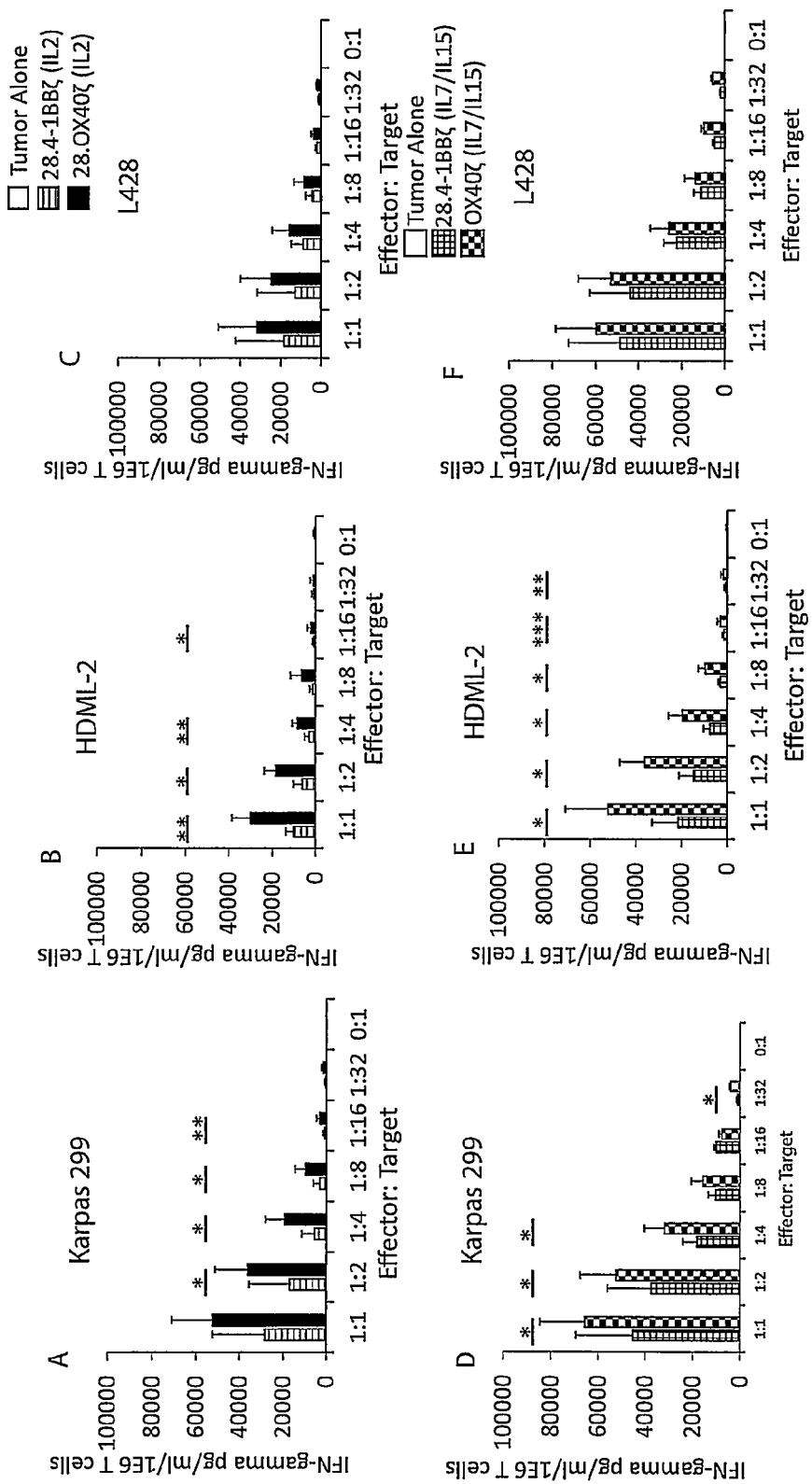

FIG. 9. IFN-gamma profile of CAR-CD30 T cells co-cultured with CD30+ tumors cells. (A-F) Specific IFN-gamma production after 24 h of Effector:Target co-culture. The diagram shows IFN-gamma production of CAR.CD30 T cells growth in IL2 (A-C) or in IL7/IL15, (D-F), after stimulation by tumor Lymphoma cell lines. CARCD30.28-OX40ζ T cells co-cultured 24 h with Karpas 299 (A and D) or HDML-2 (B and E) produce a significantly higher level of IFN-gamma respect to CARGD2.28-41Bζ T cells, in particular a lower ratio Effector: Target. When the CAR-CD30 T cells were co-cultured with the tumor cell line L428, no difference was observed between two CARs (C and F). CARCD30.28-OX40ζ T cells growth also in IL7/IL15 produce higher level the IFN-gamma, when co-cultured with the CD30+ tumours cells (D-E), except when co-cultured with L428 tumor cell line (F).

Figure 10:
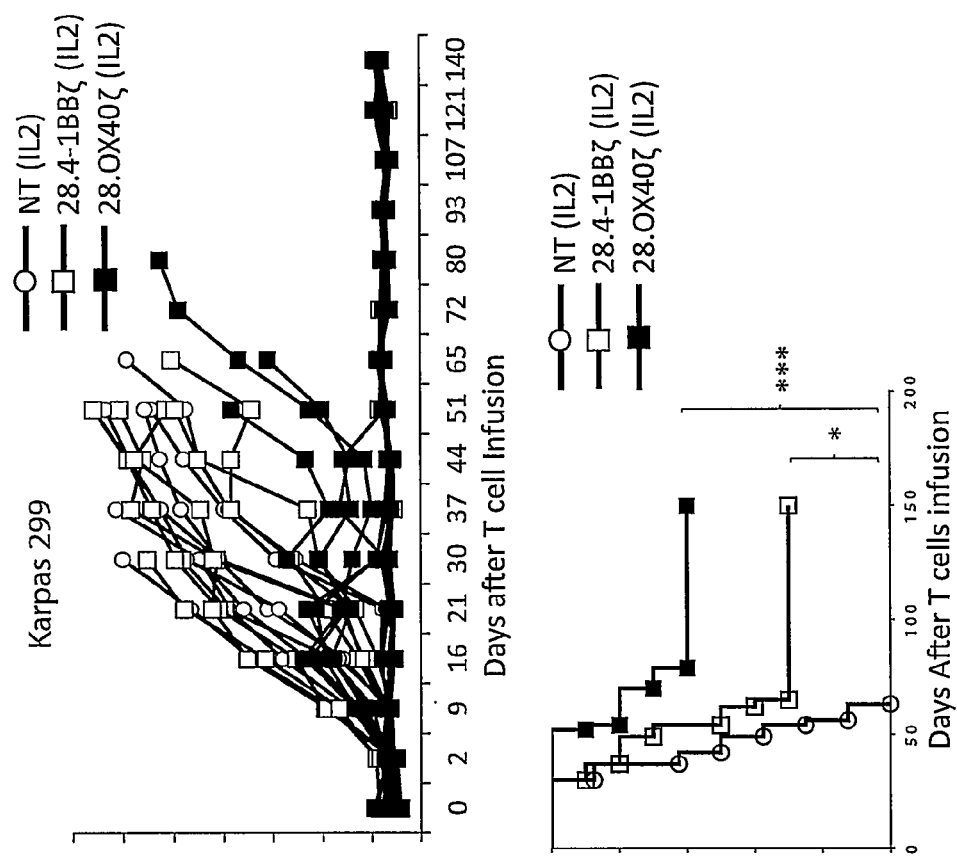
Figure 10:
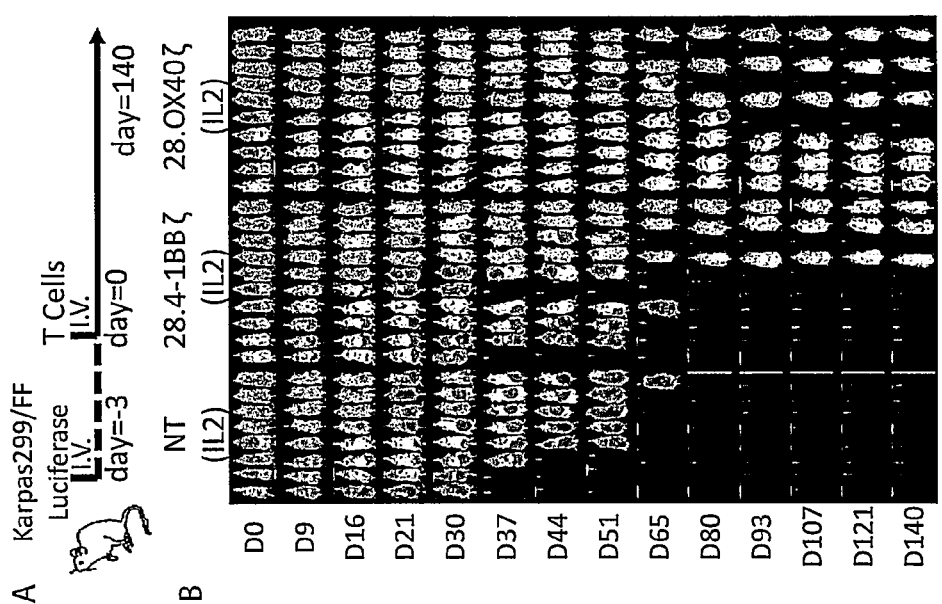

FIG. 10. In vivo activity of CAR.CD30 T cells generated and expanded in the presence of IL2 against the NHL Karpas 299. (A-C) In vivo bioluminescence imaging of NSG mice bearing sistemic Karpas 299-FF-Luc.GFP cells and treated with NT, CARCD30.28.4-1BBζ or CARCD30.28.OX40ζ T cells generated and expanded in the presence of IL2. (A) Schematic model of in vivo experiments. Mice receive i.v. Karpas 299-FF-Luc.GFP cells. After three days when the bioluminescence of the tumor became stable they are divided in three cohort and treated with NT or one of two CAR-CD30 T Cells. The tumors growth was evaluated by IVIS evaluation every weeks for 140 days. (B) Bioluminiscence imaging of tumor growth measured weekly in three cohort of mice; (C) representation of bioluminescence of each single mouse treated with NT (IL2) (lines with white circle; 8 mice), 28.4-1BBQ (IL2) (lines with white square; 10 mice) and 28.OX40ζ (IL2) T cells (lines with black square; 10 mice). (D) Kaplan-Meier overall survival (OS) analysis of tumor-bearing mice treated with NT (IL2) (lines with white circle; 8 mice), 28.4-1BBQ (IL2) (lines with white square; 10 mice) and 28.OX40ζ (IL2) T cells (lines with black square; 10 mice). *P-value=<0.05; P-value=<0.001; *P-value=<0.0001. Log-rank (Mantel-Cox).

Figure 11:
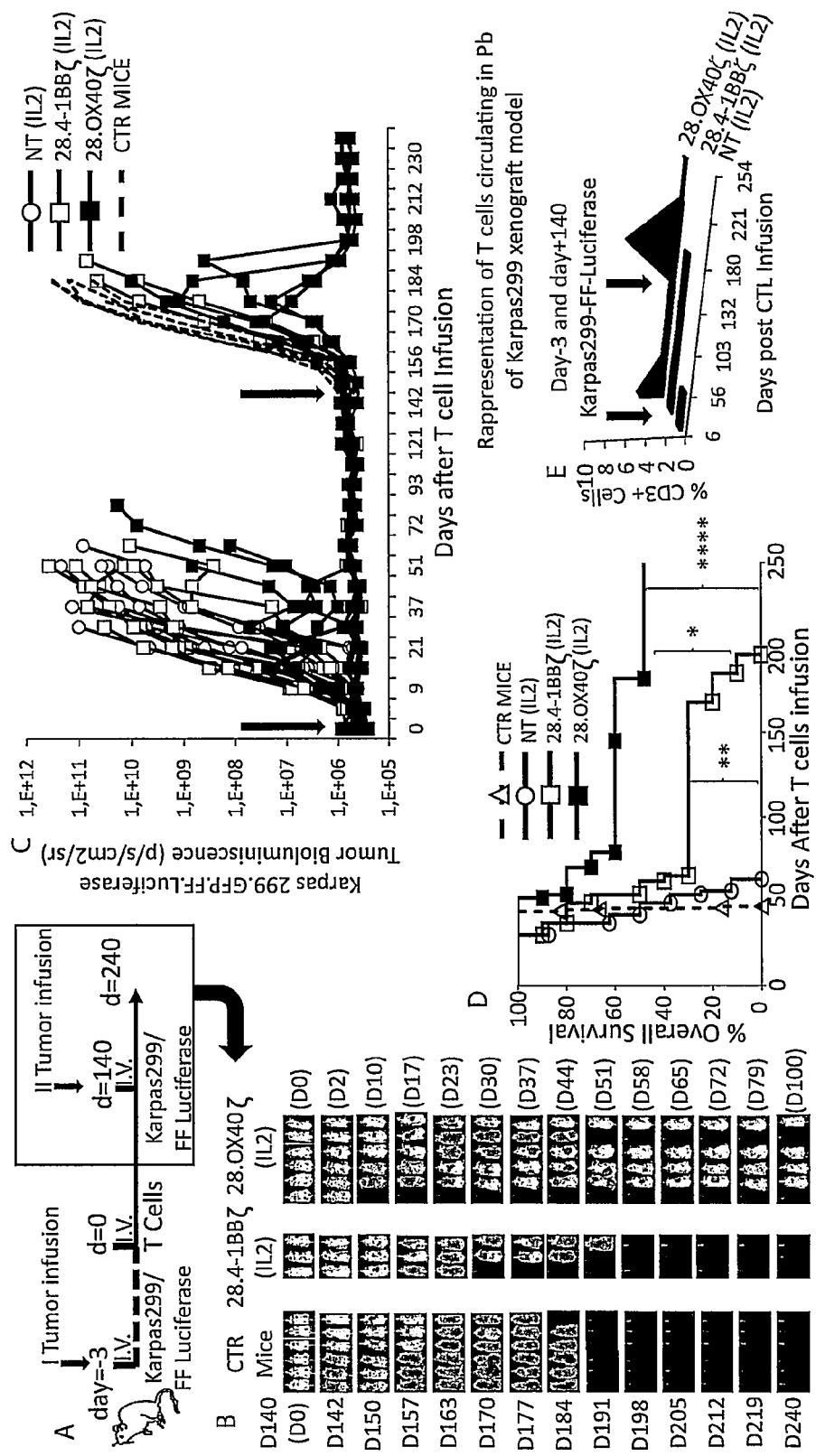

FIG. 11. Re-Challenging model: The establishment of long-term immunological memory in NHL mice model. (A-C) In vivo bioluminescence imaging of cured NSG mice re-challenged at day +140 i.v. with $0.2 \times 10^6$ Karpas 299-FF-Luc.GFP cells, and followed for other 100 days. (A) Schematic model of in vivo experiments. Mice received i.v. Karpas 299-FF-Luc.GFP cells two times: at day 0 and at day 140. At days 3 when the bioluminescence became stable, they are divided in three cohort and treated with NT or one of two CAR-CD30 T Cells. The tumor growth was evaluated by IVIS evaluation every weeks for 240 days. At day 140 cured mice and a new cohort of mice (added to the experiment as positive control (CTR Mice) of the engraftment of the tumor) were re-challenged i.v. with Karpas 299-FF-Luc.GFP cells.

(B) Bioluminiscence imaging of tumor growth measured weekly from day 140 until day 240. (C) Representation of bioluminescence of each single mouse treated with NT (lines with white circle; 8 mice), CARCD30.28.4-1BBζ (lines with white square; 10 mice) and CARCD30.28.OX40Bζ T cells (lines with black square; 10 mice) and CTR mice added to the experiment at day 140 as positive control of the engraftment of second tumor (dotted lines; 6 mice). (D) Kaplan-Meier overall survival (OS) analysis of tumor-bearing mice treated only one time at day +3 with NT (lines with white circle; 8 mice), CARCD30.28.4-1BBζ (lines with white square; 10 mice) and CARCD30.28-OX40ζ T cells (lines with black square; 10 mice) and re-challenged with the second tumor at day +140. Days of survival of CTR mice (dotted lines with white triangle; 6 mice) were added considering day 140 as zero. *P-value=<0.05; P-value=<0.01; *P-value=<0.001; ****P-value=<0.0001. Log-rank (Mantel-Cox). (E) Representative picture of circulating human T cells bleed at day indicated, after challenging with the first tumor (day +6) and before and after re-challenging of the second tumor (day 132 and 180 respectively). NT (first line), CARCD30.28-41Bζ T cells (second line) and CARCD30.28-OX40ζ (third line).

Figure 12:
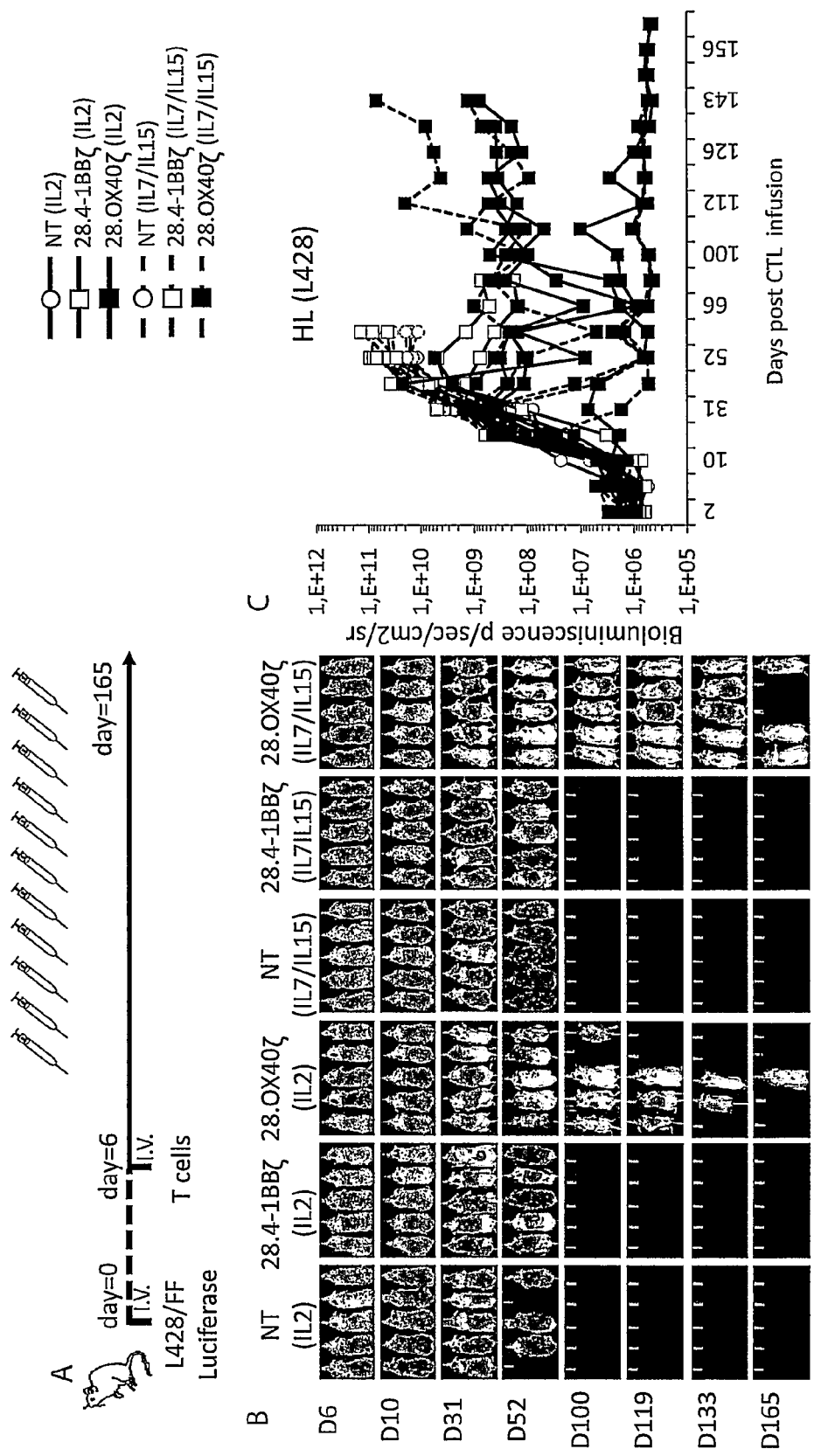
Figure 12:
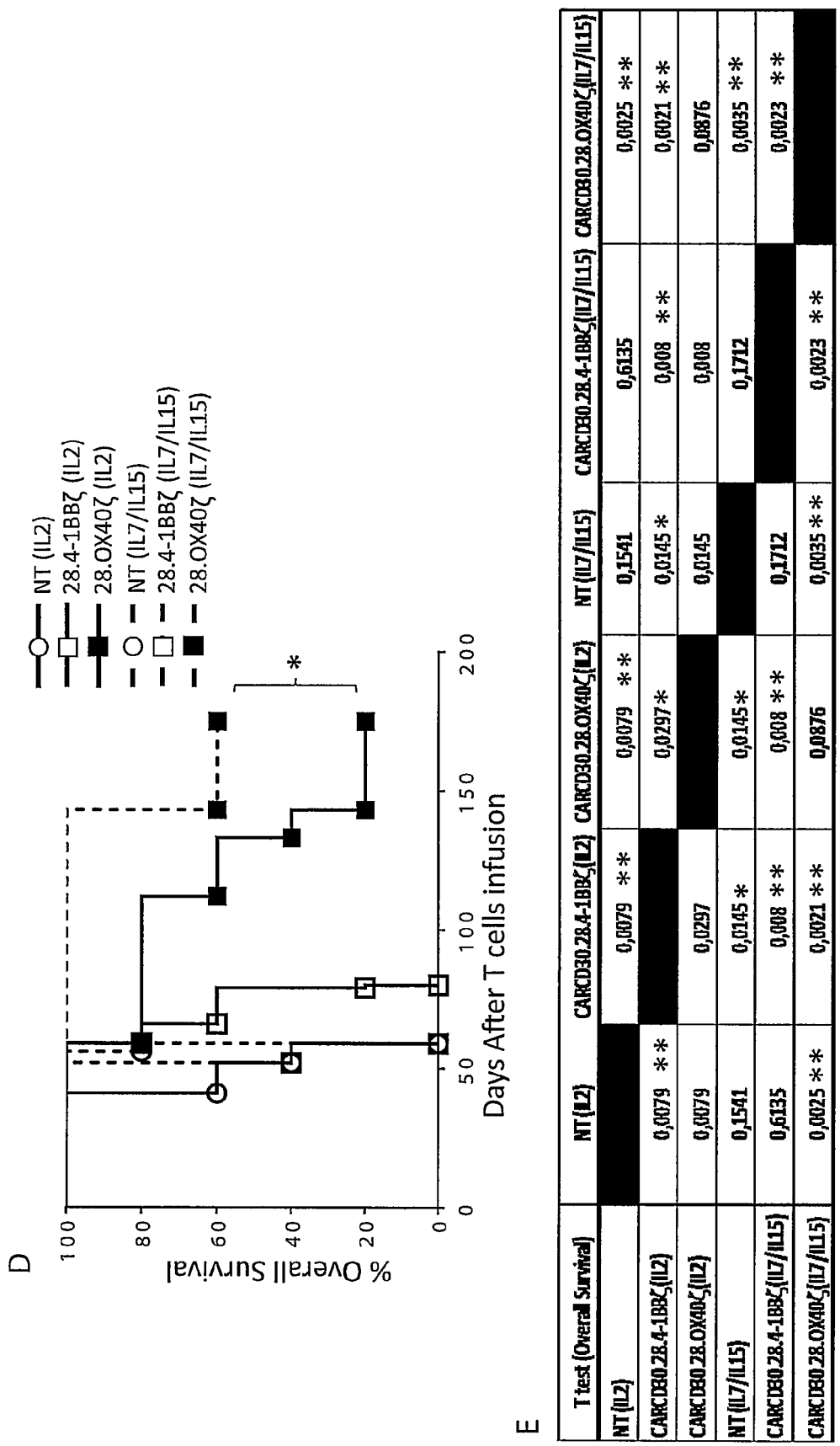
Figure 12:
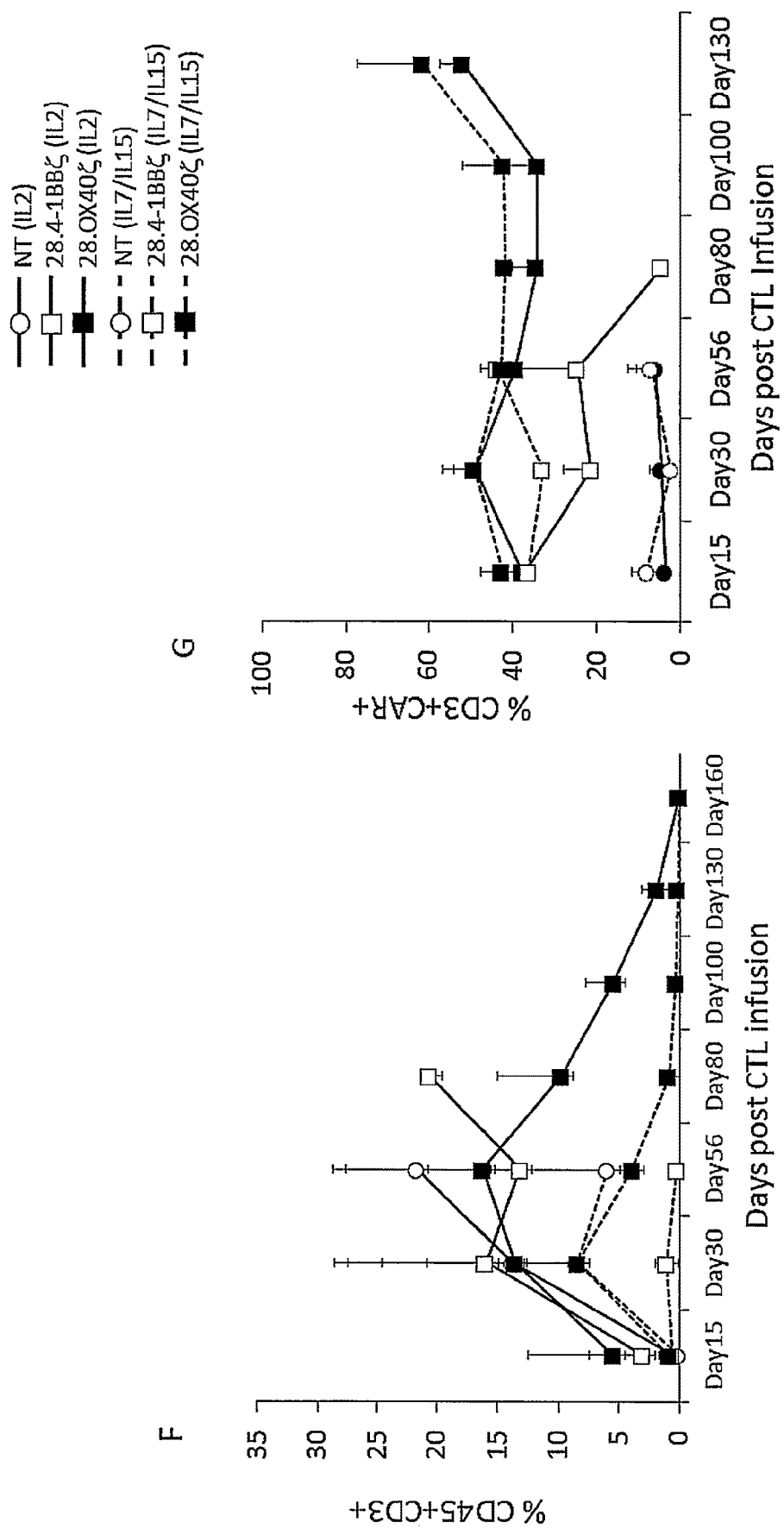

FIG. 12. Evaluation of in vivo activity of CAR.CD30 T cells generated and expanded in the presence of IL2 or IL7/IL15 against the HL L428. (A-C) In vivo bioluminescence imaging of NSG mice bearing systemic L428-FF-Luc.GFP cells treated at day 6 with NT, 28.OX40ζ or 28.4-1BBζ T cells generated and expanded in vitro in the presence of IL2 or IL7/IL15. The tumor growth was evaluated by IVIS evaluation every weeks for 165 days. (A) Schematic model of in vivo experiments. Mice received i.v. $2 \times 10^6$ L428-FF-Luc.GFP cells and after 6 days, when the bioluminescence became stable, they were divided in six cohort and treated with NT or CAR-CD30 T Cells. The tumor growth was evaluated by IVIS evaluation every weeks for 165 days. (B) Bioluminescence imaging of tumor growth measured weekly from day 6 until day 165. (C) Bioluminescence of each single xenograft mouse treated with NT(IL2) T cells (lines with white circle; 5 mice); 28.4-1BBζ(IL2) T cells (lines with white square; 5 mice); 28.OX40ζ(IL2) T cells (lines with black square; 5 mice); NT(IL7/IL15) T cells (dotted lines with white circle; 5 mice); 28.4-1BBζ(IL7/IL15) T cells (dotted lines with white square; 5 mice) and 28.OX40ζ(IL7/IL15) T cells (dotted lines with black square; 5 mice). (D) Kaplan-Meier overall survival (OS) analysis of tumor-bearing mice treated with NT(IL2) (lines with white circle), 28.4-1BBζ(IL2) (lines with white square) and CARCD30.28-OX40ζ(IL2) (lines with black square); NT (IL7/IL15) (dotted lines with white circle), CARCD30.28.4-1BBζ (IL7/IL15) (dotted lines with white square) and CARCD30.28.OX40ζ (IL7/Il15) (dotted lines with black square); *P-value=<0.05; P-value=<0.001; *P-value=<0.0001. Log-rank (Mantel-Cox). (E) The Table report the significance of OS of L428 xenograft mice treated with NT or CAR-CD30 T Cells growth in IL2 or IL7/IL15. *P-value=<0.05 and **P-value=<0.01. (F-G) Average of human circulating T cells, in NSG mice bearing systemic L428-FF-Luc.GFP tumor cells and treated at day +6 with human NT or CAR.CD30 T cells, evaluated either as percentage CD45+CD3+ cells (F) and either as CAR-CD30 T cells (CD3+CD34+) at days 15, 30, 56, 80, 100, 130 and 160. (G).

Figure 13:
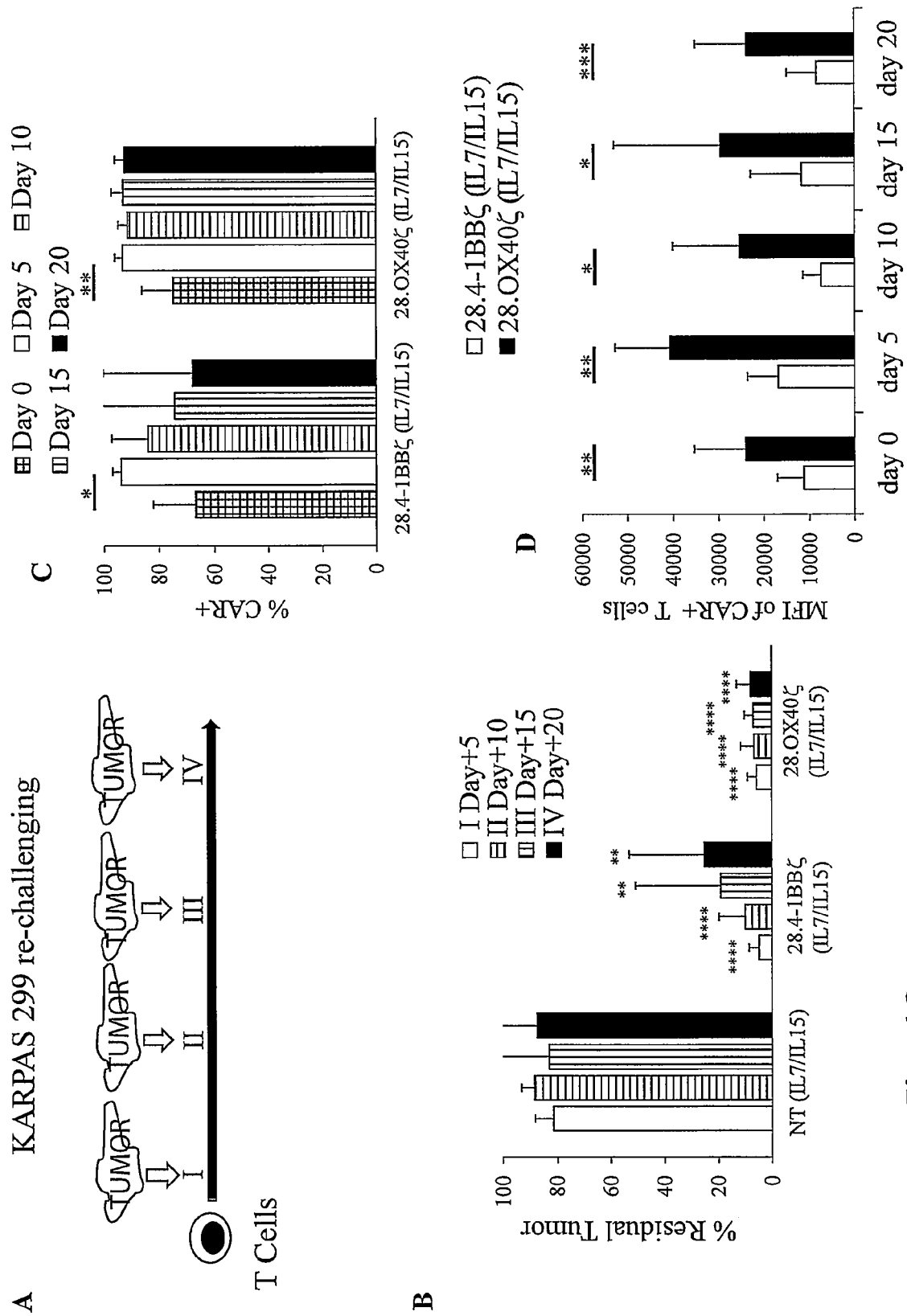
Figure 13:
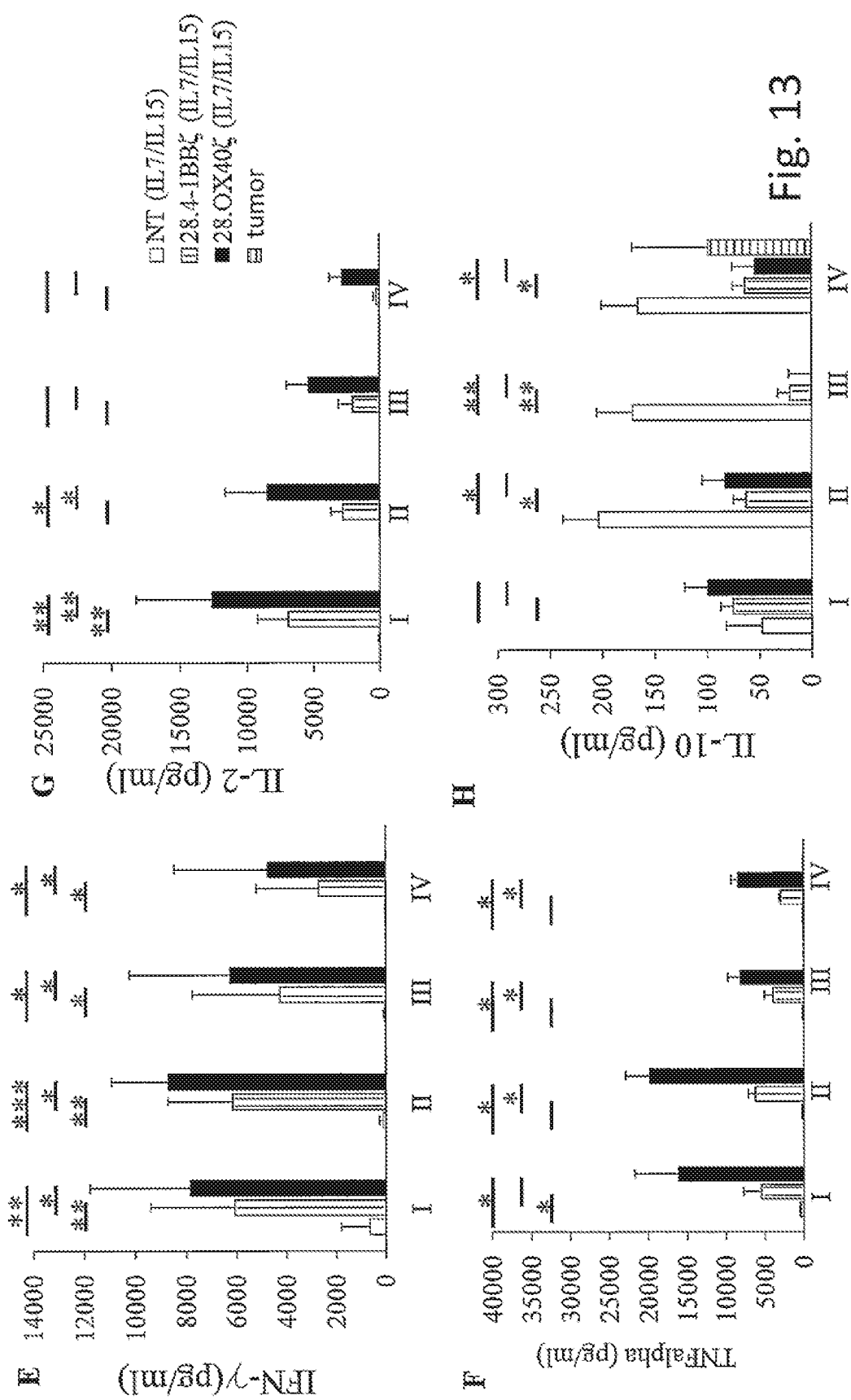
Figure 13:
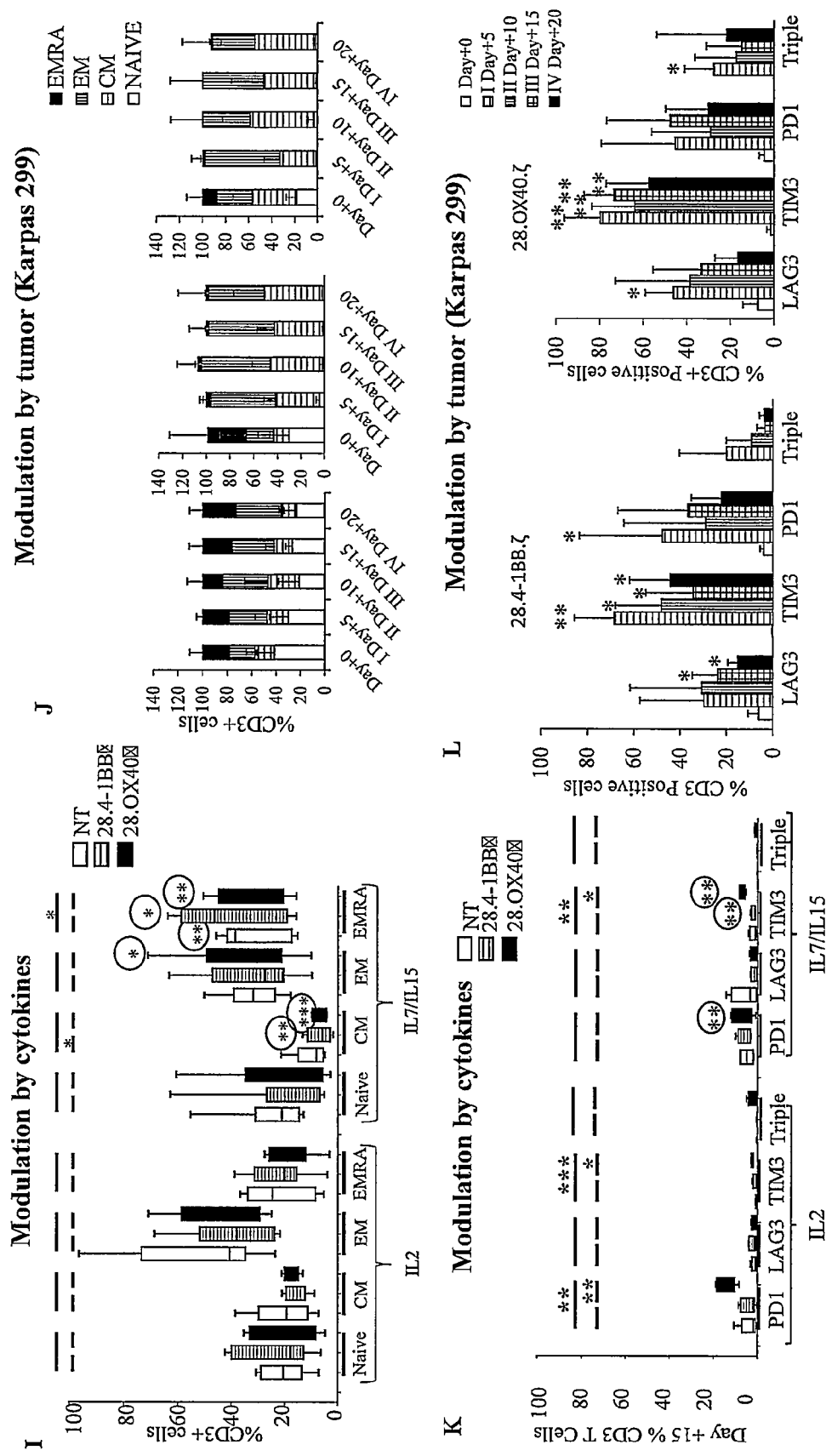

FIG. 13. Stressed long-term co-culture. (A) The experimental design of "stressed co-culture" shown in a cartoon. T cells, at day +15 after transduction, were co-cultured in contact with Karpas 299 tumor cell line at E/T ratio of 1:1 (0.5E+06 of T cells vs 0.5E+06 of Karpas 299 in 24 well plate). Tumor cells were administrated every five days until day 20 of co-culture (1, II, III and IV administration). At each time point, supernatant was collected at 24 hours and analysed for the presence of citokines IFNγ, TNFα, IL-2 and IL-10. After five days of each administration cells were collected and analyzed by FACS. (B) A bar graph showing the percentage of residual tumor in the culture after 5 days of each tumor administration. Both CAR.CD30 T cells controlled tumor growth efficiently. Nevertheless, 28-OX40ζ T cells shown an increased tumor control at day +20. (C) A bar graph showing the percentage of CAR positive T cells on the total of CD3 positive T cells present in the co-culture at each time point. The percentage in both CAR.CD30 molecule significantly increased after the first co-culture, i.e. day +5. The re-challenging of the tumor negatively influenced the level of transduction only for 28.4-1BB.ζ T cells whilst the percentage remained stable in 28.OX40.ζ T cells. (D) The graph underlines significant higher values of MFI in 28.OX40.ζ T cells (black bars) respect to 28.4-1BB.ζ T cells (white bars). (E-H) Cytokine profile obtained from ELLA assay, performed on the supernatants collected after 24 hours by the tumor stimulation. Data from 7 healthy donors (HDs) are expressed as average±SD. *p-value≤0.05; p-value≤0.01; *p-value≤0.001 and ****0.0001. (I): Tumor modulation of Memory and Exhaustion profiles in CAR.CD30 T Cells. Flow cytometry analysis of proportion of Naïve, CM, EM and EMRA subsets at day +15 of in vitro culture of CD3+ T cells either NT (white bar), 28.4.1BB.ζ (horizontal lines bar) or 28.OX40.ζ (black bar), expanded in the presence of IL2 or IL7/IL15 cytokines. (J) Long-term "stressed" co-culture induced a selection of EM and CM compartments in both 28.4-1BB.ζ and 28.OX40.ζ T cells, but not in NT T cells. (K) Exhaustion profile of CD3+ T cells, either NT (white bar), 28.4.1BB.ζ (horizontal lines bar) or 28.OX40.ζ (black bar) expanded for 15 days in IL2 or IL7/15 cytokines. Significance between NT T or CAR-CD30 T cells growths in the same culture condition were reported in black, while the encircled asterisks indicates the p-value for comparison between the same populations of T cells cultured in presence of IL2 or IL7/IL15. (L) Long-term "stressed" co-culture induced an upregulation of the exhaustion markers, especially of PD1 and TIM3, in both types of CAR.CD30 T cells, although the upregulation of these molecules did not interfere with their lytic activity. Data from 4 HDs are expressed as average±SD. *p-value=<0.05; **p-value=<0.001.

DETAILED DESCRIPTION OF THE PREFERRED EMBODIMENT

Example 1: Design and Study In Vitro and In Vivo of CAR-CD30 According to the Present Invention Material and Methods
Design of CAR-CD30 Plasmid (Constructs)

Figure 1:
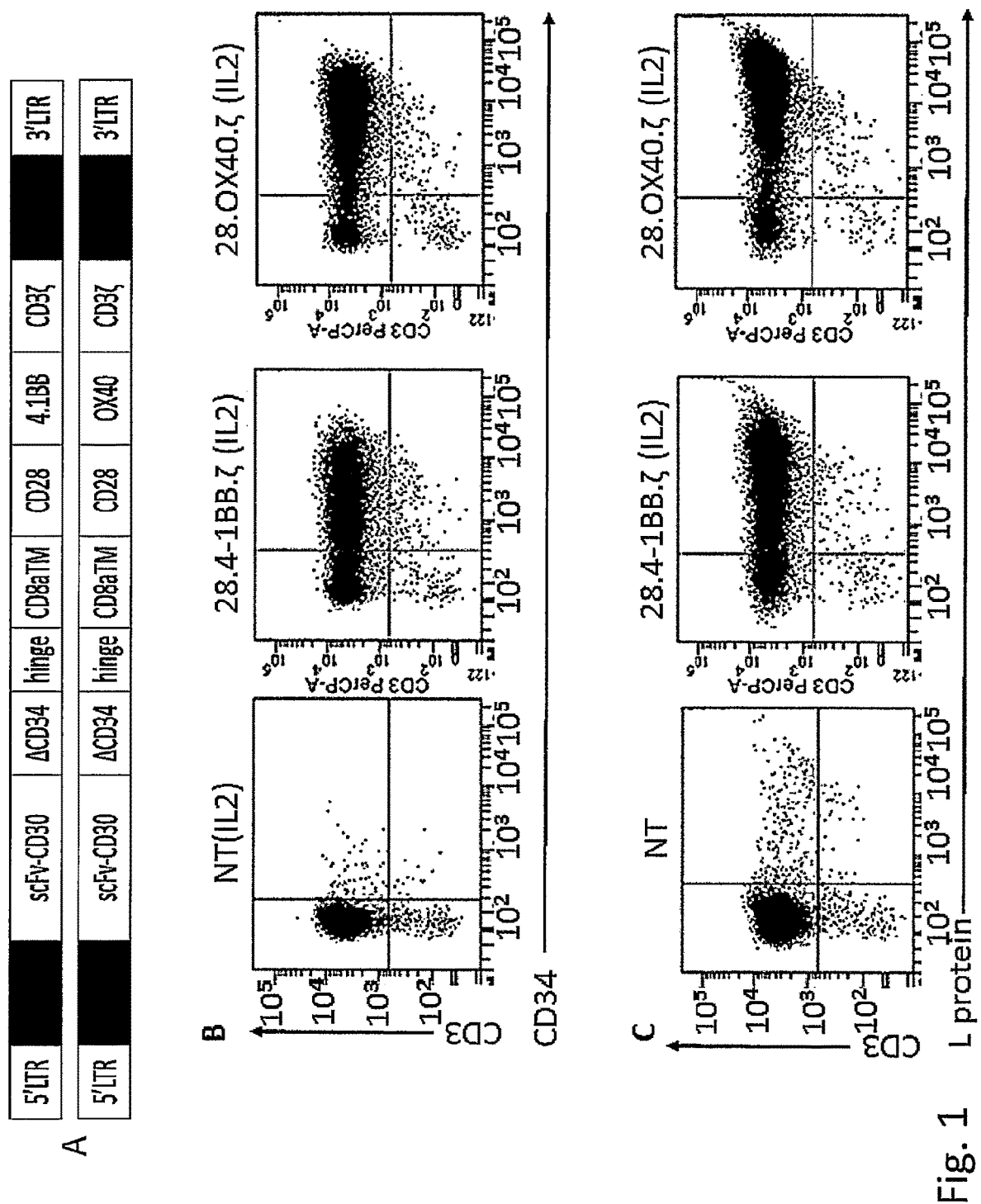
FIG. 1 CAR-CD30 T cells with CD28.OX40 or CD28.4-1BB costimulation exhibit similar transduction level, CD4+/CD8+ distribution, and in vitro proliferation upon initial antigen stimulation. (A) The expression cassette of two CAR-CD30 shown in cartoon. The scFv of CD30 was cloned in frame with CD8aTM, CD28 cytoplasmic moiety, and a second costimulatory domain represented by either 4-1BB (upper figure) or OX40 (lower figure), as well as the signaling domain CD3-zeta chain (ζ. As a trackable marker, ΔCD34 was added. (B) Flow-cytometry analyses shows the level of transduction of T cells by CD34 expression (upper panel) in an exemplificative donor, growth in IL2, of untransduced (NT) T cells, as negative control (left panels), or genetically modified T cells with CAR.CD30.ΔCD34.28.4.1BB.ζ (28.4.1BB.ζ) (middle panel) and genetically modified T cells with CAR.CD30.Δ.CD34.CD28.OX40.ζ (28.OX40.ζ) (right panel). (C) The level of transduction of T cells were confirmed also by Biotinylated Protein L; able to binds efficiently the scFv.(D-F) The 3 panels shows the average of the percentage of positive CAR+ T cells, profiled by FACS at three time of in vitro culture. First panel show CAR+CD3+ expression (D); the second panel (E) show the sub-population CAR+CD4+; and the last panel (F) the CAR+CD8+ T cells. For T cells growth in IL2 NT (white bar), 28.4.1BB.ζ (white bar with horizontal lines) and 28.OX40.ζ (black bar); or in IL7/IL15: NT (white bar with vertical lines), 28.4.1BB.ζ (grid bar) and 28.OX40.ζ (chessboard bar). Data are expressed as average±standard deviation (SD) from six healthy donors (HDs) at day 5, 15 and 30 of in vitro culture. (G-H) graph show the fold expansion in IL2, continuous lines (G) or IL7/IL15, dotted lines (H) of NT T cells and CAR-CD30 T cells, evaluated by trypan-blue count assay. Data represent results from 6 HDs. Effect of cytokine usage of in vitro long term fold expansion of NT T cells (I), 28.4.1BB.ζ T cells (L) and 28.OX40.ζ T cells (M). Significance were reported with an asterisk, while significance of variance of transduction level during the in vitro culture were reported with an asterisk encircled. *p-value=<0.05, **p-value=<0.01.
Figure 1:
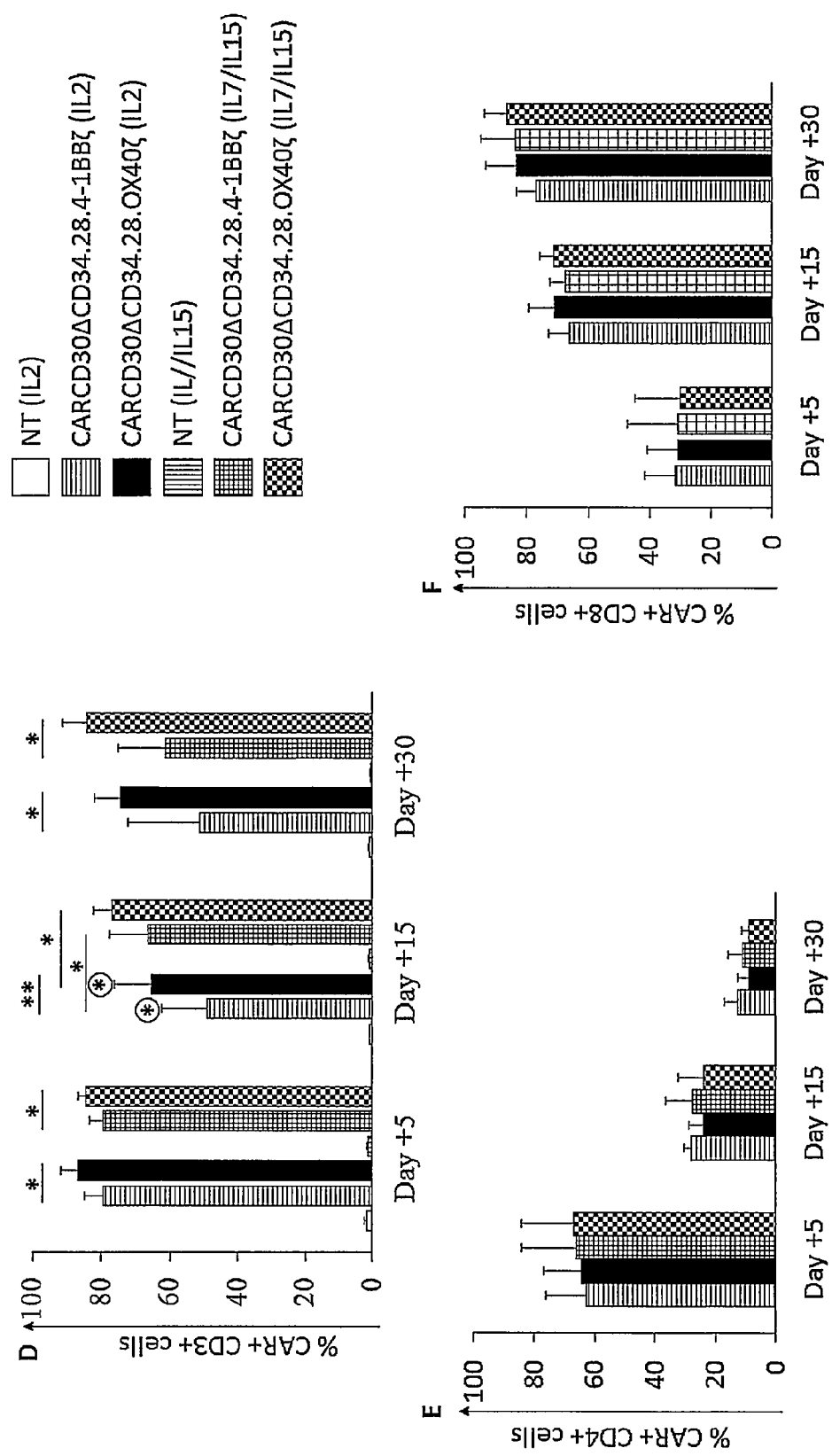
Figure 1:
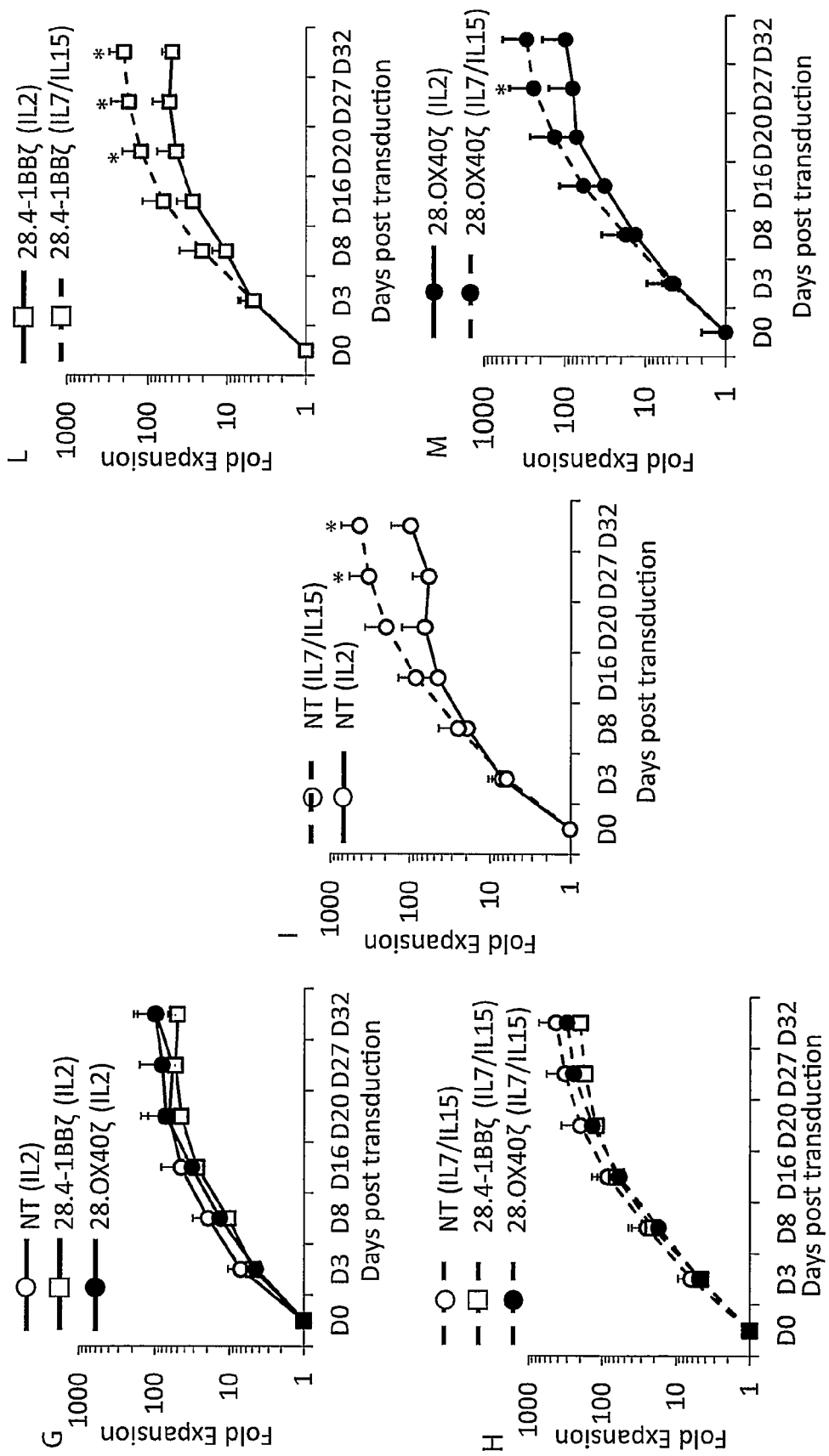

Two clinical grade "third" generation of retrovirus Vector SFG have been designed which carry the cassette anti-CD30 single-chain variable fragment (scFv), derived from a murine antibody of IgG (AC10) class, linked via a codon optimized human CD8 hinge-transmembrane domain, to the codon optimized signaling domains of the two costimulatory domains CD28, 4-1BB (CD137) or OX40 and CD3-ζ (FIG. 1A). The single chain variable fragment (scFv) specific for CD30 is a fusion protein of 111 amino acid (aa) of the variable regions of the light chains (VL) of immunoglobulins connected by flex (27)(a short linker peptide) of 8 amino acids to 117 aa of heavy chains (VH) of immunoglobulins. In particular the scFv AC10 is cloned in frame with codon optimized CD34 derived epitope of 16 aa (as trackable marker), linked by hinge of 40 aa (11 aa as spacer plus 29 aa of codon optimized CD8 extracellular domain) to bind the codon optimized human CD8-transmembrane domain (CD8aTM) of 30aa. The signal run from extracellular portion of CD30 scFv AC10 to intracellular portion of CD3-ζ chain (113aa) through two costimulatory molecules: CD28 endodomain (41aa) and 4-1BB endodomain (42aa) for the SFG.CAR.CD30(AC10)
ΔCD34.CD8aTM.CD28cyto.4.1BB.ζ retroviral vector (28.4-1BB.ζ).

The switch from the costimulatory molecules 4.1BB to OX40 (36aa) allow to obtain the SFG.CAR.CD30(AC10)
ΔCD34.CD8aTM.CD28cyto.OX40.ζ retroviral vector (28.OX40.ζ).

Generation of eGFP-Firefly-Luciferase Cell Lines.

The retroviral vector encoding eGFP-Firefly-Luciferase (eGFP-FFLuc) was used in selected experiments to label CD30+ tumor cells:
Non-Hodgkin's Lymphoma (NHL) Karpas 299,
Hodgkin's Lymphomas (HL) HDML-2 and L428;
Rhabdomyosarcoma RD,
Desmoplastic cerebellar medulloblastoma DAOY.
The retroviral vector encoding eGFP-Firefly-Luciferase (eGFP-FFLuc) was used in selected experiments to label CD30 negative control:
B cell precursor leukemia BV173,
Chronic Myelogenous Leukemia K562,
These cells lines were used for in vitro and in vivo study as previously described(9).
Cell Lines.
Non-Hodgkin's Lymphoma (NHL) Karpas 299 was obtained from Sigma-Aldrich. Hodgkin's Lymphomas (HL) HDML-2 and L428 and the B cell precursor leukemia Ph+BV173 were obtained from DSMZ. The rhabdomyosarcoma RD, the desmoplastic cerebellar medulloblastoma DAOY, the chronic myelogenous leukemia K562, the medulloblastoma D283 and the embryonic kidney 293T cell line were obtained from LGC Standards-ATCC.

The Karpas 299, HDML-2, L428, the BV173 and le K562 cell lines were maintained in culture with RPMI 1640 medium (Gibco; USA). The RD, the DAOY tumor cell lines and the 293T cells were maintained in culture with DMEM medium (Gibco, Invitrogen™, Carlsbad, Calif.) and the D283 was maintained in IMDM (Life Technologies Corporation, USA); Cell lines were supplemented with 10% fetal bovine serum (FBS, Hyclone, Thermo Scientific, Pittsburgh, Pa.) and 2 mM GlutaMax (Invitrogen, California, USA). Cells were maintained in a humidified atmosphere containing 5% $CO_2$ at 37° C. All cell lines were routinely tested for mycoplasma and for surface expression of target antigens. All cell lines have been authenticated by STR analysis in the certificated lab "BMR Genomics s.r.l."

Retroviral Supernatant

Transient retroviral supernatant was produced by cotransfection of 293T with the MoMLV gag/pol expression plasmid PeqPam3(-env), the RD114 env expression plasmid RDF, and SFG vectors at a ratio of 2:3:3, respectively, with a total of 10 μg DNA. The transfection was facilitated with GeneJuice reagent (Calbiochem). The supernatant was harvested 2 and 3 days after transfection, filtered (using a 0.45-mm filter), snap-frozen, and stored at −80° C. in 5-ml aliquots(28).

Isolation, Generation and Transduction of Effector Cells.

Peripheral blood mononuclear cells (PBMC) were isolated from peripheral blood (PB) or buffy coat obtained from healthy donors (OPBG Hospital, Rome, Italy) after that signed informed consent was obtained, in accordance with rules set by Institutional Review Board (IRB) of OPBG (Approval of Ethical Committee No 969/2015 prot. No 669LB), using Lymphocytes separation medium (Eurobio; France). T lymphocytes were activated with immobilized OKT3 (1 μg/ml, e-Bioscience Inc.; San Diego, Calif., USA) and anti-CD28 (1 μg/ml, BD Biosciences, Europe) antibodies in the presence of recombinant human interleukin-2 (IL-2, 100 U/ml; R&D; USA)(28), or with a combination of recombinant human interleukin-7 (IL7, 10 ng/ml; R&D; USA)(29) and recombinant human interleukin-15 (IL15, 5 ng/ml; R&D)(18, 30). Activated T cells were transduced on day 3 in 24-well plates pre-coated with recombinant human RetroNectin (Takara-Bio. Inc; Japan) using a specific retroviral supernatant and the specific above-described cytokines. At day 5 from transduction the T cells are expanded in "CTL complete medium" containing 45% RPMI1640 and 45% Click's medium (Sigma-Aldrich, Co.; Usa) supplemented with 10% FBS and 2 mM Glutamax, and fed twice a week with the specific above described cytokines.

Phenotypic analysis. Expression of cell surface molecules was determined by flow cytometry using standard methodology. The following monoclonal antibodies (mAbs) were used: CD3, CD4, CD8, CD25, CD27, CD28, CD45RA, CD45RO, CD56, CD57, CD62L, CD62E, CD62P, CD95, CD106, CD127, CD137, CD197, CD223 (Lag3), CD274 (PDL1), CD279 (PD1), and TIM3. The expression of CAR-CD30 on T cells was detected using a specific anti-CD34+ (QBENd10V Clone) or the Pierce Recombinant Biotinylated Protein L, able to binds efficiently the scFv. T-cell receptor (TCR)-Vβ repertoire on NT T cells and CAR-T cells, was evaluated at day +15 and day +30, using a panel of 24 different TCR Vβ-specific mAbs (IO TEST Beta Mark TCR-Vβ repertoire kit, BC) used in association with CD3 specific mAb (BD Biosciences) and isotype control mAb (BD Biosciences)(31). Samples were analyzed with a BD LSRFortessa X-20. Flow cytometry profiles were analyzed using the FACSDiva software (BD Biosciences). For each sample, a minimum of 20,000 events have been analyzed.

TCR V Beta (β) Repertoire

To evaluate the relative TCR Vβ repertoire distribution between NT and CAR modified T cells at day +15 the IOTest® Beta Mark Kit (Beckman Coulter) was used. This method use a multi-parametric analysis tool designed for quantitative determination of the TCR Vβ repertoire of human T lymphocytes by flow cytometry.

CFSE Dilution Method Assay

To evaluate whether the CAR-CD30 T cells proliferate only in the presence of specific antigen or cytokine usage, T cell was labeled with the fluorescent cell staining dye carboxyfluorescein succinimidyl ester (CFSE), using the CellTrace™ CFSE Cell Proliferation Kit, for flow cytometry (Invitrogen).

Chromium release assay. The cytotoxic activity of transduced effector cells was evaluated using a 6-hour chromium release assay as previously described(9). Target cells (Karpas 299, HDML-2, L428 and BV173) were labeled with radioactive chromium ($^{51}$Cr, PerkinElmer, cat no NEZ030S) and subsequently washed prior to co-culture with CAR T cells at different ratio for 4 hours. Co-culture supernatants were analyzed on the Microbeta$^2$ 2450 Microplate Counter (Pekin Elmer). The mean percentage of specific lysis of triplicate wells was calculated as follows: [(Experimental release-spontaneous release)/(maximal release-spontaneous release)]×100.

Co-culture assay. For co-culture experiments, control non transduced (NT) and CAR-CD30 T lymphocytes were plated at 1×10$^6$ cells/well in 24-well plates at the indicated Effector:Target (E:T) ratios. Following 7 days of incubation at 37° C., tumor cells and T cells were collected and residual tumor cells and T cells assessed by fluorescence-activated cell-sorting (FACS) analysis based on CD3 expression (Effector T cells) and GFP or CD30+ (tumor cell line).

Enzyme-Linked Immunosorbent Assay and Cytometric Bead Array

The production of the IFNgamma was quantified by specific ELISA using commercially available kits (R&D Systems, Pepro-Tech, Rocky Hill, N.J.). Supernatants tested with ELISA were collected from the co-cultures assay.

In Vivo Experiments

All the in vivo experiments were in compliance with the ethical international, EU and national requirement and were approved by the Italian Health Minster (No88/2016-PR).

In Vivo NHL Mouse Model (Karpas 299)

NSG (strain NOD.Cg-Prkdcscid Il2rgtm1WjI/SzJ; from Charles River) mice 6 weeks of age were engrafted with 0.2×10$^6$ CD30+Karpas299-F-Luc.GFP by intravenous (i.v.) injection. Three days later, when the light emission of the tumor was consistently measurable, the mice received at i.v. injection of 10×106 control (non-transduced, NT) lymphocytes or T cells genetically modified with either the CAR.CD30.ΔCD34.28.4.1BB.ζ (28.4.1BB.ζ) or CAR.CD30.ΔCD34.CD28.OX40.ζ (28.OX40.ζ) grown for 12-15 days in IL2 or in a cocktail of IL7/IL15. Tumor growth was evaluated using IVIS imaging system (Xenogen). The intensity of the signal of the tumor was measured as total photon/sec/cm2/sr (p/s/cm2/sr). The signal of bioluminescence below of 5×10$^5$ p/sec/cm2/sr (measured of mice without tumor) was considered negative. The in vivo experiments was followed for 140 days. The circulating T cells on mice peripheral blood were evaluated periodically.

Re-Challenging Model: The Establishment of Long-Term Immunological Memory in NHL Mice Model.

Mice engrafted with the NHL CD30+Karpas299-F-Luc.GFP tumor cell lines and treated with one single doses of CAR.CD30 T cells were monitored for 140 days and they were considered cured when a complete eradication of the tumor was observed (with a bioluminescence signal below to 5×10$^5$ p/sec/cm2/sr.) for an least seventy days. To evaluate the establishment of long-term immunological memory, cured mice were re-challenged at day +140 i.v. with 0.2×10$^6$ CD30+ Karpas299-F-Luc.GFP tumor cell line. The mice were followed for at least other 110 days. A new cohort of control mice (CTR mice) were added to the experiment as positive control of the engraftment of the tumor. The circulating T cells on mice peripheral blood were evaluated before and after re-challenged the CD30+ Tumor. The mice were euthanized on day 250.

In Vivo HL Mouse Model (L428)

NSG mice 6 weeks of age were engrafted with $2 \times 10^6$ CD30+L428-FF-Luc.GFP by intravenous (i.v.) injection. Six days later, when the light emission of the tumour was consistently measurable, the mice received intravenous (iv) injection of $10 \times 10^6$ control (non-transduced, NT) lymphocytes or T cells genetically modified with either the CAR.CD30.ΔCD34.28.4.1BB.ζ (28.4.1BB.ζ) or CAR.CD30.ΔCD34.CD28.OX40.ζ (28.OX40.ζ) grown for 12-15 days in IL2 or in a cocktail of IL7/IL15. Tumor growth was evaluated using IVIS imaging system (Xenogen).

Statistical Analysis

Statistical Evaluation were performed using GraphPad Prism (GraphPad Software), Differences between groups generating P-values<0.05 were considered significantly.

When multiple comparison analyses were required, statistical significance was evaluated by a repeated measures ANOVA followed by a Log-rank (Mantel-Cox) test for multiple comparisons. The mouse survival data were analyzed using the Kaplan-Meier survival curve and Fisher's exact test was used to measure statistically significant differences. No valuable samples were excluded from the analyses. Animals were excluded only in the event of their death after tumor implant but before T-cell infusion. Neither randomization nor blinding was done during the in vivo study. However, mice were matched based on the tumor signal for control and treatment groups before infusion of control or gene modified T cells. To compare the growth of tumors over time, bioluminescence signal intensity was collected in a blind fashion. Bioluminescence signal intensity was log transformed and then compared using a two-sample t-test. The analysis of the pathologist, aimed at quantifying tumor volume, was performed in a blind fashion.

Results

Generation, Characterization of CAR-CD30 T Cells

Two potent third generation of CAR-CD30 (CAR-CD30) T cells have been generated, containing the single chain variable fragment (scFv) derived from a murine antibody of IgG (AC10), in frame with CD28, and a second costimulatory domain represented by either 4-1BB or OX40, as well as the signaling domain CD3-zeta chain (ζ). As a selectable marker a small molecule derived from the phosphoglycoprotein CD34 (ΔCD34), FIG. 1A has been added. Activated T-cells (ATCs), growth in CTL complete medium with IL2 or a cocktail of IL7/IL15, were established from six healthy donors and transduced with retroviral supernatant encoding the CAR.CD30.ΔCD34.28.4.1BBζ(28.4.1BB.ζ) or CAR.CD30.ΔCD34.CD28.OX40.ζ (28.OX40.ζ) SFG vectors respectively. As a negative control, non-transduced (NT) ATCs were cultured in parallel. Transduced T cells were detected by flow cytometry using efficiently or CD34 antibody (clone QBEnd10), as shown in representative FIG. 1B, or in alternative the protein L reagent(32), FIG. 1C. As shown in FIG. 1D, T-cells transduced with either 28.OX40.ζ or the 28.4.1BB.ζ construct expressed high levels of CAR-CD30. However at day +5 the level of transduction was significant higher in T cells transduced in IL2 with the vector encoding 28.OX40.ζ (IL2) respect to 28.4.1BB.ζ (IL2)

(87.3%±5.1% vs. 76.1%±9.8%, respectively, p<0.05; (average±standard deviation (SD) is reported here and throughout the manuscript unless otherwise specified). Similar results were obtained also for T cells transduced in IL7/IL15. At day +5 the level of transduction was similarly higher in 28.OX40.ζ (IL7/IL15) T cells (84.1%±2.2%) than in 28.4.1BB.ζ(IL7/IL15) T cells (78.6%±3.9%), p<0.05. Notable in both CD3+ CAR.CD30 T cells growth in IL2, the level of transduction significantly decreased at day +15 (65.1%±10.9% for 28.OX40.ζ(IL2) and 49.2%±13.3%, for 28.4.1BB.ζ(IL2) respectively, p<0.05; asterisk), remaining for the next two weeks more stable at least until day +30 (73.0%±6.4% vs. 55.9%±18.1%, 28.OX40.ζ(IL2) and 28.4.1BB.ζ(IL2) respectively). The switching in IL7/IL15, independently of constructs used, significantly improve the stability and the level of transduction in CD4+ and/or CD8+ T cells.

In CAR T cells the CD4+/CD8+ ratio decrease weekly, FIG. 1E (CAR+CD4+), coming out in favors of CAR+ CD8+, FIG. 1F. A day +15 a predominance of CD8+ in both CAR.CD30 T cells were obtained. The same trend for NT T cells was observed. The expansion rate of modified T cells did not change significantly from NT T cell when cultured in IL2 (FIG. 1G) or in IL7/IL15 (FIG. 1H). However, the cocktail IL7/IL15, in long-term in vitro culture, improve significantly the fold expansion of NT (FIG. 1I) and transduced T cells (FIGS. 1L and 1M).

Memory and Exhaustion Profiles of Gene Modified CAR-CD30 T Cells

To evaluate the influence of specific costimulatory domains and cytokines on CAR.CD30 T-cell compartment, CD3+ CAR-T cells were characterized for the expression of memory markers. At day +15 of culture, the majority of expanded T cells generated after CD3/CD28 stimulation and culture with IL2 had an Effector Memory (EfM) phenotype with no substantial difference between NT and the two kinds of CAR.CD30 T cells. However, the switching in IL7/IL15 reduced significantly the Central Memory (CM) compartment a favor of EfM and Effector Terminal (EfT) in CAR.CD30 T cells. After 30 days of in vitro culture, only a significative (only for T cells cultured in IL2) reduction of Naïve CAR.CD30 T cells was noticed.

Figure 2:
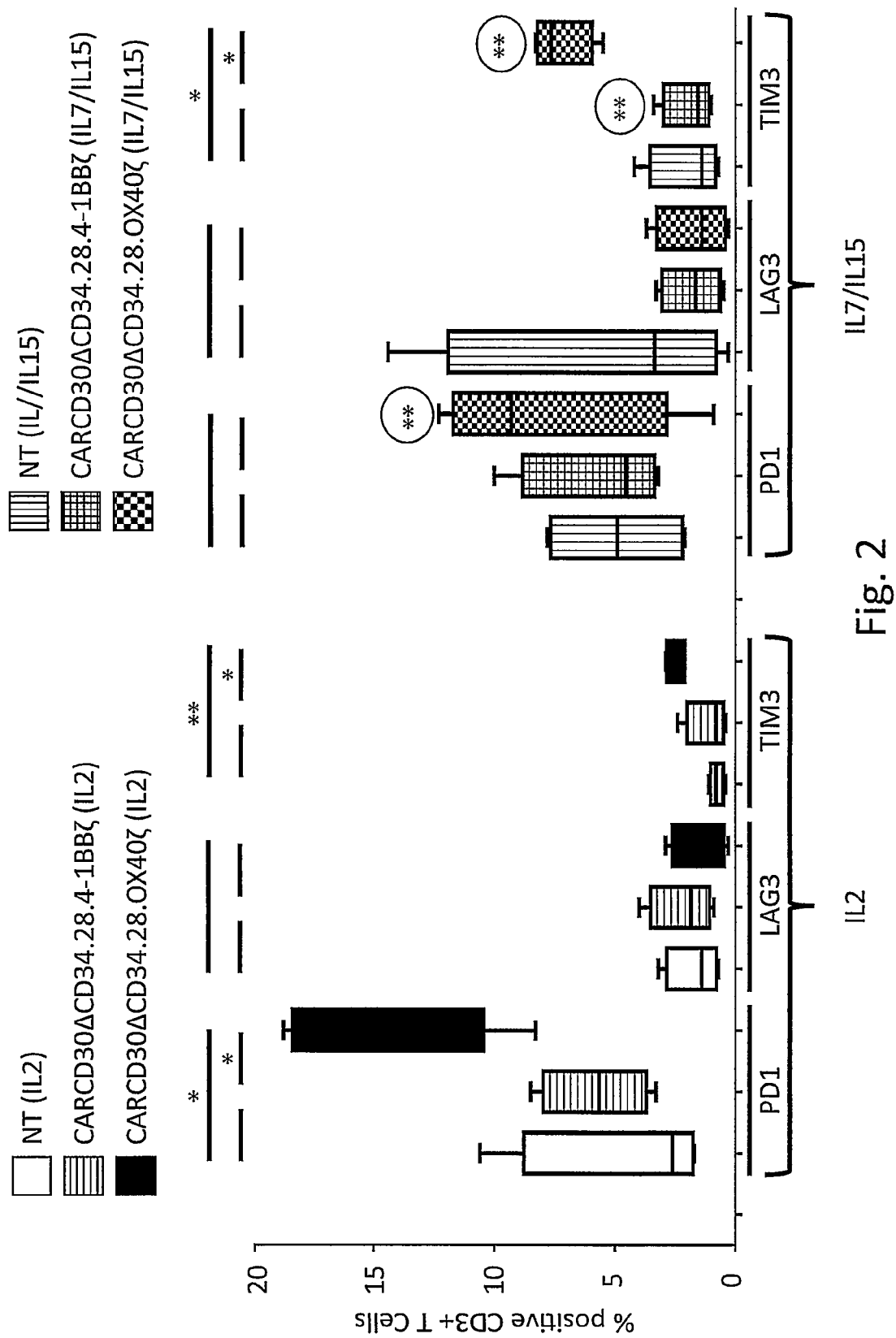
FIG. 2. Exhaustion profiles of gene modified CAR-CD30 T Cells.

The pattern of inhibitory-receptors (PD-1, LAG3 and TIM3) simultaneously expressed by CAR+ T cells was also evaluated in order to define their exhaustion status (FIG. 2). It was observed that, when T cells were transduced with (28.OX40.ζ), in IL2, at day +15 of in vitro culture, a significative upregulation of PD1 and TIM3 has been observed respect to NT or CARCD30.28.4-1BB.ζ T cells (FIG. 2). Notable the switching from IL2 to IL7/IL15 reduced significantly the PD1 expression in CARCD30.28.OX40.ζ T cells (15.33%±4.75% in IL2 and 7.95%±4.93% in IL7/IL15, respectively, p=0.006), but upregulate TIM3 expression (2.45%±0.41% in IL2 and 7.28%±1.26% in IL7/IL15, respectively, p=0.009). A day +30 of in vitro culture the exhaustion profile of NT and CARCD30 modified T cells were typically determined by PD1 and TIM3 expression.

Safety Profile of CAR-CD30 T Cells

To evaluate the influence of retroviral modification or culture condition on safety profile of modified T cells, for NT or CAR-CD30 T cells the basal proliferation or cytokine or/and antigen specific proliferation were evaluated. T cells were labeled at day zero with the fluorescent cell staining CFSE and plated for five days with/out cytokines, or co-cultured in the presence of tumor cell line CD30 positive (Karpas299) or tumor cell line CD30 negative (BV173). The basal proliferation of CD3+ cells has been evaluated, but also of CD8+ cells and CD4+ cells. NT T cells proliferate only when cultured with IL2 (50 U/ml) (FIG. 3A-II) or combination of IL7 (10 ng/ml)/IL15 (5 ng/ml)(FIG. 3A-III), as shown by CFSE dye dilution. The proliferation was preferentially due to CD8+ cells (A middle panel). In contrast for CAR-CD30 T cells a specific CFSE dye dilution was observed also when they were co-cultured in presence of Karpas299 cell lines (FIG. 3B-IV and FIG. 3C-IV) but not in presence of BV173 tumor cell line (FIG. 3B-V and FIG. 3C-V) or when plated without cytokines (B-I and C-I). Moreover, to evaluate the polyclonal expansion of cultured T cells, at day +15 and day +30 of in vitro culture, whether there was the concordance of TCR Vβ repertoire distribution between NT and both CAR-CD30 T cells growth in IL2 or IL7/IL15 was determined. No significant preferential expansion of specific clone's cytokine or CAR dependent was observed, even when the cells were cultured up to 30 days (data not shown).

CAR-CD30 T Cells Efficiently Lyse In Vitro CD30+ Lymphoma, but Also Solid Tumor as Medulloblastoma and Sarcoma Cell Lines The capacity of CAR-CD30 T cells to kill CD30+ human tumor cell lines was then evaluated.

As well known, the cell membrane protein CD30 was expressed on 2 out of 2 Hodgkin's lymphoma cell lines, FIG. 4A (HDML-2, L428) and 1 out of 1 NHL cell line (Karpas 299). Interesting CD30+ was also 1 out of 5 sarcoma cell lines (CD30 positive: RD and CD30 negative: SK-ES-1, A673, CW9019 and CT-10) FIG. 4B; 1 out of 2 medulloblastoma cell lines tested (CD30 positive: DAOY and CD30 negative: D283) FIG. 4C; and one T lymphoblastic cell line T2 (CEM.T2, but not in one B cell leukemia cell line BV173 (FIG. 4D).

Moreover, the follow CD30+ tumor cell lines expressed also high level of PDL1 (KARPAS 299 and HDML-2). To evaluate the relative influence of PDL1 on intrinsic resistance of CD30+ tumor cell line to be killed by CARCD30 T cells, the HL L428 (PDL1 negative) was transduced to stably express PDL1, FIG. 4E.

In $^{51}$Cr release assays both CARCD30 T cells were able to lyse, specifically and with high efficiency, the CD30+ lymphomas, as Karpas 299 (FIG. 5A), the HDML-2 (FIG. 5B), L428 (FIG. 5C), but not CD30-leukemia cell line BV173 (FIG. 5F). Notable both CAR-CD30 T cells showed to kill also the desmoplastic cerebellar medulloblastoma DAOY (FIG. 5D). As CD30 negative control for solid tumor, the medulloblastoma D283 (FIG. 5E) and the leukemia cell line BV173 (FIG. 5F) were tested. The switching from IL2 to the cocktail IL7/IL15 did not improve the potency of CAR-CD30 T cells (FIG. 6A-F).

As shows by representative donor, in 7 days long-term co-culture, using the ratio effector target one to one (R1:1), a specific and comparable potency of both CAR-CD30 T cells on GFP+ lymphoma cell lines (FIG. 7A-D) was observed. Notable the expression of PDL1 on L428 tumor cell line (FIG. 7D) did not influence apparently the sensitivity of L428 tumor cell line to both CAR-CD30 T cells, respect to L428 wild type (FIG. 7C). Moreover a significative tumor control was observed also in other CD30+ tumor cell lines, as CD30+GFP+ leukemia cell lines (FIG. 7E) but not in CD30 negative BV173 (FIG. 7F); in CD30+GFP tumor DAOY medulloblastoma cell line (FIG. 7G) and in CD30+RD sarcoma cell lines (FIG. 7I) but not in CD30 negative CD45 negative D283 medulloblastoma cell line (FIG. 7H). Notable for solid tumors the 28.OX40.ζ kills significantly better than 28.4.1BB.ζ (FIGS. 7G and 7I), but not in CD30 negative SK-ES-1(FIG. 7J). These results were confirmed for six different donors, expanded in IL2 (FIG. 7K) or in IL7/IL15 (FIG. 7L).

In the present study, the cytokine culture conditions did not influence the in vitro specific cytolytic activity of CAR-CD30 T cells against CD30+cells, when tested in a standard Chromium cytotoxic assay (FIG. 5-6), or in a long-term co-culture (FIG. 7). To evaluate the real power of the lytic potency between two CAR-CD30 T cells, the in vitro long-term co-culture potency assay was stressed increasing the target tumor cells from R 1:1 to R 1:32. Noteworthy, the activity of CAR.CD30 T cells at low effector/target ratios showed a significant improvement of the in vitro tumor control of 28.OX40.ζ(IL2) T cells for the Karpas 299 (in R1:8 and R1:16) and HDML-2 cell lines (in R 1:8, R1:16 and R1:32) (FIG. 8A-B, respectively), however for L428 no significative difference of cytolytic activity between 28.OX40.ζ(IL2) and 28.4.1BB.ζ (IL2) was observed.

For CAR-CD30 T cells (IL7/IL15) superior lytic activity of 28.OX40.ζ was confirmed, in particular at lower effector/target ratios for Karpas 299 and HDML-2 cell lines, although it cannot reach the significance respect to 28.4-1BB.ζ (FIGS. 8D and 8F, respectively). Overall these data confirmed of superior CD30+ specific activation of 28.OX40.ζ (IL7/IL15), when co-cultured with Karpas 299 and HDML-2, in term of specific IFN-gamma production, evaluated on supernatant collected 24 hours from co-culture potency assay (FIGS. 9A-B and 9D-E). Both CAR-CD30 T cells produce specific and equal level of IFN-gamma when co-cultured with the CD30+Tumor cell line L428 (FIGS. 9C and 9F).

The Establishment of Long-Term Immunological Memory in NHL Mice Model.

The in vivo efficacy and persistence of CAR-CD30 T cells were compared against the NHL Karpas299-FF-Luc.GFP tumor cell line (FIG. 10A) in a xenograft model, using immunodeficient NSG mice.

While in the group treated with NT (IL2) T cells, the bioluminescence of the tumor progressively increased (FIG. 10B-C), in mice treated with 10×10$^6$ CAR-CD30 T cells (IL2) a significative tumor control was observed, as measured by reduction or control of bioluminescence signal. The median survival of the mice treated with NT cells (IL2) reach only 45.5 days, 30% of mice treated with 28.4.1BB.ζ (IL2) and 60% of mice treated with 28.OX40.ζ(IL2) respectively experienced long-term tumor control (FIG. 10D). Specifically the median survival of mice treated with 28.4.1BB.ζ (IL2) was 58 days (p=0.05), and undefined for mice treated with 28.OX40.ζ (IL2) (p=0.0002) (FIG. 10D).

After 140 days of treatments, cured mice (3 mice treated at day 0 with 28.4.1BB.ζ (IL2) and 6 mice with 28.OX40.ζ (IL2) were re-challenged i.v. with the same tumor (0.2×10$^6$), and the mice were followed for other 100 days. In this setting of experiments, 6 new mice were added as positive control mice (CTR mice), that received CD30+Karpas299-F-Luc.GFP by intravenous injection (i.v.) (FIG. 11A). By evaluation of bioluminescence of the Karpas299-F-Luc.GFP reinfused at day +140, it was taken note of rapid progression of the tumour in CTR mice (lines with white circle) and 28.4-1BB.ζ (IL2) treated mice (lines with white square) (FIG. 11B-C). In contrast in 28.OX40.ζ (IL2) treated mice (lines with black square), after an initial expansion of the tumor for the first 40 days, the 66.67% (4 out 6) of the mice eradicate for the second time the re-challenged tumor, with a significative survival benefit (FIG. 10D). To confirm the establishment a long-term immunological memory, the blood was sampled and analysed in treated mice, after the first tumour infusion (day +6, +56, +103 and +132) and the second tumour infusion (day +180, +221 and +254). In particular, for mice treated with 28.OX40.ζ (IL2) a significative expansion of circulating T cells (FIG. 11E) was observed in conjunction with the infusion of the Lymphoma (2.49%±1.03%, p<0.005) respect of mice treated with 28.4-1BB.ζ (IL2) (0.275%±0.109%) or NT (IL2) (0.347%±0.071%). Interesting after the eradication of the first tumor, when at day +132, the circulating T cells in cohort of mice treated with CAR-CD30 T cells was evaluated, only 0.022%±0.027% and 0.090%±0.1355% of T cells were quantified, for 28.OX40.ζ (IL2) and 28.4.1BB.ζ (IL2) respectively. Forty days after the tumor re-challenging (day +180) a slow, but impressive expansion of circulating 28.OX40.ζ (IL2) T cells (7.216%±11.259%), respect to 28.4.1BB.ζ (IL2) (0.093%±0.129%) was appreciated. The complete eradication of the second tumour followed the simultaneous reduction of circulating 28.OX40.ζ (IL2) T cells to undetectable percentage, as measured at day +254 (0.001%±0.0018%).

Evaluation of Efficacy and Persistence of CAR-CD30 T Cells in NHL Mice Model.

Successively the influence of cytokine usage of in vivo efficacy of CAR-CD30 T cells grow for 15 days in IL2 or IL7/IL15, against the more aggressive HL L428 was evaluated. Mice received at day-6 i.v. 2×10$^6$ L428-FF-Luc.GFP cell line and, when the light emission of the tumor was consistently measurable, the mice were treated i.v. with NT or genetically modified T cells. To evaluate the persistence of human circulating T cells, the treated mice were blood sampled at day +15, +30, +56, +80, +100, +130, +160 (FIG. 12A). The bioluminescence of the L428 cell line in HL-tumor-bearing mice, treated with NT T cells, rapidly increase up to five log in less of 50 days (FIG. 12B and FIG. 12C), and the mice died or were sacrificed for morbidity. The macroscopic analysis of organs in sacrificed mice shown a large tumor mass preferentially present on the liver. HL-tumor-bearing mice treated with 28.4-1BB.ζ (IL2) survived on median slightly significantly longer (79±10 days) respect HL-tumor-bearing mice treated with NT (IL2), NT(IL7/IL15) (52±9 and 58±1 days respectively) (FIG. 12B-E). The switching in IL7/IL15 did not improve the cytotoxic in activity of 28.4-1BB.ζ (IL7/IL15) (FIG. 12B-D). The median of survival of HL-tumor-bearing mice treated with 28.OX40.ζ (IL2) improve significantly up to 133±4 days respect to mice treated with NT(IL2) or 28.4-1BB.ζ (IL2). When the HL-tumor-bearing mice were treated with 28.OX40.ζ (IL7/IL15) the median of survival became undefined, without however any significant difference of overall survival between mice treated with two 28.OX40.ζ CAR T cells (p=0.0876 and FIG. 12E). To evaluate the persistence of infused T cell, the blood circulating T cells in NSG mice bearing L428 tumors were monitored periodically and treated with NT or genetically modified T cells for all the period of the experiment (FIG. 12F). Although, also mice treated with NT T Cells, showed a significative increase of human circulating CD45+CD3+ cells with a peak evaluated at day +56 (26.69%±7.02% and 5.97%±9.63%, for NT (IL2) and NT(IL7/IL15) respectively, no tumor control was observed.

At day 80 in only one survived mouse treated with 28.4-1BB.ζ (IL2), a very high number of circulating human T cells (CD45$^+$CD3$^+$=20.56%) was measured, but with low level of transduction (CD3$^+$CD34$^+$=4.57%). In contrast in all four mice treated with 28.OX40.ζ (IL2) the circulating T cells (CD45$^+$CD3$^+$) at day +80 was in average 9.79%±5.24% (range 3.08%-15.37%), with a stable level of transduction equal to 34.23%±5.87%. Interesting in mice treated with 28.OX40.ζ (IL7/IL15) a significative reduced level of circulating T cells (0.92%±0.56%, p=0.0065) with higher percentage of transduced T cells (41.89%±2.25%, p=0.0300) was measured. The complete eradication of the tumor infused in the mice treated with 28.OX40.ζ CAR T cells was followed by the reduction of circulating T cells. The percentage of circulating CAR-CD30 T cells remain stable during the first 100 days. A day +165 residual circulating T cells were found in only in two mouse treated on four (0.06%±0.02%). All four mice resulted cured at this time. In this two mice the CAR-CD30 T cells show to be equally distribute between CD4+ and CD8+, as central memory (CM), defined as CD45RA-CD62L+ and Effector memory (EM), defined as CD45RA-CD62L−; FIG. 12G.

Example 2: Tumor Modulation of Memory and Exhaustion Profiles in CAR.CD30 T Cells According to the Present Invention (28.OX40.ζ T Cells and 28.4-1BB.ζ T Cells)

Materials and Methods

Stressed Co-Culture Assay

For stressed co-culture experiments, non-transduced (NT) control and CAR.CD30 T lymphocytes (28.OX40.ζ T cells and 28.4-1BB.ζ T cells) were plated at 1×10$^6$ cells/well in 24-well plates at the indicated Effector: Target (E:T) ratios 1:1. To evaluate how long CAR.T cells were able to eliminate the tumor when added more than one time, tumor cells were added to the well at day zero, 5, 10 and 15. The residual tumor cells and persistence of T cells by FACS analysis based on CD3 expression (Effector T cells) and GFP or CD30+ (tumor cell line) up to 20 days of co-culture were then evaluated.

Enzyme-Linked Lectin Assay

Supernatant from E:T co-culture was collected at 24 hours to evaluate the level of Interferon-γ (IFNγ), Interleukin-2 (IL-2), Interleukin-10 (IL-10) and Tumor Necrosis Factor-α (TNF-α) using ELLA protocol (R and D System).

Results

In order to evaluate the lytic effectiveness of CAR.CD30 T cells in a more complex contest, the co-culture conditions were "stressed" by re-challenging the tumor (Karpas 299) every five days (at day 0, +5, +10 and +15 of co-culture) (FIG. 13A). At each time point, the percentage of residual tumor and the behavior of CAR.CD30 T cells were evaluated, by evaluating the single chain expression and the relative mean fluorescence intensity (MFI), the memory and exhaustion profile and the relative specific cytokines production as IFNγ, TNFα, IL-2 and IL-10 (at day 1, +6, +11 and +16 of co-culture). Both CAR.CD30 T cells exhibited high tumor control even after multiple exposures to Karpas 299. Although significant differences in lytic activity at day +5 and day +10 between them were not observed, 28.OX40.ζ T cells shown a major tumor control at day +20 (8.6%±5.3% for 28.OX40.ζ and 27.9%±29.5% for 28.4-1BB T cells) (FIG. 13B). Interesting the percentage in both CAR.CD30 molecules significantly increased after the first co-culture, from 66.9%±15.23% (day +5) to 93.8%±11.3% (day 10) for 28.4-1BB.ζ T cells, p=0.022 and from 74.9%±11.3% (day +5) to 93.2%±11.3% (day +10) for 28.OX40.ζ T cells, p=0.007). Indeed, the next tumor re-challenging negatively influenced the level of transduction only for 28.4-1BB.ζ T cells from 93.8%±3.06% (day +10) to 67.9%±32.33% (day +20) while in 28.OX40.ζ T cells the percentage remained stable from 93.22%±2.75% (day +10), to 92.53%±3.45% (day +20) (FIG. 13C).

Moreover, the MFI of 28.OX40.ζ T cells was significantly higher than 28.4-1BB.ζ T cells at each time point (11294.83±580453 vs 24004±11365.6 at day 0, p=0.006; 16883±6703.47 vs 40671.2±12162.2 at day 5, p=0.004; 7382.75±4042.01 vs 25329.75±14746.76 at day 10, p=0.037; 11729.83±11158.66 vs 29552.83±234643.32 at day 15, p=0.035; 8344.5 vs 23834.83±11272.55 at +20, p=0.001) (FIG. 13D).

Furthermore, the cytokine profile confirmed a prompter activation of 28.OX40.ζ T cells, resulting in a significant IFNγ production, also at day +20 of stressed co-culture (4768.86 pg/ml±3708.34 pg/ml) compared to 28.4-1BB.ζ T cells (2699.54 pg/ml±2517.10 pg/ml, p=0.012) (FIG. 13E) and TNFα production (8439.32 pg/ml±6187.27 pg/ml) compared to 28.4-1BB.ζ T cells (2983.40 pg/ml±2497.48 ng/ml, p=0.013) (FIG. 13F). Furthermore, the difference between CAR.CD30 T cells, in the production of IL-2, was significantly different until day +10, that correspond to tumor challenging number II) (8480.82 Pg/ml±5065.76 Pg/ml for 28.OX40.ζ T cells) compared to 28.4-1BB.ζ T cells (2778.64 pg/ml±3852.82 pg/ml, p=0.006) (FIG. 13G). The alternative manner to evaluate the tumor control is the detection of the cytokine IL-10 (produced by Karpas299 cell line). As shown in FIG. 13H, from day +10 the level of IL-10 detected in NT T cells culture media (white bars) was similar to the quantity detected plating tumor alone (horizontal lines bar) while high level of IL-10 was detected only after 24 hour of the first co-culture (challenging number I) with CAR.CD30 T cells (FIG. 13H).

The results show that CAR.CD30 T cells with CD28.OX40 costimulatory domain were able to control the tumor more efficiently with respect to 4.1BB costimulatory domain during the sequential additions of CD30+ lymphoma up to 4 time ("stressed" co-culture), producing significantly higher amount of IFN-gamma, TNF-alpha and IL-2 when co-cultured with Karpa299 tumor cell line.

BIBLIOGRAPHY

1. Brudno J N, and Kochenderfer J N. Chimeric antigen receptor T-cell therapies for lymphoma. *Nature reviews Clinical oncology.* 2017.
2. Rezvani A R, Storer B, Maris M, Sorror M L, Agura E, Maziarz R T, Wade J C, Chauncey T, Forman S J, Lange T, et al. Nonmyeloablative allogeneic hematopoietic cell transplantation in relapsed, refractory, and transformed indolent non-Hodgkin's lymphoma. *Journal of clinical oncology: official journal of the American Society of Clinical Oncology.* 2008; 26(2):211-7.
3. Haverkos B M, Abbott D, Hamadani M, Armand P, Flowers M E, Merryman R, Kamdar M, Kanate A S, Saad A, Mehta A, et al. PD-1 blockade for relapsed lymphoma post-allogeneic hematopoietic cell transplant: high response rate but frequent GVHD. *Blood.* 2017; 130(2): 221-8.
4. Wong R W J, Ngoc PCT, Leong W Z, Yam A W Y, Zhang T, Asamitsu K, Iida S, Okamoto T, Ueda R, Gray N S, et al. Enhancer profiling identifies critical cancer genes and characterizes cell identity in adult T-cell leukemia. *Blood.* 2017; 130(21):2326-38.
5. Zheng W, Medeiros L J, Young K H, Goswami M, Powers L, Kantarjian H H, Thomas D A, Cortes J E, and Wang S A. CD30 expression in acute lymphoblastic leukemia as assessed by flow cytometry analysis. *Leukemia & lymphoma.* 2014; 55(3):624-7.
6. Berger G K, Gee K, Votruba C, McBride A, and Anwer F. Potential application and prevalence of the CD30 (Ki-1) antigen among solid tumors: A focus review of the literature. *Critical reviews in oncology/hematology.* 2017; 113(8-17.
7. Evens A M, Hutchings M, and Diehl V. Treatment of Hodgkin lymphoma: the past, present, and future. *Nature clinical practice Oncology.* 2008; 5(9):543-56.
8. Savoldo B, Rooney C M, Di Stasi A, Abken H, Hombach A, Foster A E, Zhang L, Heslop H E, Brenner M K, and Dotti G. Epstein Barr virus specific cytotoxic T lymphocytes expressing the anti-CD30zeta artificial chimeric T-cell receptor for immunotherapy of Hodgkin disease. *Blood.* 2007; 110(7):2620-30.
9. Di Stasi A, De Angelis B, Rooney C M, Zhang L, Mahendravada A, Foster A E, Heslop H E, Brenner M K, Dotti G, and Savoldo B. T lymphocytes coexpressing CCR4 and a chimeric antigen receptor targeting CD30 have improved homing and antitumor activity in a Hodgkin tumor model. *Blood.* 2009; 113(25):6392-402.
10. Wang C M, Wu Z Q, Wang Y, Guo Y L, Dai H R, Wang X H, Li X, Zhang Y J, Zhang W Y, Chen M X, et al. Autologous T Cells Expressing CD30 Chimeric Antigen Receptors for Relapsed or Refractory Hodgkin Lymphoma: An Open-Label Phase I Trial. *Clinical cancer research: an official journal of the American Association for Cancer Research.* 2017; 23(5):1156-66.
11. Ramos C A, Ballard B, Zhang H, Dakhova O, Gee A P, Mei Z, Bilgi M, Wu M F, Liu H, Grilley B, et al. Clinical and immunological responses after CD30-specific chimeric antigen receptor-redirected lymphocytes. *The Journal of clinical investigation.* 2017; 127(9):3462-71.
12. Hombach A, Heuser C, Sircar R, Tillmann T, Diehl V, Pohl C, and Abken H. An anti-CD30 chimeric receptor that mediates CD3-zeta-independent T-cell activation against Hodgkin's lymphoma cells in the presence of soluble CD30. *Cancer research.* 1998; 58(6):1116-9.
13. Hombach A, Heuser C, Sircar R, Tillmann T, Diehl V, Pohl C, and Abken H. Characterization of a chimeric T-cell receptor with specificity for the Hodgkin's lymphoma-associated CD30 antigen. *Journal of immunotherapy.* 1999; 22(6):473-80.
14. Hombach A A, Gorgens A, Chmielewski M, Murke F, Kimpel J, Giebel B, and Abken H. Superior Therapeutic Index in Lymphoma Therapy: CD30(+) CD34(+) Hematopoietic Stem Cells Resist a Chimeric Antigen Receptor T-cell Attack. *Molecular therapy: the journal of the American Society of Gene Therapy.* 2016; 24(8):1423-34.
15. Louis C U, Savoldo B, Dotti G, Pule M, Yvon E, Myers G D, Rossig C, Russell H V, Diouf O, Liu E, et al. Antitumor activity and long-term fate of chimeric antigen receptor-positive T cells in patients with neuroblastoma. *Blood.* 2011; 118(23):6050-6.
16. Heczey A, Louis C U, Savoldo B, Dakhova O, Durett A, Grilley B, Liu H, Wu M F, Mei Z, Gee A, et al. CAR T Cells Administered in Combination with Lymphodepletion and PD-1 Inhibition to Patients with Neuroblastoma. *Molecular therapy: the journal of the American Society of Gene Therapy.* 2017; 25(9):2214-24.
17. Wein F, and Kuppers R. The role of T cells in the microenvironment of Hodgkin lymphoma. *Journal of leukocyte biology.* 2016; 99(1):45-50.
18. Perna S K, De Angelis B, Pagliara D, Hasan S T, Zhang L, Mahendravada A, Heslop H E, Brenner M K, Rooney C M, Dotti G, et al. Interleukin 15 provides relief to CTLs from regulatory T cell-mediated inhibition: implications for adoptive T cell-based therapies for lymphoma. *Clini-*

19. Karlsson H, Svensson E, Gigg C, Jarvius M, Olsson-Stromberg U, Savoldo B, Dotti G, and Loskog A. Evaluation of Intracellular Signaling Downstream Chimeric Antigen Receptors. *PloS one*. 2015; 10(12):e0144787.
20. Hudecek M, Sommermeyer D, Kosasih P L, Silva-Benedict A, Liu L, Rader C, Jensen M C, and Riddell S R. The nonsignaling extracellular spacer domain of chimeric antigen receptors is decisive for in vivo antitumor activity. *Cancer immunology research*. 2015; 3(2):125-35.
21. Maher J, Brentjens R J, Gunset G, Riviere I, and Sadelain M. Human T-lymphocyte cytotoxicity and proliferation directed by a single chimeric TCRzeta/CD28 receptor. *Nature biotechnology*. 2002; 20(1):70-5.
22. Condomines M, Arnason J, Benjamin R, Gunset G, Plotkin J, and Sadelain M. Tumor-Targeted Human T Cells Expressing CD28-Based Chimeric Antigen Receptors Circumvent CTLA-4 Inhibition. *PloS one*. 2015; 10(6):e0130518.
23. Hombach A A, Heiders J, Foppe M, Chmielewski M, and Abken H. OX40 costimulation by a chimeric antigen receptor abrogates CD28 and IL-2 induced IL-10 secretion by redirected CD4(+) T cells. *Oncoimmunology*. 2012; 1(4):458-66.
24. Hombach A A, Rappl G, and Abken H. Arming cytokine-induced killer cells with chimeric antigen receptors: CD28 outperforms combined CD28-OX40 "super-stimulation". *Molecular therapy: the journal of the American Society of Gene Therapy*. 2013; 21(12):2268-77.
25. Zhong X S, Matsushita M, Plotkin J, Riviere I, and Sadelain M. Chimeric antigen receptors combining 4-1BB and CD28 signaling domains augment PI3kinase/AKT/Bcl-XL activation and CD8+ T cell-mediated tumor eradication. *Molecular therapy: the journal of the American Society of Gene Therapy*. 2010; 18(2):413-20.
26. Long A H, Haso W M, Shern J F, Wanhainen K M, Murgai M, Ingaramo M, Smith J P, Walker A J, Kohler M E, Venkateshwara V R, et al. 4-1BB costimulation ameliorates T cell exhaustion induced by tonic signaling of chimeric antigen receptors. *Nature medicine*. 2015; 21(6):581-90.
27. Klement M, Liu C, Loo B L, Choo A B, Ow D S, and Lee D Y. Effect of linker flexibility and length on the functionality of a cytotoxic engineered antibody fragment. *Journal of biotechnology*. 2015; 199(90-7.
28. Pule M A, Straathof K C, Dotti G, Heslop H E, Rooney C M, and Brenner M K. A chimeric T cell antigen receptor that augments cytokine release and supports clonal expansion of primary human T cells. *Molecular therapy: the journal of the American Society of Gene Therapy*. 2005; 12(5):933-41.
29. Perna S K, Pagliara D, Mahendravada A, Liu H, Brenner M K, Savoldo B, and Dotti G. Interleukin-7 mediates selective expansion of tumor-redirected cytotoxic T lymphocytes (CTLs) without enhancement of regulatory T-cell inhibition. *Clinical cancer research: an official journal of the American Association for Cancer Research*. 2014; 20(1):131-9.
30. Cieri N, Camisa B, Cocchiarella F, Forcato M, Oliveira G, Provasi E, Bondanza A, Bordignon C, Peccatori J, Ciceri F, et al. IL-7 and IL-15 instruct the generation of human memory stem T cells from naive precursors. *Blood*. 2013; 121(4):573-84.
31. Singh H, Figliola M J, Dawson M J, Olivares S, Zhang L, Yang G, Maiti S, Manuri P, Senyukov V, Jena B, et al. Manufacture of clinical-grade CD19-specific T cells stably expressing chimeric antigen receptor using Sleeping Beauty system and artificial antigen presenting cells. *PloS one*. 2013; 8(5):e64138.
32. Zheng Z, Chinnasamy N, and Morgan R A. Protein L: a novel reagent for the detection of chimeric antigen receptor (CAR) expression by flow cytometry. *Journal of translational medicine*. 2012; 10(29.

---

SEQUENCE LISTING

```
<160> NUMBER OF SEQ ID NOS: 43

<210> SEQ ID NO 1
<211> LENGTH: 19
<212> TYPE: PRT
<213> ORGANISM: Artificial Sequence
<220> FEATURE:
<223> OTHER INFORMATION: signal peptide

<400> SEQUENCE: 1

Met Glu Phe Gly Leu Ser Trp Leu Phe Leu Val Ala Ile Leu Lys Gly
1               5                   10                  15

Val Gln Cys

<210> SEQ ID NO 2
<211> LENGTH: 111
<212> TYPE: PRT
<213> ORGANISM: Artificial Sequence
<220> FEATURE:
<223> OTHER INFORMATION: AC10 VL sequence

<400> SEQUENCE: 2

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
```

```
                    20                  25                  30

Gly Asp Ser Tyr Met Asn Trp Tyr Gln Gln Lys Pro Gly Gln Pro Pro
                35                  40                  45

Lys Val Leu Ile Tyr Ala Ala Ser Asn Leu Glu Ser Gly Ile Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln Gln Ser Asn
                85                  90                  95

Glu Asp Pro Trp Thr Phe Gly Gly Gly Thr Lys Leu Glu Ile Lys
                100                 105                 110

<210> SEQ ID NO 3
<211> LENGTH: 117
<212> TYPE: PRT
<213> ORGANISM: Artificial Sequence
<220> FEATURE:
<223> OTHER INFORMATION: AC10 VH sequence

<400> SEQUENCE: 3

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
                20                  25                  30

Tyr Ile Thr Trp Val Lys Gln Lys Pro Gly Gln Gly Leu Glu Trp Ile
                35                  40                  45

Gly Trp Ile Tyr Pro Gly Ser Gly Asn Thr Lys Tyr Asn Glu Lys Phe
 50                  55                  60

Lys Gly Lys Ala Thr Leu Thr Val Asp Thr Ser Ser Ser Thr Ala Phe
 65                  70                  75                  80

Met Gln Leu Ser Ser Leu Thr Ser Glu Asp Thr Ala Val Tyr Phe Cys
                85                  90                  95

Ala Asn Tyr Gly Asn Tyr Trp Phe Ala Tyr Trp Gly Gln Gly Thr Gln
                100                 105                 110

Val Thr Val Ser Ala
        115

<210> SEQ ID NO 4
<211> LENGTH: 16
<212> TYPE: PRT
<213> ORGANISM: Artificial Sequence
<220> FEATURE:
<223> OTHER INFORMATION: trackable marker DeltaCD34

<400> SEQUENCE: 4

Glu Leu Pro Thr Gln Gly Thr Phe Ser Asn Val Ser Thr Asn Val Ser
1               5                   10                  15

<210> SEQ ID NO 5
<211> LENGTH: 272
<212> TYPE: PRT
<213> ORGANISM: Artificial Sequence
<220> FEATURE:
<223> OTHER INFORMATION: trackable marker DeltaCD19

<400> SEQUENCE: 5

Pro Glu Glu Pro Leu Val Val Lys Val Glu Glu Gly Asp Asn Ala Val
1               5                   10                  15

Leu Gln Cys Leu Lys Gly Thr Ser Asp Gly Pro Thr Gln Gln Leu Thr
                20                  25                  30
```

Trp Ser Arg Glu Ser Pro Leu Lys Pro Phe Leu Lys Leu Ser Leu Gly
            35                  40                  45

Leu Pro Gly Leu Gly Ile His Met Arg Pro Leu Ala Ile Trp Leu Phe
    50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
                85                  90                  95

Glu Gly Ser Gly Glu Leu Phe Arg Trp Asn Val Ser Asp Leu Gly Gly
            100                 105                 110

Leu Gly Cys Gly Leu Lys Asn Arg Ser Ser Glu Gly Pro Ser Ser Pro
        115                 120                 125

Ser Gly Lys Leu Met Ser Pro Lys Leu Tyr Val Trp Ala Lys Asp Arg
    130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
            180                 185                 190

Leu Ser Trp Thr His Val His Pro Lys Gly Pro Lys Ser Leu Leu Ser
        195                 200                 205

Leu Glu Leu Lys Asp Asp Arg Pro Ala Arg Asp Met Trp Val Met Glu
    210                 215                 220

Thr Gly Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Ile Thr
                245                 250                 255

Ala Arg Pro Val Leu Trp His Trp Leu Leu Arg Thr Gly Gly Trp Lys
            260                 265                 270

<210> SEQ ID NO 6
<211> LENGTH: 222
<212> TYPE: PRT
<213> ORGANISM: Artificial Sequence
<220> FEATURE:
<223> OTHER INFORMATION: trackable marker NGFR

<400> SEQUENCE: 6

Lys Glu Ala Cys Pro Thr Gly Leu Tyr Thr His Ser Gly Glu Cys Cys
1               5                   10                  15

Lys Ala Cys Asn Leu Gly Glu Gly Val Ala Gln Pro Cys Gly Ala Asn
            20                  25                  30

Gln Thr Val Cys Glu Pro Cys Leu Asp Ser Val Thr Phe Ser Asp Val
        35                  40                  45

Val Ser Ala Thr Glu Pro Cys Lys Pro Cys Thr Glu Cys Val Gly Leu
    50                  55                  60

Gln Ser Met Ser Ala Pro Cys Val Glu Ala Asp Asp Ala Val Cys Arg
65                  70                  75                  80

Cys Ala Tyr Gly Tyr Tyr Gln Asp Glu Thr Thr Gly Arg Cys Glu Ala
                85                  90                  95

Cys Arg Val Cys Glu Ala Gly Ser Gly Leu Val Phe Ser Cys Gln Asp
            100                 105                 110

Lys Gln Asn Thr Val Cys Glu Glu Cys Pro Asp Gly Thr Tyr Ser Asp
        115                 120                 125

```
Glu Ala Asn His Val Asp Pro Cys Leu Pro Cys Thr Val Cys Glu Asp
            130                 135                 140

Thr Glu Arg Gln Leu Arg Gly Cys Thr Arg Trp Ala Asp Ala Glu Cys
145                 150                 155                 160

Glu Glu Ile Pro Gly Arg Trp Ile Thr Arg Ser Thr Pro Glu Gly
                165                 170                 175

Ser Asp Ser Thr Ala Pro Ser Thr Gln Glu Pro Glu Ala Pro Pro Glu
            180                 185                 190

Gln Asp Leu Ile Ala Ser Thr Val Ala Gly Val Val Thr Thr Val Met
            195                 200                 205

Gly Ser Ser Gln Pro Val Val Thr Arg Gly Thr Thr Asp Asn
            210                 215                 220

<210> SEQ ID NO 7
<211> LENGTH: 40
<212> TYPE: PRT
<213> ORGANISM: Artificial Sequence
<220> FEATURE:
<223> OTHER INFORMATION: hinge CD8alpha

<400> SEQUENCE: 7

Pro Ala Pro Arg Pro Pro Thr Pro Ala Pro Thr Ile Ala Ser Gln Pro
1               5                   10                  15

Leu Ser Leu Arg Pro Glu Ala Cys Arg Pro Ala Ala Gly Gly Ala Val
            20                  25                  30

His Thr Arg Gly Leu Asp Phe Ala
            35                  40

<210> SEQ ID NO 8
<211> LENGTH: 39
<212> TYPE: PRT
<213> ORGANISM: Artificial Sequence
<220> FEATURE:
<223> OTHER INFORMATION: hinge CD28

<400> SEQUENCE: 8

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
            35

<210> SEQ ID NO 9
<211> LENGTH: 229
<212> TYPE: PRT
<213> ORGANISM: Artificial Sequence
<220> FEATURE:
<223> OTHER INFORMATION: hinge CH2CH3

<400> SEQUENCE: 9

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
50                  55                  60
```

```
Glu Val His Asn Ala Lys Thr Lys Pro Arg Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 10
<211> LENGTH: 119
<212> TYPE: PRT
<213> ORGANISM: Artificial Sequence
<220> FEATURE:
<223> OTHER INFORMATION: hinge CH3

<400> SEQUENCE: 10

Glu Ser Lys Tyr Gly Pro Pro Cys Pro Ser Cys Pro Gly Gln Pro Arg
 1               5                  10                  15

Glu Pro Gln Val Tyr Thr Leu Pro Pro Ser Gln Glu Glu Met Thr Lys
                 20                  25                  30

Asn Gln Val Ser Leu Thr Cys Leu Val Lys Gly Phe Tyr Pro Ser Asp
             35                  40                  45

Ile Ala Val Glu Trp Glu Ser Asn Gly Gln Pro Glu Asn Asn Tyr Lys
         50                  55                  60

Thr Thr Pro Pro Val Leu Asp Ser Asp Gly Ser Phe Phe Leu Tyr Ser
 65                  70                  75                  80

Arg Leu Thr Val Asp Lys Ser Arg Trp Gln Glu Gly Asn Val Phe Ser
                 85                  90                  95

Cys Ser Val Met His Glu Ala Leu His Asn His Tyr Thr Gln Lys Ser
            100                 105                 110

Leu Ser Leu Ser Leu Gly Lys
        115

<210> SEQ ID NO 11
<211> LENGTH: 11
<212> TYPE: PRT
<213> ORGANISM: Artificial Sequence
<220> FEATURE:
<223> OTHER INFORMATION: spacer

<400> SEQUENCE: 11

Pro Ala Pro Arg Pro Pro Thr Pro Ala Pro Thr
 1               5                  10
```

<210> SEQ ID NO 12
<211> LENGTH: 29
<212> TYPE: PRT
<213> ORGANISM: Artificial Sequence
<220> FEATURE:
<223> OTHER INFORMATION: hinge CD8alpha

<400> SEQUENCE: 12

Ile Ala Ser Gln Pro Leu Ser Leu Arg Pro Glu Ala Cys Arg Pro Ala
1               5                   10                  15

Ala Gly Gly Ala Val His Thr Arg Gly Leu Asp Phe Ala
            20                  25

<210> SEQ ID NO 13
<211> LENGTH: 27
<212> TYPE: PRT
<213> ORGANISM: Artificial Sequence
<220> FEATURE:
<223> OTHER INFORMATION: trans membrane domain CD28TM

<400> SEQUENCE: 13

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 14
<211> LENGTH: 23
<212> TYPE: PRT
<213> ORGANISM: Artificial Sequence
<220> FEATURE:
<223> OTHER INFORMATION: trans membrane domain CD8aTM

<400> SEQUENCE: 14

Cys Asp Ile Tyr Ile Trp Ala Pro Leu Ala Gly Thr Cys Gly Val Leu
1               5                   10                  15

Leu Leu Ser Leu Val Ile Thr
            20

<210> SEQ ID NO 15
<211> LENGTH: 10
<212> TYPE: PRT
<213> ORGANISM: Artificial Sequence
<220> FEATURE:
<223> OTHER INFORMATION: mouse igG3 upper hinge (mIgG3UH)

<400> SEQUENCE: 15

Pro Lys Pro Ser Thr Pro Pro Gly Ser Ser
1               5                   10

<210> SEQ ID NO 16
<211> LENGTH: 20
<212> TYPE: PRT
<213> ORGANISM: Artificial Sequence
<220> FEATURE:
<223> OTHER INFORMATION: mouse igG3 upper hinge (mIgG3UH)2

<400> SEQUENCE: 16

Pro Lys Pro Ser Thr Pro Pro Gly Ser Ser Pro Lys Pro Ser Thr Pro
1               5                   10                  15

Pro Gly Ser Ser
            20

-continued

```
<210> SEQ ID NO 17
<211> LENGTH: 9
<212> TYPE: PRT
<213> ORGANISM: Artificial Sequence
<220> FEATURE:
<223> OTHER INFORMATION: (G4S)2 linker

<400> SEQUENCE: 17

Gly Gly Gly Gly Ser Gly Gly Gly Gly
1               5

<210> SEQ ID NO 18
<211> LENGTH: 20
<212> TYPE: PRT
<213> ORGANISM: Artificial Sequence
<220> FEATURE:
<223> OTHER INFORMATION: (G4S)4 linker

<400> SEQUENCE: 18

Gly Gly Gly Gly Ser Gly Gly Gly Gly Ser Gly Gly Gly Gly Ser Gly
1               5                   10                  15

Gly Gly Gly Ser
            20

<210> SEQ ID NO 19
<211> LENGTH: 7
<212> TYPE: PRT
<213> ORGANISM: Artificial Sequence
<220> FEATURE:
<223> OTHER INFORMATION: G4SG2 linker

<400> SEQUENCE: 19

Gly Gly Gly Gly Ser Gly Gly
1               5

<210> SEQ ID NO 20
<211> LENGTH: 8
<212> TYPE: PRT
<213> ORGANISM: Artificial Sequence
<220> FEATURE:
<223> OTHER INFORMATION: G3SG4 linker

<400> SEQUENCE: 20

Gly Gly Gly Ser Gly Gly Gly Gly
1               5

<210> SEQ ID NO 21
<211> LENGTH: 41
<212> TYPE: PRT
<213> ORGANISM: Artificial Sequence
<220> FEATURE:
<223> OTHER INFORMATION: CD28 cytoplasmic sequence

<400> SEQUENCE: 21

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 22
<211> LENGTH: 42
<212> TYPE: PRT
<213> ORGANISM: Artificial Sequence
<220> FEATURE:
```

<223> OTHER INFORMATION: CD137 (4-1BB) sequence

<400> SEQUENCE: 22

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 23
<211> LENGTH: 112
<212> TYPE: PRT
<213> ORGANISM: Artificial Sequence
<220> FEATURE:
<223> OTHER INFORMATION: CD3-Zeta chain

<400> SEQUENCE: 23

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 24
<211> LENGTH: 36
<212> TYPE: PRT
<213> ORGANISM: Artificial Sequence
<220> FEATURE:
<223> OTHER INFORMATION: OX40 sequence

<400> SEQUENCE: 24

Arg Asp Gln Arg Leu Pro Pro Asp Ala His Lys Pro Pro Gly Gly Gly
1               5                   10                  15

Ser Phe Arg Thr Pro Ile Gln Glu Glu Gln Ala Asp Ala His Ser Thr
            20                  25                  30

Leu Ala Lys Ile
        35

<210> SEQ ID NO 25
<211> LENGTH: 7
<212> TYPE: PRT
<213> ORGANISM: Artificial Sequence
<220> FEATURE:
<223> OTHER INFORMATION: CD8a cytoplasmic

<400> SEQUENCE: 25

Leu Tyr Cys Asn His Arg Asn
1               5

<210> SEQ ID NO 26
<211> LENGTH: 542

```
<212> TYPE: PRT
<213> ORGANISM: Artificial Sequence
<220> FEATURE:
<223> OTHER INFORMATION: CD30 chimeric antigen receptor molecule

<400> SEQUENCE: 26

Met Glu Phe Gly Leu Ser Trp Leu Phe Leu Val Ala Ile Leu Lys Gly
1               5                   10                  15

Val Gln Cys Ser Arg Asp Ile Val Leu Thr Gln Ser Pro Ala Ser Leu
            20                  25                  30

Ala Val Ser Leu Gly Gln Arg Ala Thr Ile Ser Cys Lys Ala Ser Gln
        35                  40                  45

Ser Val Asp Phe Asp Gly Asp Ser Tyr Met Asn Trp Tyr Gln Gln Lys
    50                  55                  60

Pro Gly Gln Pro Pro Lys Val Leu Ile Tyr Ala Ala Ser Asn Leu Glu
65                  70                  75                  80

Ser Gly Ile Pro Ala Arg Phe Ser Gly Ser Gly Ser Gly Thr Asp Phe
                85                  90                  95

Thr Leu Asn Ile His Pro Val Glu Glu Asp Ala Ala Thr Tyr Tyr
            100                 105                 110

Cys Gln Gln Ser Asn Glu Asp Pro Trp Thr Phe Gly Gly Gly Thr Lys
        115                 120                 125

Leu Glu Ile Lys Gly Gly Gly Ser Gly Gly Gly Gly Gln Ile Gln Leu
    130                 135                 140

Gln Gln Ser Gly Pro Glu Val Val Lys Pro Gly Ala Ser Val Lys Ile
145                 150                 155                 160

Ser Cys Lys Ala Ser Gly Tyr Thr Phe Thr Asp Tyr Tyr Ile Thr Trp
                165                 170                 175

Val Lys Gln Lys Pro Gly Gln Gly Leu Glu Trp Ile Gly Trp Ile Tyr
            180                 185                 190

Pro Gly Ser Gly Asn Thr Lys Tyr Asn Glu Lys Phe Lys Gly Lys Ala
        195                 200                 205

Thr Leu Thr Val Asp Thr Ser Ser Ser Thr Ala Phe Met Gln Leu Ser
210                 215                 220

Ser Leu Thr Ser Glu Asp Thr Ala Val Tyr Phe Cys Ala Asn Tyr Gly
225                 230                 235                 240

Asn Tyr Trp Phe Ala Tyr Trp Gly Gln Gly Thr Gln Val Thr Val Ser
                245                 250                 255

Ala Gly Ser Glu Leu Pro Thr Gln Gly Thr Phe Ser Asn Val Ser Thr
            260                 265                 270

Asn Val Ser Pro Ala Pro Arg Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Asn His Arg Asn Glu Phe Arg Ser Lys Arg Ser
            340                 345                 350

Arg Leu Leu His Ser Asp Tyr Met Asn Met Thr Pro Arg Arg Pro Gly
        355                 360                 365

Pro Thr Arg Lys His Tyr Gln Pro Tyr Ala Pro Pro Arg Asp Phe Ala
    370                 375                 380
```

```
Ala Tyr Arg Ser Lys Arg Gly Arg Lys Lys Leu Leu Tyr Ile Phe Lys
385                 390                 395                 400

Gln Pro Phe Met Arg Pro Val Gln Thr Thr Gln Glu Glu Asp Gly Cys
            405                 410                 415

Ser Cys Arg Phe Pro Glu Glu Glu Glu Gly Gly Cys Glu Leu Arg Val
            420                 425                 430

Lys Phe Ser Arg Ser Ala Asp Ala Pro Ala Tyr Gln Gln Gly Gln Asn
            435                 440                 445

Gln Leu Tyr Asn Glu Leu Asn Leu Gly Arg Arg Glu Glu Tyr Asp Val
    450                 455                 460

Leu Asp Lys Arg Arg Gly Arg Asp Pro Glu Met Gly Gly Lys Pro Arg
465                 470                 475                 480

Arg Lys Asn Pro Gln Glu Gly Leu Tyr Asn Glu Leu Gln Lys Asp Lys
            485                 490                 495

Met Ala Glu Ala Tyr Ser Glu Ile Gly Met Lys Gly Glu Arg Arg Arg
            500                 505                 510

Gly Lys Gly His Asp Gly Leu Tyr Gln Gly Leu Ser Thr Ala Thr Lys
            515                 520                 525

Asp Thr Tyr Asp Ala Leu His Met Gln Ala Leu Pro Pro Arg
    530                 535                 540

<210> SEQ ID NO 27
<211> LENGTH: 536
<212> TYPE: PRT
<213> ORGANISM: Artificial Sequence
<220> FEATURE:
<223> OTHER INFORMATION: CD30 chimeric antigen receptor molecule

<400> SEQUENCE: 27

Met Glu Phe Gly Leu Ser Trp Leu Phe Leu Val Ala Ile Leu Lys Gly
1               5                   10                  15

Val Gln Cys Ser Arg Asp Ile Val Leu Thr Gln Ser Pro Ala Ser Leu
            20                  25                  30

Ala Val Ser Leu Gly Gln Arg Ala Thr Ile Ser Cys Lys Ala Ser Gln
        35                  40                  45

Ser Val Asp Phe Asp Gly Asp Ser Tyr Met Asn Trp Tyr Gln Gln Lys
    50                  55                  60

Pro Gly Gln Pro Pro Lys Val Leu Ile Tyr Ala Ala Ser Asn Leu Glu
65                  70                  75                  80

Ser Gly Ile Pro Ala Arg Phe Ser Gly Ser Gly Ser Gly Thr Asp Phe
                85                  90                  95

Thr Leu Asn Ile His Pro Val Glu Glu Glu Asp Ala Ala Thr Tyr Tyr
            100                 105                 110

Cys Gln Gln Ser Asn Glu Asp Pro Trp Thr Phe Gly Gly Gly Thr Lys
        115                 120                 125

Leu Glu Ile Lys Gly Gly Gly Ser Gly Gly Gly Gly Gln Ile Gln Leu
130                 135                 140

Gln Gln Ser Gly Pro Glu Val Val Lys Pro Gly Ala Ser Val Lys Ile
145                 150                 155                 160

Ser Cys Lys Ala Ser Gly Tyr Thr Phe Thr Asp Tyr Tyr Ile Thr Trp
                165                 170                 175

Val Lys Gln Lys Pro Gly Gln Gly Leu Glu Trp Ile Gly Trp Ile Tyr
            180                 185                 190

Pro Gly Ser Gly Asn Thr Lys Tyr Asn Glu Lys Phe Lys Gly Lys Ala
        195                 200                 205
```

Thr Leu Thr Val Asp Thr Ser Ser Thr Ala Phe Met Gln Leu Ser
    210                 215                 220

Ser Leu Thr Ser Glu Asp Thr Ala Val Tyr Phe Cys Ala Asn Tyr Gly
225                 230                 235                 240

Asn Tyr Trp Phe Ala Tyr Trp Gly Gln Gly Thr Gln Val Thr Val Ser
                245                 250                 255

Ala Gly Ser Glu Leu Pro Thr Gln Gly Thr Phe Ser Asn Val Ser Thr
            260                 265                 270

Asn Val Ser Pro Ala Pro Arg Pro Thr Pro Ala Pro Thr Ile Ala
        275                 280                 285

Ser Gln Pro Leu Ser Leu Arg Pro Glu Ala Cys Arg Pro Ala Ala Gly
290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Asn His Arg Asn Glu Phe Arg Ser Lys Arg Ser
            340                 345                 350

Arg Leu Leu His Ser Asp Tyr Met Asn Met Thr Pro Arg Arg Pro Gly
                355                 360                 365

Pro Thr Arg Lys His Tyr Gln Pro Tyr Ala Pro Pro Arg Asp Phe Ala
370                 375                 380

Ala Tyr Arg Ser Arg Asp Gln Arg Leu Pro Pro Asp Ala His Lys Pro
385                 390                 395                 400

Pro Gly Gly Gly Ser Phe Arg Thr Pro Ile Gln Glu Glu Gln Ala Asp
                405                 410                 415

Ala His Ser Thr Leu Ala Lys Ile Arg Val Lys Phe Ser Arg Ser Ala
            420                 425                 430

Asp Ala Pro Ala Tyr Gln Gln Gly Gln Asn Gln Leu Tyr Asn Glu Leu
        435                 440                 445

Asn Leu Gly Arg Arg Glu Glu Tyr Asp Val Leu Asp Lys Arg Arg Gly
450                 455                 460

Arg Asp Pro Glu Met Gly Gly Lys Pro Arg Arg Lys Asn Pro Gln Glu
465                 470                 475                 480

Gly Leu Tyr Asn Glu Leu Gln Lys Asp Lys Met Ala Glu Ala Tyr Ser
                485                 490                 495

Glu Ile Gly Met Lys Gly Glu Arg Arg Arg Gly Lys Gly His Asp Gly
            500                 505                 510

Leu Tyr Gln Gly Leu Ser Thr Ala Thr Lys Asp Thr Tyr Asp Ala Leu
        515                 520                 525

His Met Gln Ala Leu Pro Pro Arg
530                 535

<210> SEQ ID NO 28
<211> LENGTH: 1629
<212> TYPE: DNA
<213> ORGANISM: Artificial Sequence
<220> FEATURE:
<223> OTHER INFORMATION: synthesized nucleotide sequence encoding CD30
      chimeric antigen receptor molecule

<400> SEQUENCE: 28
atggagtttg gctctcctg gctcttcctg gtcgcgattc tgaaggggt ccagtgttca      60 cgagatatcg tcctgactca gagtcctgcc agcctggcag tctccctggg acagagagct   120
accataagtt gtaaagcatc acagtctgtt gatttcgatg gcgacagcta tatgaattgg   180

```
taccagcaaa aacccggcca gcccccgaaa gttttgatct atgcagcctc taacttggaa      240
agcggcattc ctgcgcgatt cagtggcagc gggagtggta cagatttcac cctgaacata      300
cacccagtcg aagaggagga cgcagccaca tattactgcc aacaatctaa cgaggatcca      360 tggactttg ggggcggcac taaactcgaa atcaagggcg gaggttcagg cggaggaggg       420
cagattcaac tgcagcaatc aggacccgag gtggtcaaac caggtgccag tgtcaagata      480
tcttgcaagg catccggata cattactacc gactattaca ttacctgggt caagcagaaa     540
cccgggcaag acttgaatg gattggatgg atctaccctg gtagcggcaa caccaaatac       600
aacgaaaagt ttaagggaa ggcaaccctg actgtagaca cctccagctc acagcattc        660 atgcagctct cctcactgac ctccgaggac acagcagtgt atttctgtgc taattacggt      720
aattactggt tcgcctattg gggccaggga acccaagtga ccgtttcagc tggatccgaa      780
cttcctactc agggactttt tcaaacgtt agcacaaacg taagtcccgc ccaagaccc        840 cccacacctg cgccgaccat tgcttctcaa cccctgagtt tgagaccga ggcctgccgg       900 ccagctgccg gcggggccgt gcatacaaga ggactcgatt tcgcttgcga catctacatc      960
tgggctcccc tcgctggcac ctgtggggtg ctgctgctgt cactcgtgat cacccttat      1020 tgcaaccatc gaaacgaatt cagaagtaaa cggtcaaggc ttctgcacag cgattatatg     1080
aatatgacac caagaagacc tggtccaacc cggaaacact atcagcccta cgcgcccct     1140 agagacttcg cagcataccg ctctaagaga gggagaaaaa aattgctcta tattttaaa    1200 caaccattta tgaggcccgt acagacaact caggaagagg atggctgtag ttgccgcttc     1260
ccagaggagg aggaaggagg ctgcgagttg agagttaaat tcagtagaag tgcggatgcg      1320
cctgcttacc agcagggcca gaaccaactg tacaatgaac tgaatctcgg cgccgagaa      1380 gagtatgacg tcctcgataa gcggagggt agggatcctg aaatgggtgg gaagccaaga      1440
agaaaaaacc cccaggaagg actgtataac gaacttcaga aggacaagat ggcagaggcc     1500
tactctgaga ttggcatgaa aggcgaacga cggcgcggta aaggtcatga cgggctgtac      1560
cagggcctgt ccacagcgac gaaggacact tacgacgccc tgcacatgca ggcactcccc     1620
cccaggtga                                                              1629

<210> SEQ ID NO 29
<211> LENGTH: 63
<212> TYPE: DNA
<213> ORGANISM: Artificial Sequence
<220> FEATURE:
<223> OTHER INFORMATION: synthesized nucleotide sequence encoding signal
      peptide

<400> SEQUENCE: 29
atggagtttg ggctctcctg ctcttcctg gtcgcgattc tgaaggggt ccagtgttca       60 cga                                                                    63

<210> SEQ ID NO 30
<211> LENGTH: 333
<212> TYPE: DNA
<213> ORGANISM: Artificial Sequence
<220> FEATURE:
<223> OTHER INFORMATION: synthesized nucleotide sequence encoding AC10
      VL sequence

<400> SEQUENCE: 30
gatatcgtcc tgactcagag tcctgccagc ctggcagtct ccctgggaca gagagctacc      60
```

```
ataagttgta aagcatcaca gtctgttgat tcgatggcg acagctatat gaattggtac    120
cagcaaaaac ccggccagcc cccgaaagtt ttgatctatg cagcctctaa cttggaaagc   180
ggcattcctg cgcgattcag tggcagcggg agtggtacag atttcaccct gaacatacac   240
ccagtcgaag aggaggacgc agccacatat tactgccaac aatctaacga ggatccatgg   300
acttttgggg gcggcactaa actcgaaatc aag                                333
```

```
<210> SEQ ID NO 31
<211> LENGTH: 24
<212> TYPE: DNA
<213> ORGANISM: Artificial Sequence
<220> FEATURE:
<223> OTHER INFORMATION: synthesized nucleotide sequence encoding G3SG4
      linker

<400> SEQUENCE: 31
ggcggaggtt caggcggagg aggg                                          24
```

```
<210> SEQ ID NO 32
<211> LENGTH: 333
<212> TYPE: DNA
<213> ORGANISM: Artificial Sequence
<220> FEATURE:
<223> OTHER INFORMATION: synthesized nucleotide sequence encoding AC10
      VH sequence

<400> SEQUENCE: 32
gatatcgtcc tgactcagag tcctgccagc ctggcagtct ccctgggaca gagagctacc    60
ataagttgta aagcatcaca gtctgttgat tcgatggcg acagctatat gaattggtac    120
cagcaaaaac ccggccagcc cccgaaagtt ttgatctatg cagcctctaa cttggaaagc   180
ggcattcctg cgcgattcag tggcagcggg agtggtacag atttcaccct gaacatacac   240
ccagtcgaag aggaggacgc agccacatat tactgccaac aatctaacga ggatccatgg   300
acttttgggg gcggcactaa actcgaaatc aag                                333
```

```
<210> SEQ ID NO 33
<211> LENGTH: 6
<212> TYPE: DNA
<213> ORGANISM: Artificial Sequence
<220> FEATURE:
<223> OTHER INFORMATION: BamH1 restriction site

<400> SEQUENCE: 33 ggatcc                                                              6
```

```
<210> SEQ ID NO 34
<211> LENGTH: 48
<212> TYPE: DNA
<213> ORGANISM: Artificial Sequence
<220> FEATURE:
<223> OTHER INFORMATION: synthesized nucleotide sequence encoding
      trackable marker DeltaCD34

<400> SEQUENCE: 34
gaacttccta ctcaggggac tttctcaaac gttagcacaa acgtaagt                48
```

```
<210> SEQ ID NO 35
<211> LENGTH: 120
<212> TYPE: DNA
<213> ORGANISM: Artificial Sequence
<220> FEATURE:
<223> OTHER INFORMATION: synthesized nucleotide sequence encoding hinge
      CD8alpha
```

<400> SEQUENCE: 35
cccgccccaa gacccccac acctgcgccg accattgctt ctcaacccct gagtttgaga      60
cccgaggcct gccggccagc tgccggcggg gccgtgcata caagaggact cgatttcgct    120

<210> SEQ ID NO 36
<211> LENGTH: 69
<212> TYPE: DNA
<213> ORGANISM: Artificial Sequence
<220> FEATURE:
<223> OTHER INFORMATION: synthesized nucleotide sequence encoding trans
      membrane domain CD8aTM

<400> SEQUENCE: 36
tgcgacatct acatctgggc tcccctcgct ggcacctgtg gggtgctgct gctgtcactc     60
gtgatcacc                                                            69

<210> SEQ ID NO 37
<211> LENGTH: 21
<212> TYPE: DNA
<213> ORGANISM: Artificial Sequence
<220> FEATURE:
<223> OTHER INFORMATION: synthesized nucleotide sequence encoding CD8a
      cytoplasmic

<400> SEQUENCE: 37
ctttattgca accatcgaaa c                                              21

<210> SEQ ID NO 38
<211> LENGTH: 6
<212> TYPE: DNA
<213> ORGANISM: Artificial Sequence
<220> FEATURE:
<223> OTHER INFORMATION: EcoR1 restriction site and connection sequence

<400> SEQUENCE: 38 gaattc                                                                6

<210> SEQ ID NO 39
<211> LENGTH: 123
<212> TYPE: DNA
<213> ORGANISM: Artificial Sequence
<220> FEATURE:
<223> OTHER INFORMATION: synthesized nucleotide sequence encoding CD28
      cytoplasmic sequence

<400> SEQUENCE: 39
agaagtaaac ggtcaaggct tctgcacagc gattatatga atatgacacc aagaagacct     60
ggtccaaccc ggaaacacta tcagccctac gcgccccta gagacttcgc agcataccgc    120
tct                                                                 123

<210> SEQ ID NO 40
<211> LENGTH: 126
<212> TYPE: DNA
<213> ORGANISM: Artificial Sequence
<220> FEATURE:
<223> OTHER INFORMATION: synthesized nucleotide sequence encoding CD137
      (4-1BB) sequence

<400> SEQUENCE: 40
aagagaggga gaaaaaaatt gctctatatt tttaaacaac catttatgag gcccgtacag     60
acaactcagg aagaggatgg ctgtagttgc cgcttcccag aggaggagga aggaggctgc    120

<210> SEQ ID NO 41
<211> LENGTH: 339
<212> TYPE: DNA
<213> ORGANISM: Artificial Sequence
<220> FEATURE:
<223> OTHER INFORMATION: synthesized nucleotide sequence encoding CD3-Zeta chain

<400> SEQUENCE: 41

```
agagttaaat tcagtagaag tgcggatgcg cctgcttacc agcagggcca gaaccaactg      60
tacaatgaac tgaatctcgg cgccgagaa gagtatgacg tcctcgataa gcggaggggt     120
agggatcctg aaatgggtgg aagccaaga agaaaaaacc cccaggaagg actgtataac     180
gaacttcaga aggacaagat ggcagaggcc tactctgaga ttggcatgaa aggcgaacga     240
cggcgcggta aaggtcatga cgggctgtac cagggcctgt ccacagcgac gaaggacact     300
tacgacgccc tgcacatgca ggcactcccc cccaggtga                           339
```

<210> SEQ ID NO 42
<211> LENGTH: 1611
<212> TYPE: DNA
<213> ORGANISM: Artificial Sequence
<220> FEATURE:
<223> OTHER INFORMATION: synthesized nucleotide sequence encoding CD30 chimeric antigen receptor molecule

<400> SEQUENCE: 42

```
atggagtttg ggctctcctg gctcttcctg gtcgcgattc tgaaggggt ccagtgttca       60
cgagatatcg tcctgactca gagtcctgcc agcctggcag tctccctggg acagagagct     120
accataagtt gtaaagcatc acagtctgtt gatttcgatg cgacagcta tatgaattgg     180
taccagcaaa aacccggcca gcccccgaaa gttttgatct atgcagcctc taacttggaa     240
agcggcattc ctgcgcgatt cagtggcagc gggagtggta cagatttcac cctgaacata     300
cacccagtcg aagaggagga cgcagccaca tattactgcc aacaatctaa cgaggatcca     360
tggactttg ggggcggcac taaactcgaa atcaagggcg aggttcagg cggaggaggg      420
cagattcaac tgcagcaatc aggacccgag gtggtcaaac caggtgccag tgtcaagata     480
tcttgcaagg catccggata cattaccc gactattaca ttacctgggt caagcagaaa      540
cccgggcaag gacttgaatg gattggatgg atctaccctg gtagcggcaa caccaaaatac    600
aacgaaaagt ttaaagggaa ggcaacccctg actgtagaca cctccagctc cacagcattc     660
atgcagctct cctcactgac ctccgaggac acagcagtgt atttctgtgc taattacggt     720
aattactggt cgcctattg gggccaggga acccaagtga ccgtttcagc tggatccgaa      780
cttcctactc aggggacttt ctcaaacgtt agcacaaacg taagtcccgc ccaagaccc      840
cccacacctg cgccgaccat tgcttctcaa ccctgagtt tgagacccga ggcctgccgg      900
ccagctgccg gcgggccgt gcatacaaga ggactcgatt tcgcttgcga catctacatc      960
tgggctcccc tcgctggcac ctgtggggtg ctgctgctgt cactcgtgat caccctttat    1020
tgcaaccatc gaaacgaatt cagaagtaaa cggtcaaggc ttctgcacag cgattatatg    1080
aatatgacac caagaagacc tggtccaacc cggaaacact atcagccta cgcgcccct    1140
agagacttcg cagcataccg ctctcgcgat caaagactcc cgcccgatgc ccacaaaccc    1200
cctggcgggg gcagctttag gacacccatt caagaagagc aggcagacgc ccacagcacc    1260
ttggccaaaa ttagagttaa attcagtaga agtgcggatg cgcctgctta ccagcagggc    1320
```

```
cagaaccaac tgtacaatga actgaatctc gggcgccgag aagagtatga cgtcctcgat    1380
aagcggaggg gtagggatcc tgaaatgggt gggaagccaa gaagaaaaaa cccccaggaa    1440
ggactgtata acgaacttca gaaggacaag atggcagagg cctactctga gattggcatg    1500
aaaggcgaac gacggcgcgg taaaggtcat gacgggctgt accagggcct gtccacagcg    1560
acgaaggaca cttacgacgc cctgcacatg caggcactcc ccccaggtg a              1611

<210> SEQ ID NO 43
<211> LENGTH: 108
<212> TYPE: DNA
<213> ORGANISM: Artificial Sequence
<220> FEATURE:
<223> OTHER INFORMATION: synthesized nucleotide sequence encoding OX40
      sequence

<400> SEQUENCE: 43
cgcgatcaaa gactcccgcc cgatgccac aaaccccctg gcgggggcag ctttaggaca     60
cccattcaag aagagcaggc agacgcccac agcaccttgg ccaaaatt                 108
```

What is claimed is:

1. A CD30 chimeric antigen receptor comprising, from the N-terminus to the C- terminus:
   a) a signal peptide, which is linked by a first linker to;
   b) an anti CD30 single chain antibody domain from AC10 hybridoma comprising the AC10 VL sequence: DIVLTQSPASLAVSLGQRATISCK-ASQSVDFDGDSYMNWYQQKPGQPPKVLIY AASNLESGI-PARFSGSGSGTDFTLNIHPVEEEDAATYYCQQS NEDPWTFGGGTKLEIK (SEQ ID NO:2) and AC10 VH sequence: QIQLQQSGPEVVKPGASVKISCK-ASGYTFTDYYITWVKQKPGQGLEWIGWIYP GSGNT-KYNEKFKGKATLTVDTSSSTAFMQLSSLTSED-TAVYFCANYGNYWFAYWGQG TQVTVSA (SEQ ID NO: 3), said AC10 VL and VH sequences being linked by a second linker;
   c) a trackable marker selected from the group consisting of ΔCD34:ELPTQGTFSNVSTNVS (SEQ ID NO:4), ΔCD19:PEEPLVVKVEEGD-NAVLQCLKGTSDGPTQQLTWSRESPLKP-FLKLSLGLPGLGIH MRPLAIWLFIFNVSQQMGGFYL-CQPGPPSEKAWQPGWTVNVEGSGEL-FRWNVSDLGGL GCGLKNRSSEGPSSPSGKLMSPKLYVWAKDR-PEIWEGEPPCLPPRDSLNQSLSQDLTMA PGSTLWLSCGVPPDSVSRG-PLSWTHVHPKGPKSLLSLELKDDR-PARDMWVMETGLLLP RATAQDAGKYY-CHRGNLTMSFHLEITARPVLHWLLRTGGWK (SEQ ID NO:5); NGFR:KEACPTGLYTHSGECCK-ACNLGEGVAQPCGANQTV-CEPCLDSVTFSDVVSATEP CKPCTECVGLQSM-SAPCVEADDAVCRCAYGYYQDETTGRCEACRV CEAGSGLVFSCQ DKQNTVCEECPDGTYS-DEANHVDPCLPCTVCEDTERQLRECTRWADAE-CEEIPGRWITR STPPEGSDSTAPSTQEPE-APPEQDLIASTVAGVVTTVMGSSQPVVTRGTTD-N (SEQ ID NO:6);
   d) a hinge selected from the group consisting of hinge CD8α PAPRPPTPAPTIASQPLSLRPEACR-PAAGGAVHTRGLDFA (SEQ ID NO:7), hinge CD28: IEVMYPPPYLD-NEKSNGTIIHVKGKHLCPSPLFPGPSKP (SEQ ID NO:8), hinge CH2-CH3: ESKYGPPCPSCPAPE-FLGGPSVFLFPPKPKDTLMISRTPE-VTCVVVDVSQEDPEVQFNWY VDGVEVHNAKTKPREEQFN-STYRVVSVLTVLHQDWLNGKEYKCKVSNKGLP-SSIEKTIS KAKGQPREPQVYTLPPSQEEMT-KNQVSLTCLVKGFYPSDIAVEWESNGQPEN-NYKTTPP VLDSDGSFFLY-SRLTVDKSRWQEGNVFSCSVMHEALHNHYTQK-SLSLSLGK (SEQ ID NO:9), hinge CH3: ESKY-GPPCPSCPGQPREPQVYTLPPSQEEMTKNQVSLT-CLVKGFYPSDIAVEWESNGQPE NNYKTTPPVLDSDGSFFLY-SRLTVDKSRWQEGNVFSCSVMHEALHN-HYTQKSLSLSLG K (SEQ ID NO:10);
   e) a transmembrane domain selected from the group consisting of CD28TM: FWVLVVVGGVLACYSLL-VTVAFIIFWV (SEQ ID NO:13), CD8aTM CDIYI-WAPLAGTCGVLLLSLVIT (SEQ ID NO:14); and
   f) a co-stimulatory signaling domain consisting of the sequence obtained by linking CD28 cytoplasmic sequence RSKRSRLLHSDYMNMTPRRPGP-TRKHYQPYAPPRDFAAYRS (SEQ ID NO:21), OX40 sequence RDQRLPPDAHKPPGGGSFRT-PIQEEQADAHSTLAKI (SEQ ID NO:24) and CD3Zeta chain RVKFSRSADAPAYQQGQNQLY-NELNLGRREEYDVLDKRR-GRDPEMGGKPRRKNPQEG LYNELQKDK-MAEAYSEIGMKGERRRGKGHDGLYQGLSTATK-DTYDALHMQALPPR (SEQ ID NO:23).

2. The CD30 chimeric antigen receptor according to claim 1, wherein the second linker which links AC10 VL and VH sequences is selected from the group consisting of a rigid proline-rich linker or a flexible glycine-rich linker.

3. The CD30 chimeric antigen receptor according to claim 1, wherein the AC10 VH sequence and the trackable marker sequence are linked by a third linker of sequence GS.

4. The CD30 chimeric antigen receptor according to claim 1, wherein the transmembrane domain sequence and costimulatory signalling domain sequence are linked by one or more linkers, which comprise CD8a cytoplasmic sequence (cyto): LYCNHRN (SEQ ID NO:25) or EF.

5. A CD30 chimeric antigen receptor according to claim 1, wherein the signal peptide comprises the sequence MEFGLSWLFLVAILKGVQC (SEQ ID NO:1).

6. The CD30 chimeric antigen receptor according to claim 1, comprising:
   a) the signal peptide comprises MEFGLSWLFLVAILKGVQC (SEQ ID NO:1), which is linked by a first linker to;
   b) an anti CD30 single chain antibody domain from AC10 hybridoma comprising the AC10 VL sequence DIVLTQSPASLAVSLGQRATISCK-ASQSVDFDGDSYMNWYQQKPGQPPKVLI-YAASNLE SGI-PARFSGSGSGTDFTLNIHPVEEEDAATYYCQQS-NEDPWTFGGGTKLEIK (SEQ ID NO:2) and AC10 VH sequence QIQLQQSGPEVVKPGASVKISCK-ASGYTFTDYYITWVKQKPGQ-GLEWIGWIYPGSGN TKYNEKFKGKATLTVDTSSSTAFMQLSSLTSED-TAVYFCANYGNYWFAYWGQGTQVT VSA (SEQ ID NO: 3), said AC10 VL and VH sequences being linked by the second linker (G4S)2 linker GGGGSGGGG (SEQ ID NO:17);
   c) a trackable marker comprising ΔCD34 ELPTQGTFSNVSTNVS (SEQ ID NO:4);
   d) the hinge CD8α PAPRPPTPAPTIASQPLSLRPEACR-PAAGGAVHTRGLDFA (SEQ ID NO:7);
   e) the transmembrane domain CD8aTM CDIYI-WAPLAGTCGVLLLSLVIT (SEQ ID NO:14), which is linked by one or more linkers, which comprise the linker CD8a cytoplasmic sequence (cyto) LYCNHRN (SEQ ID NO:25), to
   f) the co-stimulatory signalling domain consisting of the sequence obtained by linking CD28 cytoplasmic sequence RSKRSRLLHSDYMNMTPRRPGP-TRKHYQPYAPPRDFAAYRS (SEQ ID NO:21), OX40 sequence RDQRLPPDAHKPPGGGSFRT-PIQEEQADAHSTLAKI (SEQ ID NO:24) and CD3Zeta chain RVKFSRSADAPAYQQGQNQLY-NELNLGRREEYDVLDKRR-GRDPEMGGKPRRKNPQEG LYNELQKDK-MAEAYSEIGMKGERRRGKGHDGLYQGLSTATK-DTYDALHMQALPPR (SEQ ID NO:23).

7. The CD30 chimeric antigen receptor according to claim 1, wherein the second linker which links AC10 VL and VH sequences is mouse IgG3 upper hinge (mIgG3UH): PKP-STPPGSS (SEQ ID NO:15) or (mIgG3UH)₂: PKP-STPPGSSPKPSTPPGSS (SEQ ID NO:16).

8. The CD30 chimeric antigen receptor according to claim 1, wherein the second linker which links AC10 VL and VH sequences is (G4S)2 linker: GGGGSGGGG (SEQ ID NO:17), (G4S)4 linker: GGGGSGGGGSGGGGSGGGGS (SEQ ID NO:18), G4SG2 linker GGGGSGG (SEQ ID NO:19), or G3SG4 linker: GGGSGGGG (SEQ ID NO:20).

9. The CD30 chimeric antigen receptor according to claim 1, wherein said CD30 chimeric antigen receptor is (SEQ ID NO: 27)
MEFGLSWLFLVAILKGVQCSRDIVLTQSPASLAVSLGQRATISCKASQSV

DFDGDSYMNWYQQKPGQPPKVLIYAASNLESGIPARFSGSGSGTDFTLNI

HPVEEEDAATYYCQQSNEDPWTFGGGTKLEIKGGGSGGGGQIQLQQSGPE

-continued
VVKPGASVKISCKASGYTFTDYYITWVKQKPGQGLEWIGWIYPGSGNTKY

NEKFKGKATLTVDTSSSTAFMQLSSLTSEDTAVYFCANYGNYWFAYWGQG

TQVTVSAGSELPTQGTFSNVSTNVSPAPRPPTPAPTIASQPLSLRPEACR

PAAGGAVHTRGLDFACDIYIWAPLAGTCGVLLLSLVITLYCNHRNEFRSK

RSRLLHSDYMNMTPRRPGPTRKHYQPYAPPRDFAAYRSRDQRLPPDAHKP

PGGGSFRTPIQEEQADAHSTLAKIRVKFSRSADAPAYQQGQNQLYNELNL

GRREEYDVLDKRRGRDPEMGGKPRRKNPQEGLYNELQKDKMAEAYSEIGM

KGERRRGKGHDGLYQGLSTATKDTYDALHMQALPPR.

10. A nucleotide sequence which encodes the CD30 chimeric antigen receptor according to claim 1.

11. The nucleotide sequence according to claim 10, which is (SEQ ID NO: 42)
ATGGAGTTTGGGCTCTCCTGGCTCTTCCTGGTCGCGATTCTGAAGGGGGT

CCAGTGTTCACGAGATATCGTCCTGACTCAGAGTCCTGCCAGCCTGGCAG

TCTCCCTGGGACAGAGAGCTACCATAAGTTGTAAAGCATCACAGTCTGTT

GATTTCGATGGCGACAGCTATATGAATTGGTACCAGCAAAAACCCGGCCA

GCCCCCGAAAGTTTTGATCTATGCAGCCTCTAACTTGGAAAGCGGCATTC

CTGCGCGATTCAGTGGCAGCGGGAGTGGTACAGATTTCACCCTGAACATA

CACCCAGTCGAAGAGGAGGACGCAGCCACATATTACTGCCAACAATCTAA

CGAGGATCCATGGACTTTTGGGGGCGGCACTAAACTCGAAATCAAGGGCG

GAGGTTCAGGCGGAGGAGGGCAGATTCAACTGCAGCAATCAGGACCCGAG

GTGGTCAAACCAGGTGCCAGTGTCAAGATATCTTGCAAGGCATCCGGATA

TACATTTACCGACTATTACATTACCTGGGTCAAGCAGAAACCCGGGCAAG

GACTTGAATGGATTGGATGGATCTACCCTGGTAGCGGCAACACCAAATAC

AACGAAAAGTTTAAAGGGAAGGCAACCCTGACTGTAGACACCTCCAGCTC

CACAGCATTCATGCAGCTCTCCTCACTGACCTCCGAGGACACAGCAGTGT

ATTTCTGTGCTAATTACGGTAATTACTGGTTCGCCTATTGGGGCCAGGGA

ACCCAAGTGACCGTTTCAGCTGGATCCGAACTTCCTACTCAGGGGACTTT

CTCAAACGTTAGCACAAACGTAAGTCCCGCCCCAAGACCCCCCACACCTG

CGCCGACCATTGCTTCTCAACCCCTGAGTTTGAGACCCGAGGCCTGCCGG

CCAGCTGCCGGCGGGCCGTGCATACAAGAGGACTCGATTTCGCTTGCGA

CATCTACATCTGGGCTCCCCTCGCTGGCACCTGTGGGGTGCTGCTGCTGT

CACTCGTGATCACCCTTTATTGCAACCATCGAAACGAATTCAGAAGTAAA

CGGTCAAGGCTTCTGCACAGCGATTATATGAATATGACACCAAGAAGACC

TGGTCCAACCCGGAAACACTATCAGCCCTACGCGCCCCCTAGAGACTTCG

CAGCATACCGCTCTCGCGATCAAAGACTCCCGCCCGATGCCCACAAACCC

CCTGGCGGGGCAGCTTTAGGACACCCATTCAAGAAGAGCAGGCAGACGC

CCACAGCACCTTGGCCAAAATTAGAGTTAAATTCAGTAGAAGTGCGGATG

CGCCTGCTTACCAGCAGGGCCAGAACCAACTGTACAATGAACTGAATCTC

GGGCGCCGAGAAGAGTATGACGTCCTCGATAAGCGGAGGGGTAGGGATCC

TGAAATGGGTGGGAAGCCAAGAAGAAAAAACCCCCAGGAAGGACTGTATA

-continued

ACGAACTTCAGAAGGACAAGATGGCAGAGGCCTACTCTGAGATTGGCATG

AAAGGCGAACGACGGCGCGGTAAAGGTCATGACGGGCTGTACCAGGGCCT

GTCCACAGCGACGAAGGACACTTACGACGCCCTGCACATGCAGGCACTCC

CCCCCAGGTGA.

12. A vector comprising the nucleotide sequence according to claim 10, wherein said vector is a DNA vector, a RNA vector, a plasmid, a lentivirus vector, adenoviral vector, retrovirus vector or non-viral vector.

13. A cell, comprising the vector according to claim 12.

14. The cell according to claim 13, which is obtained in culture conditions where both IL-7 and IL-15 are present.

15. The cell according to claim 13, wherein the cell is obtained in a culture condition where both IL-7 and IL-15 are present, comprising processes of activation, transduction, and/or expansion to prepare the cell.

16. A pharmaceutical composition comprising the nucleotide sequence according to claim 10 together with one or more excipients and/or adjuvants.

17. A method of treating a CD30+ cancer in a subject in need thereof, comprising administering the nucleotide sequence according to claim 10 to the subject.

18. A method of treating a CD30+ cancer in a subject in need thereof, comprising administering the CD30 chimeric antigen receptor according to claim 1 to the subject.

19. The method according to claim 18, wherein the CD30+ cancer is a CD30+PDL1+ cancer.

20. The method according to claim 19, wherein the CD30+PDL1+ cancer is a L428-PDL1+ cancer.

21. The method according to claim 20, wherein the L428-PDL1+ cancer is selected from the group consisting of Hodgkin lymphoma, non-Hodgkin lymphomas, myofibroblastic sarcoma, rhabdoid, histiocytic sarcoma, embryonal carcinoma, adenocarcinoma, mesothelioma, mixed germ cell tumors (GCT), non-seminomas GCT, head and neck carcinoma, yolk sac tumor, angiosarcoma, pituitary adenoma, dysgerminoma, teratoma, and seminoma.

22. The CD30 chimeric antigen receptor, wherein said CD30 chimeric antigen receptor is:

(SEQ ID NO: 26)
MEFGLSWLFLVAILKGVQCSRDIVLTQSPASLAVSLGQRATISCKASQSV

DFDGDSYMNWYQQKPGQPPKVLIYAASNLESGIPARFSGSGSGTDFTLNI

HPVEEEDAATYYCQQSNEDPWTFGGGTKLEIKGGGSGGGGQIQLQQSGPE

VVKPGASVKISCKASGYTFTDYYITWVKQKPGQGLEWIGWIYPGSGNTKY

NEKFKGKATLTVDTSSSTAFMQLSSLTSEDTAVYFCANYGNYWFAYWGQG

TQVTVSAGSELPTQGTFSNVSTNVSPAPRPPTPAPTIASQPLSLRPEACR

PAAGGAVHTRGLDFACDIYIWAPLAGTCGVLLLSLVITLYCNHRNEFRSK

RSRLLHSDYMNMTPRRPGPTRKHYQPYAPPRDFAAYRSKRGRKKLLYIFK

QPFMRPVQTTQEEDGCSCRFPEEEEGGCELRVKFSRSADAPAYQQGQNQL

YNELNLGRREEYDVLDKRRGRDPEMGGKPRRKNPQEGLYNELQKDKMAEA

YSEIGMKGERRRGKGHDGLYQGLSTATKDTYDALHMQALPPR*.

23. The nucleotide sequence which encodes a CD30 chimeric antigen receptor, which is (SEQ ID NO: 28)
ATGGAGTTTGGGCTCTCCTGGCTCTTCCTGGTCGCGATTCTGAAGGGGGT

CCAGTGTTCACGAGATATCGTCCTGACTCAGAGTCCTGCCAGCCTGGCAG

TCTCCCTGGGACAGAGAGCTACCATAAGTTGTAAAGCATCACAGTCTGTT

GATTTCGATGGCGACAGCTATATGAATTGGTACCAGCAAAAACCCGGCCA

GCCCCCGAAAGTTTTGATCTATGCAGCCTCTAACTTGGAAAGCGGCATTC

CTGCGCGATTCAGTGGCAGCGGGAGTGGTACAGATTTCACCCTGAACATA

CACCCAGTCGAAGAGGAGGACGCAGCCACATATTACTGCCAACAATCTAA

CGAGGATCCATGGACTTTTGGGGGCGGCACTAAACTCGAAATCAAGGGCG

GAGGTTCAGGCGGAGGAGGGCAGATTCAACTGCAGCAATCAGGACCCGAG

GTGGTCAAACCAGGTGCCAGTGTCAAGATATCTTGCAAGGCATCCGGATA

TACATTTACCGACTATTACATTACCTGGGTCAAGCAGAAACCCGGGCAAG

GACTTGAATGGATTGGATGGATCTACCCTGGTAGCGGCAACACCAAATAC

AACGAAAAGTTTAAAGGGAAGGCAACCCTGACTGTAGACACCTCCAGCTC

CACAGCATTCATGCAGCTCTCCTCACTGACCTCCGAGGACACAGCAGTGT

ATTTCTGTGCTAATTACGGTAATTACTGGTTCGCCTATTGGGGCCAGGGA

ACCCAAGTGACCGTTTCAGCTGGATCCGAACTTCCTACTCAGGGGACTTT

CTCAAACGTTAGCACAAACGTAAGTCCCGCCCCAAGACCCCCCACACCTG

CGCCGACCATTGCTTCTCAACCCCTGAGTTTGAGACCCGAGGCCTGCCGG

CCAGCTGCCGGCGGGCCGTGCATACAAGAGGACTCGATTTCGCTTGCGA

CATCTACATCTGGGCTCCCCTCGCTGGCACCTGTGGGGTGCTGCTGCTGT

CACTCGTGATCACCCTTTATTGCAACCATCGAAACGAATTCAGAAGTAAA

CGGTCAAGGCTTCTGCACAGCGATTATATGAATATGACACCAAGAAGACC

TGGTCCAACCCGGAAACACTATCAGCCCTACGCGCCCCCTAGAGACTTCG

CAGCATACCGCTCTAAGAGAGGGAGAAAAAAATTGCTCTATATTTTTAAA

CAACCATTTATGAGGCCCGTACAGACAACTCAGGAAGAGGATGGCTGTAG

TTGCCGCTTCCCAGAGGAGGAGGAAGGAGGCTGCGAGTTGAGAGTTAAAT

TCAGTAGAAGTGCGGATGCGCCTGCTTACCAGCAGGGCCAGAACCAACTG

TACAATGAACTGAATCTCGGGCGCCGAGAAGAGTATGACGTCCTCGATAA

GCGGAGGGGTAGGGATCCTGAAATGGGTGGGAAGCCAAGAAGAAAAAACC

CCCAGGAAGGACTGTATAACGAACTTCAGAAGGACAAGATGGCAGAGGCC

TACTCTGAGATTGGCATGAAAGGCGAACGACGGCGCGGTAAAGGTCATGA

CGGGCTGTACCAGGGCCTGTCCACAGCGACGAAGGACACTTACGACGCCC

TGCACATGCAGGCACTCCCCCCCCAGGTGA.

* * * * *

UNITED STATES PATENT AND TRADEMARK OFFICE
CERTIFICATE OF CORRECTION

PATENT NO. : 11,845,804 B2
APPLICATION NO. : 16/979839
DATED : December 19, 2023
INVENTOR(S) : Biagio De Angelis et al.

It is certified that error appears in the above-identified patent and that said Letters Patent is hereby corrected as shown below:

On the Title Page

Column 2 (Item (57) Abstract), Line 2, Line after "CD30+" insert -- . --.

Column 2 (Item (57) Abstract), Line 4, delete "C– terminus," and insert -- C-terminus, --.

Page 2, Column 1 (item (56) Other Publications), Line 37, delete "www.moleculartheraoy.com," and insert -- www.moleculartherapy.com, --.

Page 2, Column 2 (item (56) Other Publications), Line 6, delete "OncoImmunologu" and insert -- Oncoimmunology --.

Page 2, Column 2 (item (56) Other Publications), Line 25, delete "neroblastoma"" and insert -- neuroblastoma" --.

Page 2, Column 2 (item (56) Other Publications), Line 28, delete "Signle" and insert -- Single --.

Page 2, Column 2 (item (56) Other Publications), Line 63, delete "Trail"" and insert -- Trial" --.

Page 3, Column 1 (item (56) Other Publications), Line 3, delete "Hournal" and insert -- Journal --.

Page 3, Column 1 (item (56) Other Publications), Line 5-6, delete "Actication" and insert -- Activation --.

Page 3, Column 1 (item (56) Other Publications), Line 16, delete "166" and insert -- 1BB --.

In the Drawings

Sheet 5 of 23 (Fig. 3), Line 10 (approx.), delete "Diluition" and insert -- Dilution --.

Signed and Sealed this
Sixteenth Day of July, 2024

Katherine Kelly Vidal
*Director of the United States Patent and Trademark Office*

CERTIFICATE OF CORRECTION (continued)

Sheet 6 of 23 (Fig. 3), Line 10 (approx.), delete "Diluition" and insert -- Dilution --.

Sheet 7 of 23 (Fig. 3), Line 10 (approx.), delete "Diluition" and insert -- Dilution --.

Sheet 16 of 23 (Fig. 10), and on the title page, the illustrative print figure, Line 3 (approx.) (Y-axis), delete "Bioluminiscence" and insert -- Bioluminescence --.

Sheet 17 of 23 (Fig. 11), Line 2 (approx.) (Y-axis), delete "Bioluminiscence" and insert -- Bioluminescence --.

Sheet 17 of 23 (Fig. 11), Line 11 (approx.), delete "Rappresentation" and insert -- Representation --.

Sheet 18 of 23 (Fig. 12), Line 2 (approx.) (Y-axis), delete "Bioluminiscence" and insert -- Bioluminescence --.

In the Specification

Column 1, Line 54, delete "(myofibroblasticsarcoma" and insert -- (myofibroblastic sarcoma --.

Column 3, Line 53, delete "Galectin1" and insert -- Galectin 1 --.

Column 4, Line 12, delete "CD19+B" and insert -- CD19+ B --.

Column 6, Line 54, delete "28.OX40ζ." and insert -- 28.OX40.ζ. --.

Column 6, Line 60, delete "(FIG." and insert -- (FIGS. --.

Column 7, Line 5, delete "Karpass" and insert -- Karpas --.

Column 7, Line 8, delete "(FIG." and insert -- (FIGS. --.

Column 7, Line 18, delete "(FIG." and insert -- (FIGS. --.

Column 7, Line 23, delete "Karpa299" and insert -- Karpas299 --.

Column 7, Line 27, delete "(FIG." and insert -- (FIGS. --.

Column 7, Line 34, delete "C– terminus:" and insert -- C-terminus: --.

Column 7, Line 41-48, delete "DIVLTQSPASLAVSLGQRATISCKASQSVDFDGDSYMNWYQQ KPGQPPKVLIYAASNLESGIPARFSGSGSGTDFTLNIHPVEEEDAATYYC QQSNEDPWTFGGGTKLEIK (SEQ ID NO:2) and AC10 VH sequence: QIQLQQSGPEVVKPGASVKISCKASGYTFTDYYITWVKQKPG QGLEWIGWIYPGSGNTKYNEKFKGKATLTVDTSSSTAFMQLSSLTSEDT AVYFCANYGNYWFAYWGQGTQVTVSA" and insert
-- DIVLTQSPASLAVSLGQRATISCKASQSVDFDGDSYMNWYQQKPGQPPKVLIYAASNLESG

CERTIFICATE OF CORRECTION (continued)
U.S. Pat. No. 11,845,804 B2

IPARFSGSGSGTDFTLNIHPVEEEDAATYYCQQSNEDPWTFGGGTKLEIK (SEQ ID NO:2) and AC10 VH sequence:
QIQLQQSGPEVVKPGASVKISCKASGYTFTDYYITWVKQKPGQGLEWIGWIYPGSGNTKYNE
KFKGKATLTVDTSSSTAFMQLSSLTSEDTAVYFCANYGNYWFAYWGQGTQVTVSA --.

Column 7, Line 53, delete "NO" and insert -- NO: --.

Column 7, Line 54-64, delete "ΔCD19:PEEPLVVKVEEGDNAVLQCLKGTSDGPTQQLTWS
RESPLKPFLKLSLGLPGLGIHMRPLAIWLFIFNVSQQMGGFYLCQPGPPS
EKAWQPGWTVNVEGSGELFRWNVSDLGGLGCGLKNRSSEGPSSPSG
KLMSPKLYVWAKDRPEIWEGEPPCLPPRDSLNQSLSQDLTMAPGSTLW
LSCGVPPDSVSRGPLSWTHVHPKGPKSLLSLELKDDRPARDMWVMET
GLLLPRATAQDAGKYYCHRGNLTMSFHLEITARPVLWHWLLRTGGWK" and insert
-- ΔCD19:PEEPLVVKVEEGDNAVLQCLKGTSDGPTQQLTWSRESPLKPFLKLSLGLPGLGIHM
RPLAIWLFIFNVSQQMGGFYLCQPGPPSEKAWQPGWTVNVEGSGELFRWNVSDLGGLGCGL
KNRSSEGPSSPSGKLMSPKLYVWAKDRPEIWEGEPPCLPPRDSLNQSLSQDLTMAPGSTLWLS
CGVPPDSVSRGPLSWTHVHPKGPKSLLSLELKDDRPARDMWVMETGLLLPRATAQDAGKY
YCHRGNLTMSFHLEITARPVLWHWLLRTGGWK --.

Column 7, Line 53, delete "ID.NO:5)" and insert -- ID NO:5) --.

Column 7, Line 66-67 - Column 8, Line 1-5, delete
"KEACPTGLYTHSGECCKACNLGEGVAQPCGANQTVCEPCLDSV
TFSDVVSATEPCKPCTECVGLQSMSAPCVEADDAVCRCAYGYYQDETT
GRCEACRVCEAGSGLVFSCQDKQNTVCEECPDGTYSDEANHVDPCLP
CTVCEDTERQLRECTRWADAECEEIPGRWITRSTPPEGSDSTAPSTQEP
EAPPEQDLIASTVAGVVTTVMGSSQPVVTRGTTDN" and insert
-- KEACPTGLYTHSGECCKACNLGEGVAQPCGANQTVCEPCLDSVTFSDVVSATEPCKPCTE
CVGLQSMSAPCVEADDAVCRCAYGYYQDETTGRCEACRVCEAGSGLVFSCQDKQNTVCEE
CPDGTYSDEANHVDPCLPCTVCEDTERQLRECTRWADAECEEIPGRWITRSTPPEGSDSTAPS
TQEPEAPPEQDLIASTVAGVVTTVMGSSQPVVTRGTTDN --.

Column 8, Line 12 (approx.), delete "hingeCD8α:" and insert -- hinge CD8α: --.

Column 8, Line 19-32, delete
"ESKYGPPCPSCPAPEFLGGPSVFLFPPKPKDTLMISRTPEVTCVVVDVS
QEDPEVQFNWYVDGVEVHNAKTKPREEQFNSTYRVVSVLTVLHQDWL
NGKEYKCKVSNKGLPSSIEKTISKAKGQPREPQVYTLPPSQEEMTKNQV
SLTCLVKGFYPSDIAVEWESNGQPEN NYKTTPPVLDSDGSFFLYSRLTV
DKSRWQEGNVFSCSVMHEALHNHYTQKSLSLSLGK (SEQ ID NO:9); hinge CH3
(UNIPROTKB:P01861):ESKYGPPCPSCPGQPREPQVYTLPPSQEEMTK
NQVSLTCLVKGFYPSDIAVEWESNGQPENNYKTTPPVLDSDGSFFLYSR
LTVDKSRWQEGNVFSCSVMHEALHNHYTQKSLSLSLGK" and insert
-- ESKYGPPCPSCPAPEFLGGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTISKAKGQ
PREPQVYTLPPSQEEMTKNQVSLTCLVKGFYPSDIAVEWESNGQPENNYKTTPPVLDSDGSFF
LYSRLTVDKSRWQEGNVFSCSVMHEALHNHYTQKSLSLSLGK (SEQ ID NO:9); hinge CH3
(UNIPROTKB:P01861):ESKYGPPCPSCPGQPREPQVYTLPPQEEMTKNQVSLTCLVKGFYP
SDIAVEWESNGQPENNYKTTPPVLDSDGSFFLYSRLTVDKSRWQEGNVFSCSVMHEALHNHY
TQKSLSLSLGK --.

Column 8, Line 42, delete "NO" and insert -- NO: --.

Column 8, Line 52-56, delete
"RVKFSRSADAPAYQQGQNQLYNELNLGRREEYDVLDKRRGRDPEMGG
KPRRKNPQEGLYNELQKDKMAEAYSEIGMKGERRRGKGHDGLYQGLS
TATKDTYDALHMQALPPR*" and insert
-- RVKFSRSADAPAYQQGQNQLYNELNLGRREEYDVLDKRRGRDPEMGGKPRRKNPQEGL
YNELQKDKMAEAYSEIGMKGERRRGKGHDGLYQGLSTATKDTYDALHMQALPPR* --.

Column 8, Line 64-67 - Column 9, Line 1, delete
"RVKFSRSADAPAYQQGQNQLYNELNLGRREEYDVLDKRRGRDPEMGG
KPRRKNPQEGLYNELQKDKMAEAYSEIGMKGERRRGKGHDGLYQGLS
TATKDTYDALPMQALPPR*" and insert
-- RVKFSRSADAPAYQQGQNQLYNELNLGRREEYDVLDKRRGRDPEMGGKPRRKNPQEGL
YNELQKDKMAEAYSEIGMKGERRRGKGHDGLYQGLSTATKDTYDALHMQALPPR* --.

Column 9, Line 6, delete "NO" and insert -- NO: --.

Column 9, Line 38-45, delete "DIVLTQSPASLAVSLGQRATISCKASQSVDFDGDSYMNWYQQ
KPGQPPKVLIYAASNLESGIPARFSGSGSGTDFTLNIHPVEEEDAATYYC
QQSNEDPWTFGGGTKLEIK (SEQ ID NO:2) and AC10 VH sequence:
QIQLQQSGPEVVKPGASVKISCKASGYTFTDYYITWVKQKPG
QGLEWIGWIYPGSGNTKYNEKFKGKATLTVDTSSSTAFMQLSSLTSEDT
AVYFCANYGNYWFAYWGQGTQVTVSA" and insert
-- DIVLTQSPASLAVSLGQRATISCKASQSVDFDGDSYMNWYQQKPGQPPKVLIYAASNLESG
IPARFSGSGSGTDFTLNIHPVEEEDAATYYCQQSNEDPWTFGGGTKLEIK (SEQ ID NO:2) and
AC10 VH sequence:
QIQLQQSGPEVVKPGASVKISCKASGYTFTDYYITWVKQKPGQGLEWIGWIYPGSGNTKYNE
KFKGKATLTVDTSSSTAFMQLSSLTSEDTAVYFCANYGNYWFAYWGQGTQVTVSA --.

Column 9, Line 63-67, delete
"RVKFSRSADAPAYQQGQNQLYNELNLGRREEYDVLDKRRGRDPEMGG
KPRRKNPQEGLYNELQKDKMAEAYSEIGMKGERRRGKGHDGLYQGLS
TATKDTYDALHMQALPPR* (SEQ ID NO:23)." and insert
-- RVKFSRSADAPAYQQGQNQLYNELNLGRREEYDVLDKRRGRDPEMGGKPRRKNPQEGLY
NELQKDKMAEAYSEIGMKGERRRGKGHDGLYQGLSTATKDTYDALHMQALPPR* (SEQ ID
NO:23). --.

CERTIFICATE OF CORRECTION (continued)
U.S. Pat. No. 11,845,804 B2

Column 10, Line 9-17 (approx.), delete
"DIVLTQSPASLAVSLGQRATISCKASQSVDFDGDSYMNWYQQ
KPGQPPKVLIYAASNLESGIPARFSGSGSGTDFTLNIHPVEEEDAATYYC
QQSNEDPWTFGGGTKLEIK (SEQ ID NO:2) and AC10 VH sequence:
QIQLQQSGPEVVKPGASVKISCKASGYTFTDYYITWVKQKPG
QGLEWIGWIYPGSGNTKYNEKFKGKATLTVDTSSSTAFMQLSSLTSEDT
AVYFCANYGNYWFAYWGQGTQVTVSA" and insert
-- DIVLTQSPASLAVSLGQRATISCKASQSVDFDGDSYMNWYQQKPGQPPKVLIYAASNLESG
IPARFSGSGSGTDFTLNIHPVEEEDAATYYCQQSNEDPWTFGGGTKLEIK (SEQ ID NO:2) and
AC10 VH sequence:
QIQLQQSGPEVVKPGASVKISCKASGYTFTDYYITWVKQKPGQGLEWIGWIYPGSGNTKYNE
KFKGKATLTVDTSSSTAFMQLSSLTSEDTAVYFCANYGNYWFAYWGQGTQVTVSA --.

Column 19, Line 36, delete "(Q." and insert -- (ζ). --.

Column 19, Line 44, delete "Δ.CD34." and insert -- ΔCD34. --.

Column 20, Line 53, delete "**0.0001." and insert -- **≤0.0001. --.

Column 21, Line 2, delete "**0.0001." and insert -- **≤0.0001. --.

Column 21, Line 13, delete "CARGD2.28-41Bζ" and insert -- CARGD2.28-41BBζ --.

Column 21, Line 16, delete "CARGD2.28-41Bζ" and insert -- CARGD2.28-41BBζ --.

Column 21, Line 25, delete "CARGD2.28-41Bζ" and insert -- CARGD2.28-41BBζ --.

Column 21, Line 27, delete "CARGD2.28-41Bζ" and insert -- CARGD2.28-41BBζ --.

Column 21, Line 32, delete "**0.0001." and insert -- **≤0.0001. --.

Column 21, Line 41, delete "CARGD2.28-41Bζ" and insert -- CARGD2.28-41BBζ --.

Column 21, Line 52, delete "sistemic" and insert -- systemic --.

Column 21, Line 60-61, delete "Bioluminiscence" and insert -- Bioluminescence --.

Column 21, Line 64, delete "28.4-1BBQ" and insert -- 28.4-1BBζ --.

Column 22, Line 1, delete "28.4-1BBQ" and insert -- 28.4-1BBζ --.

Column 22, Line 21, delete "Bioluminiscence" and insert -- Bioluminescence --.

Column 22, Line 26, delete "CARCD30.28.OX40Bζ" and insert -- CARCD30.28.OX40ζ --.

Column 22, Line 42, delete "CARCD30.28-41Bζ" and insert -- CARCD30.28-41BBζ --.

CERTIFICATE OF CORRECTION (continued)
U.S. Pat. No. 11,845,804 B2

Column 23, Line 23, delete "(1," and insert -- (I, --.

Column 23, Line 25, delete "citokines" and insert -- cytokines --.

Column 23, Line 46, delete "**0.0001." and insert -- **≤0.0001. --.

Column 24, Line 38, delete "Lines." and insert -- Lines --.

Column 24, Line 53, delete "Lines." and insert -- Lines --.

Column 25, Line 26, delete "No 969/2015" and insert -- N °969/2015 --.

Column 25, Line 26-27, delete "No 669LB)," and insert -- N °669LB), --.

Column 25, Line 41, delete "Usa" and insert -- USA --.

Column 26, Line 39, delete "(No88/" and insert -- (N °88/ --.

Column 26, Line 41, delete "Il2rgtm1WjI/SzJ;" and insert -- Il2rgtm1Wjl/SzJ; --.

Column 26, Line 65, delete "an least" and insert -- at least --.

Column 27, Line 56, delete "1BBζ" and insert -- 1BB.ζ --.

Column 29, Line 4, delete "ml)(FIG." and insert -- ml) (FIG. --.

Column 29, Line 51, delete "(FIG." and insert -- (FIGS. --.

Column 29, Line 55, delete "(FIG." and insert -- (FIGS. --.

Column 30, Line 1, delete "SK-ES-1(FIG. 7J)." and insert -- SK-ES-1 (FIG. 7J). --.

Column 30, Line 7, delete "(FIG." and insert -- (FIGS. --.

Column 30, Line 16, delete "(FIG." and insert -- (FIGS. --.

Column 30, Line 24, delete "respectively)," and insert -- respectively). --.

Column 30, Line 40, delete "(FIG." and insert -- (FIGS. --.

Column 30, Line 62, delete "(FIG." and insert -- (FIGS. --.

Column 31, Line 42, delete "(FIG." and insert -- (FIGS. --.

Column 31, Line 44, delete "(FIG." and insert -- (FIGS. --.

CERTIFICATE OF CORRECTION (continued)
U.S. Pat. No. 11,845,804 B2

Column 32, Line 30, delete "CAR.T" and insert -- CAR T --.

Column 33, Line 38, delete "Karpa299" and insert -- Karpas299 --.

Column 34, Line 5, delete "113(8-17." and insert -- 113(8-17). --.

Column 36, Line 10 (approx.), delete "(90-7." and insert -- (90-7). --.

Column 36, Line 37 (approx.), delete "(29." and insert -- (29). --.

In the Claims

Column 65, Line 27 (approx.), Claim 1, delete "C– terminus:" and insert -- C-terminus: --.

Column 65, Line 32-41 (approx.), Claim 1, delete
"DIVLTQSPASLAVSLGQRATISCKASQSVDFDGDSYMNWYQQKPGQPPKVLIY
AASNLESGIPARFSGSGSGTDFTLNIHPVEEEDAATYYCQQSNEDPWTFGGGTKLEIK (SEQ ID
NO:2) and AC10 VH sequence:
QIQLQQSGPEVVKPGASVKISCKASGYTFTDYYITWVKQKPGQGLEWIGWIYP
GSGNTKYNEKFKGKATLTVDTSSSTAFMQLSSLTSEDTAVYFCANYGNYWFAYWGQG
TQVTVSA" and insert -- DIVLTQSPASLAVSLGQRATISCKASQSVDFDGDSYMNWYQQKPGQ
PPKVLIYAASNLESGIPARFSGSGSGTDFTLNIHPVEEEDAATYYCQQSNEDPWTFGGGTKLE
IK (SEQ ID NO:2) and AC10 VH sequence:
QIQLQQSGPEVVKPGASVKISCKASGYTFTDYYITWVKQKPGQGLEWIGWIYPGSGNTKYNE
KFKGKATLTVDTSSSTAFMQLSSLTSEDTAVYFCANYGNYWFAYWGQGTQVTVSA --.

Column 65, Line 46-67 (approx.), Claim 1, delete
"ΔCD19:PEEPLVVKVEEGDNAVLQCLKGTSDGPTQQLTWSRESPLKPFLKLSLGLPGLGIH
MRPLAIWLFIFNVSQQMGGFYLCQPGPPSEKAWQPGWTVNVEGSGELFRWNVSDLGGL
GCGLKNRSSEGPSSPSGKLMSPKLYVWAKDRPEIWEGEPPCLPPRDSLNQSLSQDLTMA
PGSTLWLSCGVPPDSVSRGPLSWTHVHPKGPKSLLSLELKDDRPARDMWVMETGLLLP
RATAQDAGKYYCHRGNLTMSFHLEITARPVLWHWLLRTGGWK (SEQ ID NO:5);
NGFR:KEACPTGLYTHSGECCKACNLGEGVAQPCGANQTVCEPCLDSVTFSDVVSATEP
CKPCTECVGLQSMSAPCVEADDAVCRCAYGYYQDETTGRCEACRVCEAGSGLVFSCQ
DKQNTVCEECPDGTYSDEANHVDPCLPCTVCEDTERQLRECTRWADAECEEIPGRWITR
STPPEGSDSTAPSTQEPEAPPEQDLIASTVAGVVTTVMGSSQPVVTRGTTDN" and insert
-- ΔCD19:PEEPLVVKVEEGDNAVLQCLKGTSDGPTQQLTWSRESPLKPFLKLSLGLPGLGI
HMRPLAIWLFIFNVSQQMGGFYLCQPGPPSEKAWQPGWTVNVEGSGELFRWNVSDLGGLGC
GLKNRSSEGPSSPSGKLMSPKLYVWAKDRPEIWEGEPPCLPPRDSLNQSLSQDLTMAPGSTLW
LSCGVPPDSVSRGPLSWTHVHPKGPKSLLSLELKDDRPARDMWVMETGLLLPRATAQDA
GKYYCHRGNLTMSFHLEITARPVLWHWLLRTGGWK (SEQ ID NO:5);
NGFR:KEACPTGLYTHSGECCKACNLGEGVAQPCGANQTVCEPCLDSVTFSDVVSATEPCKPC
TECVGLQSMSAPCVEADDAVCRCAYGYYQDETTGRCEACRVCEAGSGLVFSCQDKQNTV
CEECPDGTYSDEANHVDPCLPCTVCEDTERQLRECTRWADAECEEIPGRWITRSTPPEGSD
STAPSTQEPEAPPEQDLIASTVAGVVTTVMGSSQPVVTRGTTDN --.

CERTIFICATE OF CORRECTION (continued)
U.S. Pat. No. 11,845,804 B2

Column 66, Line 30-39 (approx.), Claim 1, delete
"ESKYGPPCPSCPAPEFLGGPSVFLFPPKPKDTLMISRTPEVTCVVVDVSQEDPEVQFNWY
VDGVEVHNAKTKPREEQFNSTYRVVSVLTVLHQDWLNGKEYKCKVSNKGLPSSIEKTIS
KAKGQPREPQVYTLPPSQEEMTKNQVSLTCLVKGFYPSDIAVEWESNGQPENNYKTTPP
VLDSDGSFFLYSRLTVDKSRWQEGNVFSCSVMHEALHNHYTQKSLSLSLGK" and insert
-- ESKYGPPCPSCPAPEFLGGPSVFLFPPKPKDTLMISRTPEVTCVVVDVSQEDPEVQFNWYVD
GVEVHNAKTKPREEQFNSTYRVVSVLTVLHQDWLNGKEYKCKVSNKGLPSSIEKTISKAKG
QPREPQVYTLPPSQEEMTKNQVSLTCLVKGFYPSDIAVEWESNGQPENNYKTTPPVLDSDGS
FFLYSRLTVDKSRWQEGNVFSCSVMHEALHNHYTQKSLSLSLGK --.

Column 66, Line 39-44 (approx.), Claim 1, delete
"ESKYGPPCPSCPGQPREPQVYTLPPSQEEMTKNQVSLTCLVKGFYPSDIAVEWESNGQPE
NNYKTTPPVLDSDGSFFLYSRLTVDKSRWQEGNVFSCSVMHEALHNHYTQKSLSLSLG K"
and insert -- ESKYGPPCPSCPGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSL
GK --.

Column 66, Line 54-58, Claim 1, delete
"RVKFSRSADAPAYQQGQNQLYNELNLGRREEYDVLDKRRGRDPEMGGKPRRKNPQEG
LYNELQKDKMAEAYSEIGMKGERRRGKGHDGLYQGLSTATKDTYDALHMQALPPR" and
insert -- RVKFSRSADAPAYQQGQNQLYNELNLGRREEYDVLDKRRGRDPEMGGKPRRKNP
QEGLYNELQKDKMAEAYSEIGMKGERRRGKGHDGLYQGLSTATKDTYDALHMQALPPR --.

Column 67, Line 13-22 (approx.), Claim 6, delete
"DIVLTQSPASLAVSLGQRATISCKASQSVDFDGDSYMNWYQQKPGQPPKVLIYAASNLE
SGIPARFSGSGSGTDFTLNIHPVEEEDAATYYCQQSNEDPWTFGGGTKLEIK (SEQ ID NO:2)
and AC10 VH sequence
QIQLQQSGPEVVKPGASVKISCKASGYTFTDYYITWVKQKPGQGLEWIGWIYPGSGN
TKYNEKFKGKATLTVDTSSSTAFMQLSSLTSEDTAVYFCANYGNYWFAYWGQGTQVT VSA"
and insert
-- DIVLTQSPASLAVSLGQRATISCKASQSVDFDGDSYMNWYQQKPGQPPKVLIYAASNLES
GIPARFSGSGSGTDFTLNIHPVEEEDAATYYCQQSNEDPWTFGGGTKLEIK (SEQ ID NO:2) and
AC10 VH sequence
QIQLQQSGPEVVKPGASVKISCKASGYTFTDYYITWVKQKPGQGLEWIGWIYPGSGNTKYNE
KFKGKATLTVDTSSSTAFMQLSSLTSEDTAVYFCANYGNYWFAYWGQGTQVTVSA --.

Column 67, Line 41-45 (approx.), Claim 6, delete
"RVKFSRSADAPAYQQGQNQLYNELNLGRREEYDVLDKRRGRDPEMGGKPRRKNPQEG
LYNELQKDKMAEAYSEIGMKGERRRGKGHDGLYQGLSTATKDTYDALPMQALPPR" and
insert
-- RVKFSRSADAPAYQQGQNQLYNELNLGRREEYDVLDKRRGRDPEMGGKPRRKNPQEGLY
NELQKDKMAEAYSEIGMKGERRRGKGHDGLYQGLSTATKDTYDALMQALPPR --.

Column 69, Line 39, Claim 21, delete "lymphomas," and insert -- lymphoma, --.